(12) United States Patent
Luo et al.

(10) Patent No.: US 10,967,003 B2
(45) Date of Patent: Apr. 6, 2021

(54) FUNCTIONAL SEGREGATED TELODENDRIMERS AND NANOCARRIERS AND METHODS OF MAKING AND USING SAME

(71) Applicant: The Research Foundation for the State University of New York, Syracuse, NY (US)

(72) Inventors: Juntao Luo, Jamesville, NY (US); Changying Shi, Jamesville, NY (US); Dandan Guo, Syracuse, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 16/674,549

(22) Filed: Nov. 5, 2019

(65) Prior Publication Data

US 2020/0254012 A1 Aug. 13, 2020

Related U.S. Application Data

(63) Continuation of application No. 15/517,544, filed as application No. PCT/US2015/054474 on Oct. 7, 2015, now Pat. No. 10,463,694.

(60) Provisional application No. 62/060,946, filed on Oct. 7, 2014.

(51) Int. Cl.
| | |
|---|---|
| *A61K 33/24* | (2019.01) |
| *A61K 47/34* | (2017.01) |
| *A61K 9/107* | (2006.01) |
| *A61K 47/60* | (2017.01) |
| *A61K 47/59* | (2017.01) |
| *A61K 31/337* | (2006.01) |

(52) U.S. Cl.
CPC .............. *A61K 33/24* (2013.01); *A61K 9/107* (2013.01); *A61K 31/337* (2013.01); *A61K 47/34* (2013.01); *A61K 47/595* (2017.08); *A61K 47/60* (2017.08)

(58) Field of Classification Search
CPC ................................ A61K 33/24; A61K 47/60
See application file for complete search history.

(56) References Cited

U.S. PATENT DOCUMENTS

| | | |
|---|---|---|
| 2008/0299220 A1 | 12/2008 | Tamarkin et al. |
| 2008/0312581 A1 | 12/2008 | Hardy |
| 2010/0038297 A1 | 2/2010 | Zhu et al. |
| 2011/0144281 A1 | 6/2011 | Zhu et al. |
| 2011/0274695 A1 | 11/2011 | Satyam |
| 2011/0286915 A1 | 11/2011 | Lam et al. |
| 2012/0322145 A1 | 12/2012 | Onofiok et al. |
| 2013/0164369 A1 | 6/2013 | Lam et al. |
| 2013/0165636 A1 | 6/2013 | Luo et al. |
| 2014/0363371 A1 | 12/2014 | Luo et al. |
| 2015/0056139 A1 | 2/2015 | Luo et al. |
| 2017/0252456 A1 | 9/2017 | Luo et al. |
| 2017/0266292 A1 | 9/2017 | Luo et al. |
| 2017/0290921 A1 | 10/2017 | Lam et al. |
| 2018/0079829 A1 | 3/2018 | Luo et al. |
| 2019/0112423 A1 | 4/2019 | Lam et al. |
| 2019/0292328 A1 | 9/2019 | Luo et al. |
| 2019/0328742 A1 | 10/2019 | Luo et al. |
| 2020/0009069 A1 | 1/2020 | Luo et al. |
| 2020/0254012 A1 | 8/2020 | Luo et al. |

FOREIGN PATENT DOCUMENTS

| | | |
|---|---|---|
| WO | 2010039496 A2 | 4/2010 |
| WO | 2010148346 A2 | 12/2010 |
| WO | 2012158622 A2 | 11/2012 |
| WO | 2013096388 A1 | 6/2013 |
| WO | 2015027054 A2 | 2/2015 |
| WO | 2016057657 A1 | 4/2016 |
| WO | 2017044933 A1 | 3/2017 |
| WO | 2018136778 A1 | 7/2018 |
| WO | 2018160759 A1 | 9/2018 |

OTHER PUBLICATIONS

Huang et al., Fine-Tuning Vitamin E-Containing Telodendrimers for Efficient Delivery of Gambogic Acid in Colon Cancer Treatment, Molecular Pharmaceutics, 2015, pp. 1-14.
Li et al., Well-Defined Reversible Boronate Crosslinked Nanocarriers for Targeted Drug Delivery in Response to Acidic pH Values cis-Diols, Supporting Information, Angewandte Cheme, pp. 7-10 2012.
Chen et at., Dual-Responseive Boronate Crosslinked Micelles for Targeted Drug Delivery, Angewandte Cheme, vol. 51, No. 22, pp. 5293-5295. May 29, 2012.
Cai et al., Telodendrimer nanocarrier for co-delivery of paclitaxel and cisplatin: A synergistic combination nanotherapy for ovarian cancer treatment, Biomaterials, vol. 37, pp. 456-468. Jan. 2015.
Xiao et al., A self-assembling nanoparticle for paclitaxel delivery in ovarian cancer, Biomaterials, vol. 30, No. 30, pp. 6006-6016 Oct. 1, 2009.
Li et al., Well-Defined Reversible Boronate Crosslinked Nanocarriers for Targeted Drug Delivery in Response to Acidic pH Values cis-diols, Supporting Information, Angewandte Cheme, vol. 51, No. 12, pp. 2864-2869. 2012.
Luo et al., Well-Defined, Size-Tunable, Multifunctional Micelles for Efficient Paclitaxel Delivery for Cancer Treatment, Bioconjugate Chemistry, vol. 21, No. 7, pp. 1216-1224. Jul. 21, 2010.
Shane Thomas, Search Report and Written Opinion for PCT/US2015/054474, pp. 1-7, Jan. 11, 2016.

*Primary Examiner* — Shawquia Jackson
(74) *Attorney, Agent, or Firm* — Michael Krenicky; Garrett Smith; Steven A. Wood, Jr.

(57) ABSTRACT

Provided are multiply functional telodendrimers. The telodendrimers can be used for combination drug delivery. The telodendrimers may have one or more crosslinking groups (e.g., reversible photocrosslinking groups). The telodendrimers can aggregate to form nanocarriers. Cargo such as combinations of drugs, imaging probes, and other materials may be sequestered in the core of the aggregates via noncovalent or covalent interactions with the telodendrimers. Such nanocarriers may be used in drug delivery applications and imaging applications.

18 Claims, 27 Drawing Sheets

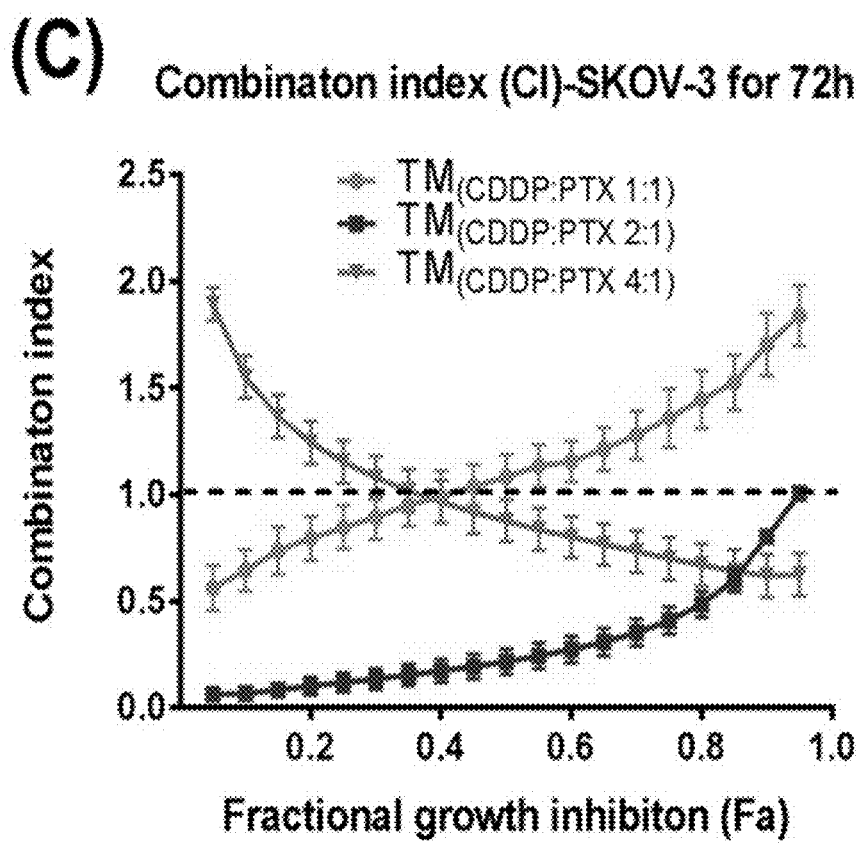
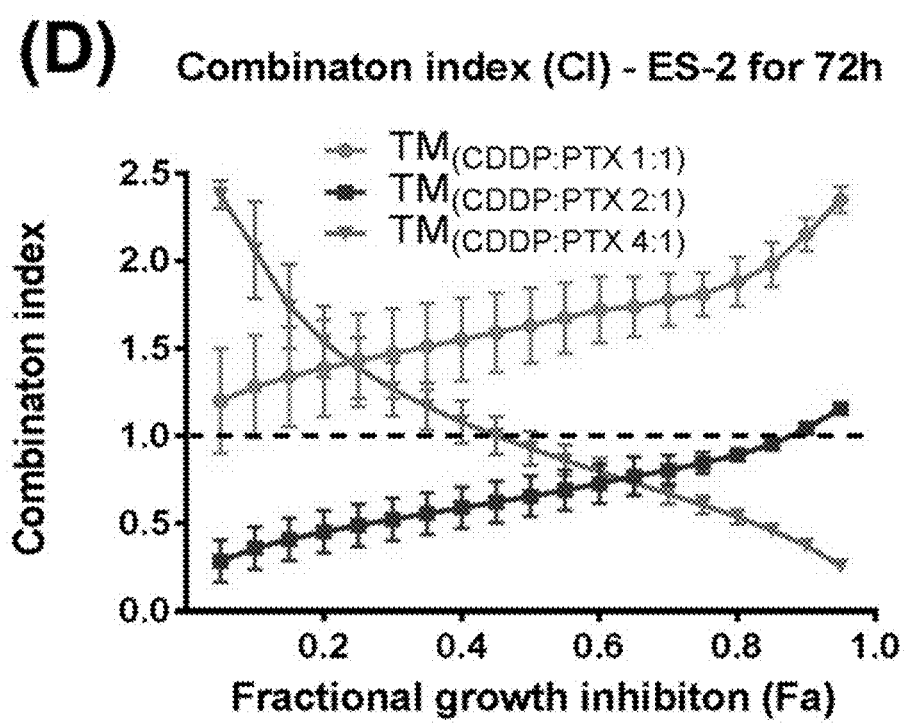
Figure 4 (cont.)

Figure 20

| Combination Chemotherapy | Drug#1 | Drug#2 | Drug#3 | Drug#4 | Drug#5 | Drug#6 | Drug#7 |
|---|---|---|---|---|---|---|---|
| ABVD | Doxorubicin | Bleomycin | Vinblastine | Dacarbazine | | | |
| AC | Doxorubicin | cyclophosphamide | | | | | |
| BEAM | Carmustine (BiCNU®) | Etoposide | Cytarabine | Melphalan | | | |
| BEP | Bleomycin | Etoposide | Cisplatin | | | | |
| Carbo MV | Carboplatin | Methotrexate | Vinblastine | | | | |
| Carboplatin & etoposide | Carboplatin | Etoposide | | | | | |
| CAV | Cyclophosphamide | Doxorubicin (adriamycin) | vincristine | | | | |
| ChlVPP | Chlorambucil | Vinblastine | Procarbazine | Prednisolone | | | |
| CHOP | Cyclophosphamide | Doxorubicin | Vincristine (Oncovin®) | Prednisolone | | | |
| Cisplatin, capecitabine and trastuzumab (herceptin) | Cisplatin | Capecitabine | Trastuzumab | | | | |
| Cisplating and fluorouracil | Cisplatin | Fluorouracil (5FU) | | | | | |
| Cisplatin and topotecan | Cisplatin | Topotecan | | | | | |
| CMF | Cyclophosphamide | Methotrexate | Fluorouracil | | | | |
| CTD | Cyclophosphamide | Thalidomide | Dexamethasone | | | | |
| CVP | Cyclophosphamide | Vincristine | Prednisolone | | | | |
| De Gramont | Fluorouracil | Folinic acid (also known as leucovorin or calcium folinate) | | | | | |
| DHAP | Dexamethasone | Cytarabine | Cisplatin | | | | |

Figure 20 (cont.)

| | | | | | | |
|---|---|---|---|---|---|---|
| Docetaxel and carboplatin | Docetaxel | Carboplatin | | | | |
| Docetaxel and cisplatin | Docetaxel | Cisplatin | | | | |
| Doxorubicin and ifosfamide | Doxorubicin | Ifosfamide | | | | |
| E-CMF (Epi-CMF) | Epirubicin | Cyclophosphamide | Methotrexate | Fluorouracil | | |
| EC | Epirubicin | Cyclophosphamide | | | | |
| ECF | Epirubicin | Cisplatin | Fluorouracil | | | |
| ECX | Epirubicin | Cisplatin | Capecitabine (Xeloda®) | | | |
| EOX | Epirubicin | Oxaliplatin (Eloxatin®) | Capecitabine | | | |
| ESHAP | Etoposide | Methylprednisolone | Cytarabine | Cisplatin | | |
| Etoposide and cisplatin | Etoposide | Cisplatin | | | | |
| FCR | Fludarabine | Cyclophosphamide | Rituximab | | | |
| FEC | Fluorouracil | Epirubicin | Cyclophosphamide | | | |
| FEC-T | Fluorouracil | Epirubicin | Cyclophosphamide | Docetaxel | | |
| FOLFIRINOX | Folinic acid | Fluorouracil | Irinotecan | Oxaliplatin | | |
| Gemcitabine (Gemzar®) and capecitabine | Gemcitabine | Capecitabine | | | | |
| GemCarbo | Gemcitabine | Carboplatin | | | | |
| Gemcitabine and cisplatin | Gemcitabine | Cisplatin | | | | |
| GemTaxol | Gemcitabine | Paclitaxel | | | | |
| Hyper CVAD | Cyclophosphamide | Vincristine | Doxorubicin | Dexamethasone (a steroid) | Methotrexate | Cytarabine |
| ICE | Ifosfamide | Carboplatin | Etoposide | | | |
| Irinotecan and cetuximab | Irinotecan (Campto®) | Cetuximab (Erbitux®) | | | | |
| Irinotecan with fluorouracil (5FU) and folinic acid | Irinotecan | Folinic acid | Fluorouracil | | | |

Figure 20 (cont.)

| MIC | Mitomycin | Ifosfamide | Cisplatin | | | | |
|---|---|---|---|---|---|---|---|
| NN | Methotrexate | Mitoxantrone | | | | | |
| MMM | Mitomycin | Methotrexate | Mitoxantrone | | | | |
| MPT | Melphalan | Prednisolone | Thalidomide | | | | |
| MVAC | Methotrexate | Vinblastine | Doxorubicin | Cisplatin | | | |
| MVP | Mitomycin | Vinblastine | Cisplatin | | | | |
| Oxaliplatin with 5FU and folinic acid | Oxaliplatin | Fluorouracil | Folinic acid | | | | |
| Oxaliplatin and capecitabine (Xeloda®) | Oxaliplatin | Capecitabine | | | | | |
| Paclitaxel and carboplatin (Taxol/Carbo) | Paclitaxel | Carboplatin | | | | | |
| Pemetrexed and cisplatin | Pemetrexed (Alimtra®) | Cisplatin | | | | | |
| PCV | Procarbazine | Lomustine (CCNU®) | Vincristine | | | | |
| PMitCEBO | Prednisolone | Mitoxantrone | (adriamycin) | Etoposide | Bleomycin | Vincritine (Oncovin®) | |
| POMB/ACE | Ciplatin | Vincristine | Methotrexate | Bleomycin | Dactinomycin | Cyclophosphamide | etoposide |
| R-CHOP | Rituximab | Cyclophosphamide | Doxorubicin (hydroxy-daunomycin and Adriamycin®) | Vincristine | Prednisolone (a steroid) | | |
| R-CVP | Rituximab | Cyclophosphamide | Vincristine | Prednisolone | | | |
| R-DHAP | Rituximab | Dexamethasone (a steroid) | Cytarabine (Ara C) | Cisplatin | | | |
| R-ESHAP | Rituximab | Etoposide | Methylprednisolone (a steroid) | Cisplatin | | | |

Figure 20(cont.)

| R-ICE | Rituximab (a monoclonal antibody) | Ifosfamide | Carboplatin | Etoposide | | | |
|---|---|---|---|---|---|---|---|
| TAC | Docetaxel (Taxotere®) | Doxorubicin | Cyclophosphamide | | | | |
| TC | Docetaxel | Cyclophosphamide | | | | | |
| TIP | Paclitaxel | Ifosfamide | Cisplatin | | | | |
| VAD | Vincristine | Doxorubicin | Dexamethasone | | | | |
| Vinorelbine and Carboplatin | Vinorelbine (Navelbine®) | Carboplatin | | | | | |
| Vinorelbine and cisplatin – also VP (or NP) | Vinorelbine | Cisplatin | | | | | |

FUNCTIONAL SEGREGATED TELODENDRIMERS AND NANOCARRIERS AND METHODS OF MAKING AND USING SAME

CROSS-REFERENCE TO RELATED APPLICATIONS

This application is a continuation of U.S. application Ser. No. 15/517,544, filed on Apr. 7, 1017, which is the national stage entry of International Application No. PCT/US2015/054474, filed on Oct. 7, 2015, which claims priority to U.S. Provisional Application No. 62/060,946, filed on Oct. 7, 2014, the disclosures of which are incorporated herein by reference.

STATEMENT REGARDING FEDERALLY SPONSORED RESEARCH

This disclosure was made with government support under contract no. 1R01CA140449 awarded by the National Institutes of Health and National Cancer Institute. The government has certain rights in the disclosure.

FIELD OF THE DISCLOSURE

This disclosure generally relates to telodendrimers, and methods of making and using telodendrimers. More particularly, the disclosure relates to functional segregated telodendrimers.

BACKGROUND OF THE DISCLOSURE

Targeted drug delivery results in significant clinical benefits for disease treatment, especially for cancer. Encapsulation of cytotoxic anticancer drugs inside a nanoparticle is able to decrease side toxicity and improve the life quality of patient. In addition, passive or active targeting effect of the nanocarrier is able to deliver significantly high dose of chemodrugs to tumors and yields improved cancer treatment or even cure of the disease. Stability, drug loading capacity, reproducibility and biocompatibility are critical for the clinical translation of all drug delivery systems.

Combination chemotherapy involves using two or more drugs proven effective against a tumor type. As a treatment strategy it has accounted for major advances in cancer treatment, in part because it helps overcome the rapid development of drug resistance by tumor cells and implicitly addresses the heterogeneity of cancer cells and that at any given time individual cells making up a tumor will be in different phases of the cell cycle. Cell-cycle specific and cell-cycle non-specific drugs are given in combination, because the cell-cycle specific drugs reduce the tumor growth factor, and cell-cycle non-specific drugs help to reduce the tumor burden. In addition, combining drugs can decrease the incidence and severity of side effects of therapy.

For example, Cisplatin (CDDP) and paclitaxel (PTX) are two of the most popular chemotherapeutic drugs used in combination for the treatment of many cancers, including rarely curable ovarian cancers. CDDP binds DNA and inhibits DNA synthesis; while PTX arrests the cell cycle by stabilizing microtubules. Given their distinct mechanisms of action, it has been demonstrated that co-administration of CDDP and PTX can achieve synergistic effects on tumor cells. Interestingly, PTX shows strong synergism when it is administered first; however, it shows antagonistic effects when administered after CDDP in ovarian cancer patients. Although PTX is ~1000 times more potent than CDDP (IC50s: low nM vs low μM) in a wide variety of cancer cells in culture, a much higher dose of PTX (175 mg/m$^2$ every three weeks) than CDDP (75-100 mg/m$^2$ every four weeks) can be used for cancer treatment. This reflects the relative low systemic toxic side effects of PTX vs. CDDP, due to the fast in vivo clearance and metabolizing of organic PTX as compared with the heavy metal drug CDDP. On the other hand, the poor pharmacokinetics ($t_{1/2}$ in human: 0.34 hours (h)) and pharmacodynamic profiles (cytochrome P450 metabolism) of PTX may limit its accumulation in the tumor and hinder its in vivo potency. In contrast, CDDP dominantly binds to serum proteins and is eliminated and metabolized much slower in vivo. The dissociated CDDP and its metabolites lead to long-term drug exposure of tumor cells, as well as normal tissues. As a result, CDDP is one of the most active anticancer drugs, albeit with significant acute and chronic nephro-, oto-, and peripheral neuro-toxicity. Therefore, it is important for a PTX-based combination therapy to increase PTX bioavailability and drug exposure to tumor cells. Combination therapies employing CDDP as one of the drugs will be improved if the acute and chronic toxic side effects of CDDP are diminished. An optimal PTX/CDDP combination therapy should do both as well as administering or releasing the two drugs such that a synergistic effect on tumor cells is achieved.

Another combination therapy uses Doxorubicin (DOX) and Bortezomib (BTZ), which are chemo-drugs commonly used to treat various forms of cancers, such as multiple myeloma and lymphoma. Proteasome inhibitors (bortezomib) and immunomodulators (Lenalidomide (LLD) and analogues) have been used effectively in treating newly diagnosed MM patients in combination with other chemodrugs, e.g., doxorubicin (DOX), dexamethasone (DEX) and melphalan. Studies indicate that angiogenesis also plays an important role in the cancer progression in localized MM and lymphoma. Anti-angiogenesis drugs, such as LLD and its analogues, have shown clinical activities in treating MM. Active tumoral angiogenesis leads to leaky blood vessel formation, which provides a great opportunity for MM or lymphoma-targeted drug delivery using NPs via the EPR effects. In line with these findings, liposomal doxorubicin has been approved to treat relapsed or refractory MM in combination with BZB. However, current combination treatments have side toxicity issues. MM remains rarely curable. New drugs and novel treatments are still needed for the intensive as well as the maintenance treatment of MM. The cell-adhesion-mediated drug resistance (CAM-DR) of MM cells in BM led to resistance to the first line anticancer drugs, such as DOX. Interestingly, studies showed that bortezomib (BZB) can overcome CAM-DR through down-regulation of VLA-4 expression in MM and enhance the effects of conventional anti-myeloma therapeutics. Better combination therapies with fewer side effects and higher efficacy using DOX or BZB, or both, are needed.

Over the last two decades, nanoparticle-mediated drug delivery systems have been demonstrated as effective methods for the targeted delivery of chemotherapeutic drugs, via enhanced permeability and retention (EPR) effects. Encapsulation of cytotoxic anticancer drugs inside a nanoparticle is able to decrease side toxicity and improve the life quality of patient. Various nanocarrier systems have been developed for single drug delivery. However, it has been challenging to encapsulate two drugs with the distinct chemical and physical properties into one nanocarrier, such as hydrophobic PTX and metallic CDDP or polar bortezomib and hydrophobic DOX. Recently, a few studies have reported the co-delivery of CDDP, or Platinum prodrug (Pt-IV) together with other hydrophobic chemodrugs, such as PTX, docetaxel, daunorubicin, and gambogic acid, etc., to improve anticancer effects. However, versatile nanocarriers are still needed to fine tune the drug loading ratio and control the drug release profiles to maximize the synergism of combination therapies, such as PTX and CDDP in combination for treating ovarian cancer.

More and more, targeted therapy has been applied with traditional chemotherapy to achieve synergism in cancer treatments. In addition, gene therapy has been tested in clinic to restore the protein function by knock-in or suppress a mutated protein via gene silencing technique to treat diseases. A very efficient approach is to deliver siRNA to silence the critical proteins related with multiple drug resistance in chemotherapy. Therefore, the combination of therapeutic genes and chemodrugs would achieve synergism in treating cancers. If these two types of drug molecules could be co-delivered to tumor cells selectively with the optimal dose ratio delivered on the right time schedule, the side effects would be reduced and the therapeutic outcome maximized. However, gene molecules are highly water soluble. Moreover, targeted therapeutics, such as tyrosine kinase inhibitor, protesome inhibitor and other targeted inhibitors and antimetabolite drugs, are generally very polar molecules while traditional cytotoxic chemodrugs are generally hydrophobic (e.g., taxanes, anthracycline, vinca alkaloid and camptothecin drugs). It is challenging to co-load a nanoparticle with two types of drug molecules having distinct chemical and physical properties, such as, for example, a hydrophobic with a hydrophilic drug or a hydrophobic with a metallic drug. In addition, the combination delivery of anticancer drugs and gene molecules is a promising strategy to overcome multiple drug resistance. The gene molecules to be delivered could be plasmid DNA molecules for cell transfection of tumor suppressor proteins (e.g., P53, PTEN, etc., or siRNA) to knock down curtain transmembrane efflux protein, or another oncoprotein, such as ABCB1, MDR1, etc., to sensitize cancer cells to chemotherapy. However, the co-delivery of highly negatively charged gene molecules with a given chemodrug having its own distinct physicchemical properties is still challenging. A novel functionalized and spatially segregated nanocarrier is needed to refine the loading properties of different drug molecules within one depot. Once developed, these nanocarriers could be applied in the co-delivery of a broader range of gene molecules, hydrophilic, amphiphilic, metal-containing, and hydrophobic drug molecules.

SUMMARY OF THE DISCLOSURE

In an aspect, the present disclosure provides telodendrimers. In an embodiment, the telodendrimer is a compound of formula (I),

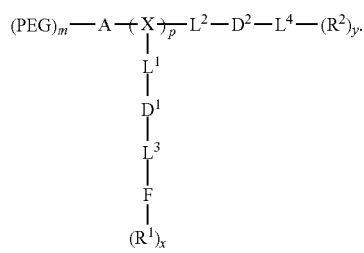

PEG is optionally present and is a polyethylene glycol moiety. PEG has a molecular weight of 44 Da to 100 kDa.

A is optionally present and is a monomer or oligomer. X is a branched monomer unit. Each $L^1$ is independently optional and is a linker group. Each $L^2$ is independently optional and is a linker group. Each $L^3$ is independently optional and is a linker group. Each $L^4$ is independently optional and is a linker group. $D^1$ is optional and is a dendritic polymer moiety having one or more branched monomer units (X), a plurality of end groups, and optionally, one or more linker groups $L^1$ and/or $L^3$. Each linker group is independently optional or a linker group linked to the focal point group of the dendritic polymer and monomer unit (X). F is a functional reactive moiety selected for specific drug conjugation/complexation via labile bonds, reversible complexes or charge interactions. $R^1$ are the end groups of the dendritic polymer and are independently at each occurrence in the compound selected from the group consisting of a catechol, a boronic acid, a carboxylic acid, an acylhydrazine, a hydroxyl, an amine, a thiol and a ketone for labile bond formation; or a positively charged moiety (e.g., primary, secondary, and tertiary amines for gene delivery or chelating groups, e.g., amines, aromatic imines and carboxylic acid, and thiol group for metallic drug chelation). $D^2$ is a dendritic polymer having one or more branched monomer units (X), a plurality of end groups, and optionally, one or more linker groups $L^2$ and/or $L^4$. Each linker group is independently optional or a linker group linked to the focal point group of the dendritic polymer and monomer unit (X). Each $R^2$ are the end groups of the dendritic polymer and are independently at each occurrence in the compound selected from the group consisting of a hydrophobic group, a hydrophilic group, an amphiphilic group, a reversible photocrosslinking group, and a drug ($R^2$ can comprise two different end groups, where one half of the $R^2$ end groups are one of said group and one half of the $R^2$ end groups are a second of said group). Subscript x is an integer from 1 to 64. Subscript y is an integer from 2 to 64. Subscript p is an integer from 1 to 32. Subscript m is an integer from 0 to 32.

In an embodiment, at each occurrence in a compound of formula (I) the branched monomer unit (X) is independently selected from the group consisting of a diamino carboxylic acid moiety, a dihydroxy carboxylic acid moiety, and a hydroxyl amino carboxylic acid moiety. In an embodiment, at each occurrence in the compound the diamino carboxylic acid is independently selected from the group consisting of 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid, and 5-amino-2-(3-aminopropyl) pentanoic acid. In an embodiment, the diamino carboxylic acid moiety is an amino acid moiety. In an embodiment, each branched monomer unit X is lysine moiety.

In an embodiment, a compound of formula (I) is selected from the group consisting of:

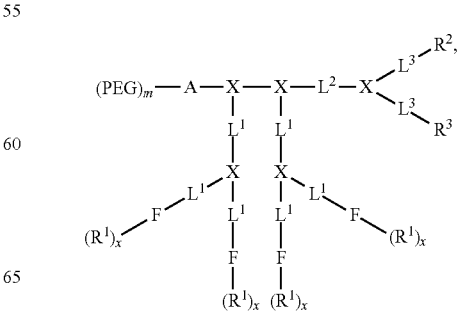

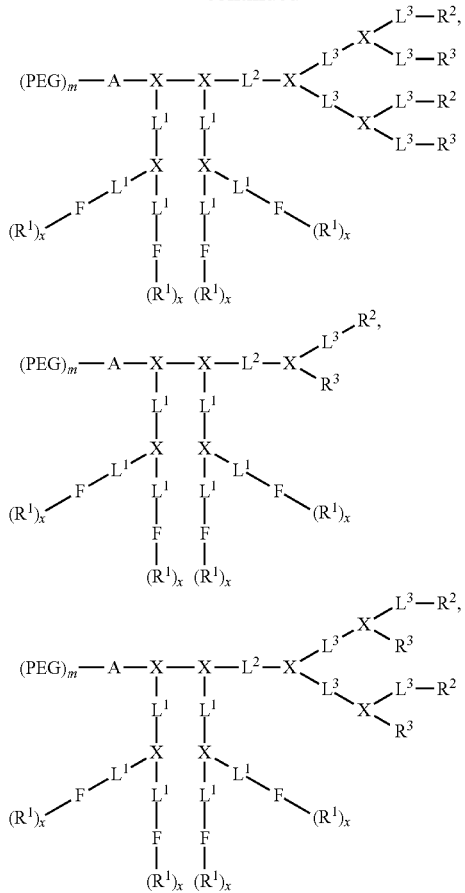

where each branched monomer unit is lysine moiety and $R^3$ is selected from the alternatives for $R^2$ described herein.

In an embodiment, each $R^2$ and $R^3$, if present in a compound of formula (I), is independently selected from a rhein moiety or derivative or analog thereof, cholic acid moiety or derivative or analog thereof, cholesterol moiety or derivative or analog thereof, coumarin moiety or derivative or analog thereof, curcumin moiety or derivative or analog thereof, flavin moiety or derivative or analog thereof, isoflavin moiety or derivative or analog thereof, riboflavin moiety or derivative or analog thereof, retinol moiety or derivative or analog thereof, retinoic acid moiety or derivative or analog thereof, chlorogenic acid moiety or derivative or analog thereof, anthraquinone moiety or derivative or analog thereof, xanthenone moiety or derivative or analog thereof, Vitamin E moiety or derivative or analog thereof, D-α-tocopherol succinate moiety or derivative or analog thereof, vitamins, lipids, fatty acids, bile acids, naturally-isolated compound moieties, and drugs.

In an embodiment, at each occurrence in a compound of formula (I) the linker $L^1$, $L^2$, and $L^3$ each are independently selected from the group consisting of a polyethylene glycol moiety, polyserine moiety, enzyme cleavable peptide moiety, disulfide bond moiety and acid labile moiety, polyglycine moiety, poly(serine-glycine) moiety, aliphatic amino acid moieties, 6-amino hexanoic acid moiety, 5-amino pentanoic acid moiety, 4-amino butanoic acid moiety, and beta-alanine moiety. In an embodiment, at each occurrence in a compound of formula (I) the linker $L^1$, $L^2$, and $L^3$ are independently selected from the group consisting of:

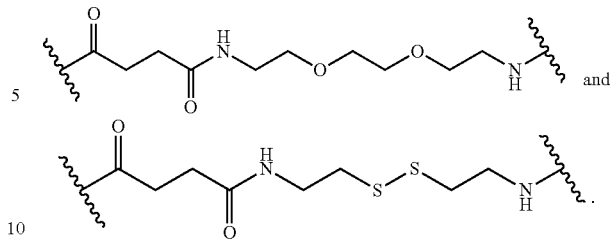

In an embodiment, the linker $L^1$, $L^2$, $L^3$, or a combination thereof comprises a cleavable group. In an embodiment, the cleavable group is a disulfide cleavable moiety.

In an embodiment, the $(PEG)_m$-A- portion of a compound of formula (I) is selected from the group consisting of:

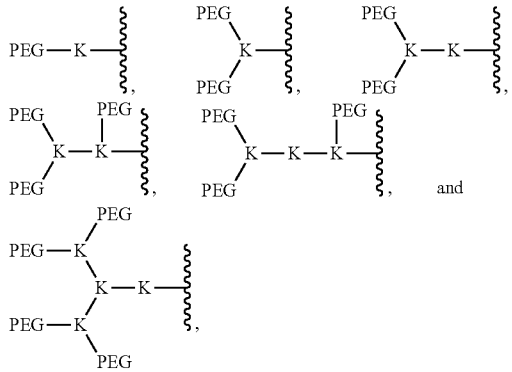

where each K is lysine.

In an embodiment, each $R^2$ and/or each $R^3$, if present in a compound of formula (I), is a reversible photocrosslinking group. In an embodiment, the reversible photocrosslinking group is coumarin moiety, 4-methylcoumarin moiety, cinnamic acid moiety or derivative or analog thereof, chlorogenic acid moiety or derivative or analog thereof, or a combination thereof.

In an embodiment, the telodendrimer is a compound of formula (II):

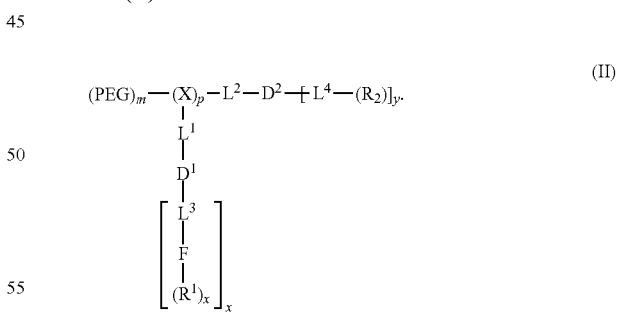

PEG is optionally present and is a polyethylene glycol moiety and PEG has a molecular weight of 44 Da to 100 kDa. X is optionally present and is a branched monomer unit. Each $L^1$ is independently optional and is a linker group. $L^2$ is independently optional and is a linker group; each $L^3$ is independently optional and is a linker group. Each $L^4$ is independently optional and is a linker group. $D^1$ is optional and is a dendritic polymer moiety having one or more branched monomer units (X), and a plurality of end groups. $D^2$ is a dendritic polymer having one or more branched monomer units (X), and a plurality of end groups. F is a functional reactive moiety selected for specific drug conjugation/complexation via labile bonds, reversible complexes or charge interactions. $R^1$ is an end group of the dendritic polymer and is independently at each occurrence in the compound selected from the group consisting of catechols, a boronic acids, carboxylic acids, acylhydrazines, hydroxyl, amines, thiols and ketones for labile bond formation; a positively charged moiety (e.g., primary, secondary or tertiary amines for gene delivery), chelating groups (e.g., amines, aromatic imines, and carboxylic acids), and thiol groups for metallic drug chelation). Each $R^2$ is an end group of the dendritic polymer and is independently at each occurrence in the compound selected from the group consisting of a hydrophobic group, a hydrophilic group, an amphiphilic group, a reversible photocrosslinking group, and a drug ($R^2$ can comprise two different end groups, where one half of the $R^2$ end groups are one of said group and one half of the $R^2$ end groups are a second of said group). Subscript x is an integer from 1 to 64. Subscript y is an integer from 1 to 64. Subscript p is an integer from 1 to 32. Subscript m is an integer from 0 to 32.

In an embodiment, at each occurrence in a compound of formula (II) the branched monomer unit (X) is independently selected from the group consisting of a diamino carboxylic acid moiety, a dihydroxy carboxylic acid moiety, and a hydroxyl amino carboxylic acid moiety. In an embodiment, at each occurrence in the compound the diamino carboxylic acid is independently selected from the group consisting of 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid, and 5-amino-2-(3-aminopropyl) pentanoic acid. In an embodiment, the diamino carboxylic acid moiety is an amino acid moiety. In an embodiment, each branched monomer unit X is lysine moiety.

In an embodiment, a compound of formula (II) is selected from the group consisting of:

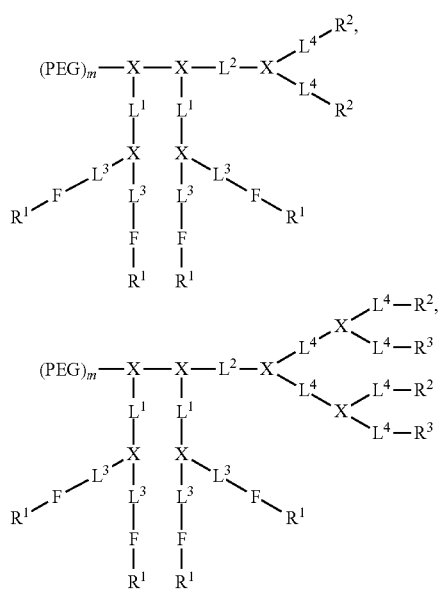

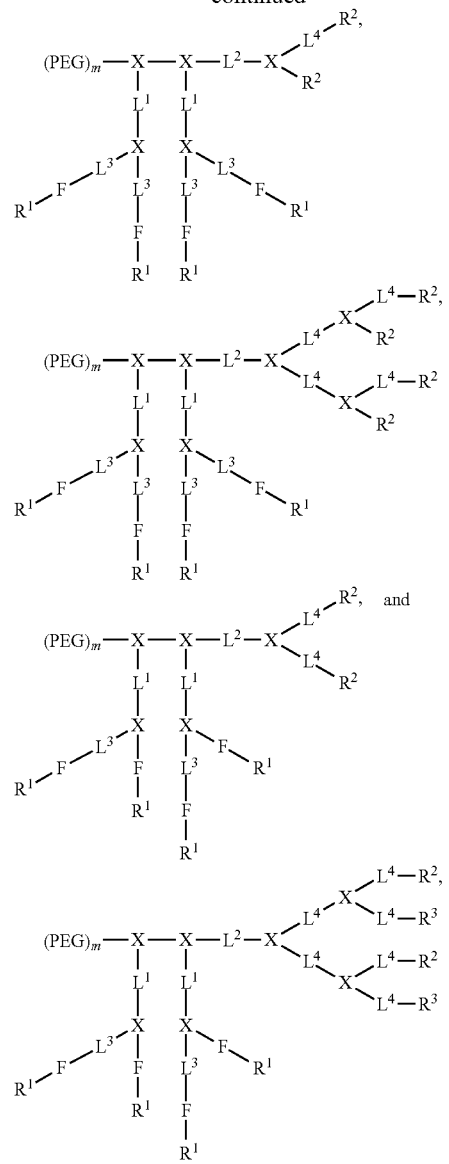

where each branched monomer unit is lysine moiety and $R^3$ is selected from the alternatives for $R^2$ described herein. In an embodiment, each $R^2$ and $R^3$, if present in a compound of formula (II), is independently selected from a rhein moiety or derivative or analog thereof, cholic acid moiety or derivative or analog thereof, cholesterol moiety or derivative or analog thereof, coumarin moiety or derivative or analog thereof, curcumin moiety or derivative or analog thereof, flavin moiety or derivative or analog thereof, isoflavin moiety or derivative or analog thereof, riboflavin moiety or derivative or analog thereof, retinol moiety or derivative or analog thereof, retinoic acid moiety or derivative or analog thereof, chlorogenic acid moiety or derivative or analog thereof, anthraquinone moiety or derivative or analog thereof, xanthenone moiety or derivative or analog thereof, Vitamin E moiety or derivative or analog thereof, D-α-tocopherol succinate moiety or derivative or analog thereof, vitamins, lipids, fatty acids, bile acids, naturally-isolated compound moieties, and drugs.

In an embodiment, at each occurrence in a compound of formula (II) the linker $L^1$, $L^2$, and $L^3$ each are independently selected from the group consisting of a polyethylene glycol moiety, polyserine moiety, enzyme cleavable peptide moiety, disulfide bond moiety and acid labile moiety, polyglycine moiety, poly(serine-glycine) moiety, aliphatic amino acid moieties, 6-amino hexanoic acid moiety, 5-amino pentanoic acid moiety, 4-amino butanoic acid moiety, and beta-alanine moiety. In an embodiment, at each occurrence in the compound the linker $L^1$, $L^2$, and $L^3$ are independently selected from the group consisting of:

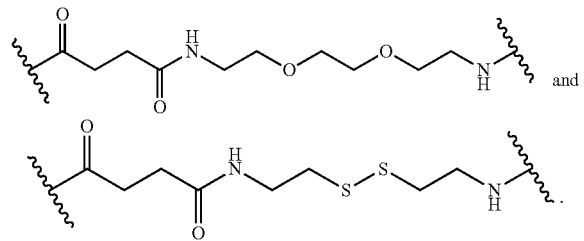

In an embodiment, the linker $L^1$, $L^2$, $L^3$, or a combination thereof comprises a cleavable group. In an embodiment, the cleavable group is a disulfide cleavable moiety.

In an embodiment, the $(PEG)_m$-A- portion of a compound of formula (II) is selected from the group consisting of:

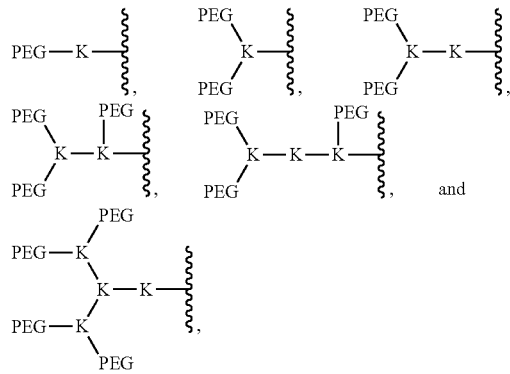

where each K is lysine. In an embodiment, each $R^2$ and/or each $R^3$, if present in a compound of formula (II), is a reversible photocrosslinking group. In an embodiment, the reversible photocrosslinking group is coumarin moiety, 4-methylcoumarin moiety, cinnamic acid moiety or derivative or analog thereof, chlorogenic acid moiety or derivative or analog thereof, or a combination thereof.

In an aspect, the present disclosure provides nanocarriers comprising the telodendrimers. In an embodiment, a nanocarrier comprises a plurality of compounds disclosed herein. In an embodiment, the nanocarrier further comprises a hydrophobic drug and/or a non-hydrophobic drug, and, optionally, an imaging agent.

DESCRIPTION OF THE DRAWINGS

For a fuller understanding of the nature and objects of the disclosure, reference should be made to the following detailed description taken in conjunction with the accompanying figures:

FIGS. 8B and 8C share the same legends with FIG. 8A. (: p<0.01; *: p<0.001).

FIG. 20. Examples of combination chemotherapies.

DETAILED DESCRIPTION OF THE DISCLOSURE

A functionalized and spatially segregated nanocarrier system was developed. The nanocarrier system can be used to deliver one or more therapeutic agents (e.g., drugs). In an embodiment, the nanocarrier system is used to co-deliver hydrophilic drug and hydrophobic drug molecules, amphiphilic and hydrophobic drug molecules, or polar drug and hydrophobic drug molecules. The nanocarrier system may also be used to deliver one or more therapeutic agents (e.g., drugs) and non-therapeutic agent chemical compounds (e.g., imaging agents). In an embodiment, the nanocarrier system is used to deliver one or more therapeutic agents (e.g., drugs) and non-therapeutic agent chemical compounds (e.g., imaging agents).

Figure 1:
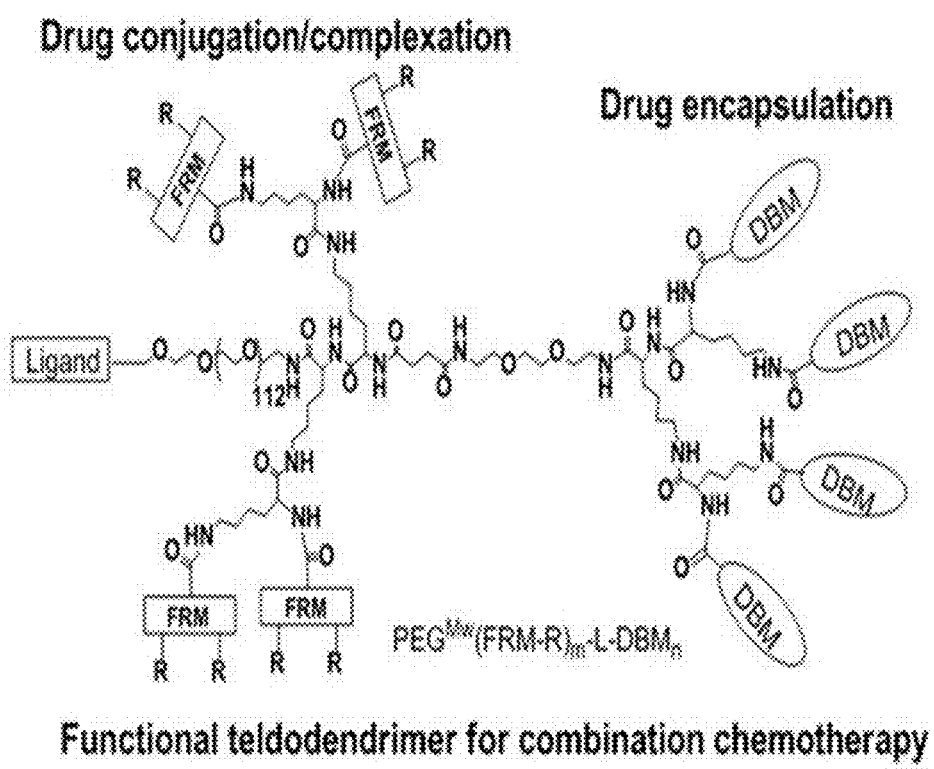
FIG. 1. Example of a functional telodendrimer for combination chemotherapy.

The three-layered telodendrimer shown in FIG. 1 illustrates a telodendrimer design that can be used, e.g., for the co-delivery of hydrophilic drug and hydrophobic drug molecules, amphiphilic drug and hydrophobic drug molecules, nucleotide drug and hydrophobic drug molecules, and polar drug and hydrophobic drug molecules. The various length of polyethylene glycol (ligand layer) serves as hydrophilic segments of the telodendrimer; the adjacent layer was composed of branched architecture capped with functional groups for the conjugation of specific drugs or gene molecules via labile linkages, reversible complexes or multivalent charge interactions (Drug conjugation/complexation or adjacent layer); the peripheral of the proximal dendrimer were specifically decorated with drug binding moieties for hydrophobic drug loading via physical encapsulation and/or affinity (Drug encapsulation or hydrophobic layer or end).

Three layered linear-dendritic telodendrimer micelles (TMs) were created by adding functional reactive moieties (FRMs) and reactive groups (Rs) to the intermediate layer (drug conjugation/complexation) of the telodendrimers forming the TMs to which drug and prodrug compounds can be conjugated.

The FRMs may be selected for specific drug conjugation/complexation via labile bonds, reversible complexes, or charge interactions. The reactive groups (Rs) can include: catechols, boronic acids, carboxylic acids, acylhydrazines, hydroxyl, amines, thiols, ketones, etc. for labile bond formation; positively charged moieties, e.g., primary, secondary or tertiary amines for gene delivery; chelating groups, e.g., amines, aromatic imines, and carboxylic acids; and thiol groups for metallic drug chelation. Any appropriate therapeutic compound, drug and prodrug can be conjugated to the intermediate layer, including DNA, RNA, SiRNA, peptide, doxorubicin, tyrosine kinase inhibitors, hydrophilic targeted inhibitors, botezomib, antimetabolite drugs, DNA alkylating reagents, cisplatin, oxaliplatin, etc. Nontherapeutic compounds may be conjugated to the intermediate layer.

The drug encapsulation layer of the telodendrimer has drug binding moieties (DBM), which could be identified via molecular docking technique, for specific hydrophobic drug encapsulation in the core of a micelle nanoparticle formed of multiple telodendrimers. The DBM can include Rhein, riboflavin, porphyrin coumarin for doxorubicin, daunorubicin, etc.; cholic acid, lithocholic acid, cholesterol, for paclitaxel, docetaxel, etc.; Vitamin E, lipid acids for Gambogic acid, oridonin and demethylcantharidine; coumarin and porphyrin for SN38 and curcumin; etc.

The telodendrimers comprise multiple segments (e.g., linear hydrophilic polymer segments, adjacent branched functional segments, interior dendritic drug-binding segments). The telodendrimers can form nanocarriers (e.g., three-layer telodendrimer micelle structures). As used herein the term "layer" when used in reference to the telodendrimers refers to the corresponding segment in the telodendrimer that corresponds to that layer in the nanocarrier.

Definitions. As used herein, the term "telodendrimer" refers to a linear-dendritic copolymer comprised of a hydrophobic segment and hydrophobic segment, comprising an optional hydrophilic segment (i.e., PEG moiety) and one or more chemical moieties covalently bonded to one or more end groups of the dendron. Suitable moieties include, but are not limited to, hydrophobic groups, hydrophilic groups, amphiphilic compounds, and drugs. Different moieties may be selectively installed at selected end groups using orthogonal protecting group strategies. Three-layer telodendrimers are telodendrimers which contain an intermediate segment between the hydrophilic segment and the hydrophobic segment.

As used herein, the term "moiety" refers to a part (substructure) or functional group of a molecule that is part of the telodendrimer structure. For example,

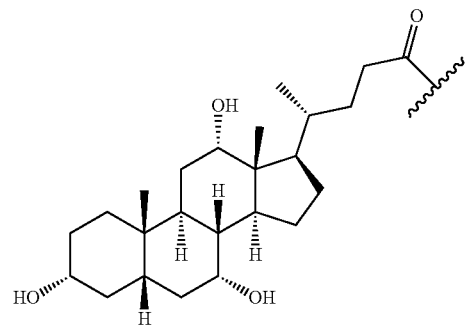

refers to a cholic acid moiety,

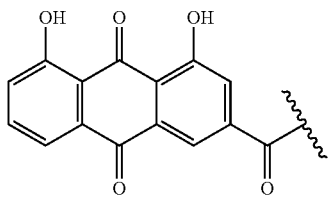 [SMILES: *C(=O)c1cc(O)c2c(c1)C(=O)c1cccc(O)c1C2=O]

refers to a rhein moiety,

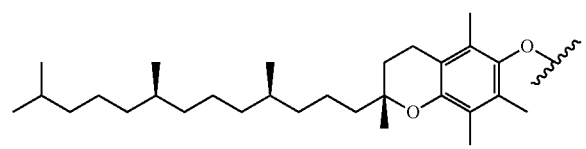 [SMILES: *Oc1c(C)c(C)c2c(c1C)CC[C@@](C)(CCC[C@H](C)CCC[C@H](C)CCCC(C)C)O2]

refers to a Vitamin E moiety.

As used herein, the terms "dendritic polymer" refer to branched polymers containing a focal point, a plurality of branched monomer units, and a plurality of end groups. The monomers are linked together to form arms (or "dendritic polymer") extending from the focal point and terminating at the end groups. The focal point of the dendritic polymer can be attached to other segments of the compounds of the disclosure, and the end groups may be further functionalized with additional chemical moieties.

As used herein, the term "nanocarrier" refers to a micelle resulting from aggregation of telodendrimer conjugates of the present disclosure. The nanocarrier has a hydrophobic core and a hydrophilic exterior. A nanocarrier resulting from the aggregation of three-layered telodendrimers have an intermediate layer.

As used herein, the terms "monomer" and "monomer unit" refer to a diamino carboxylic acid, a dihydroxy carboxylic acid, or a hydroxyl amino carboxylic acid. Examples of diamino carboxylic acid groups of the present disclosure include, but are not limited to, 2,3-diamino propanoic acid, 2,4-diaminobutanoic acid, 2,5-diaminopentanoic acid (ornithine), 2,6-diaminohexanoic acid (lysine), (2-aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid. Examples of dihydroxy carboxylic acid groups of the present disclosure include, but are not limited to, glyceric acid, 2,4-dihydroxybutyric acid, glyceric acid, 2,4-dihydroxybutyric acid, 2,2-bis(hydroxymethyl)propionic acid, and 2,2-bis(hydroxymethyl)butyric acid. Examples of hydroxyl amino carboxylic acids include, but are not limited to, serine and homoserine. One of skill in the art will appreciate that other monomer units can be used in the present disclosure. Monomers of the present invention can have a bond connectivity of, for example,

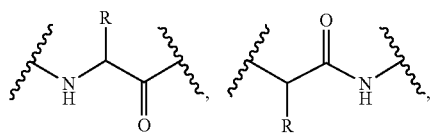

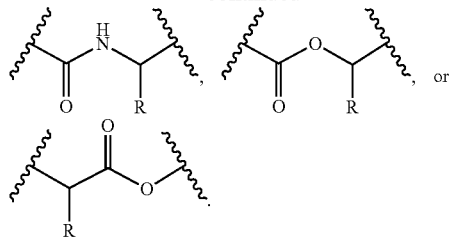

For example, when a monomer is defined as a lysine moiety, with a bond connectivity of A-Lys-B, where A and B are generic appendages, then it can be assumed that the structure can be any one of the following:

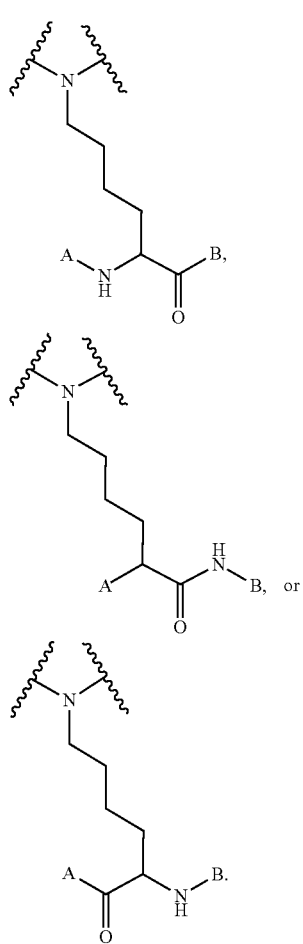

The monomer units can be substituted. For example, the monomer unit is a substituted lysine moiety.

As used herein, the term "linker" refers to a chemical moiety that links (e.g., via covalent bonds) one segment of a dendritic conjugate to another segment of the dendritic conjugate. The types of bonds used to link the linker to the segments of the telodendrimers include, but are not limited to, amides, amines, esters, carbamates, ureas, thioethers, thiocarbamates, thiocarbonate, and thioureas. For example, the linker (L, $L^1$, $L^2$, $L^3$, and/or $L^4$), individually at each occurrence in the telodendrimer, can be a polyethylene glycol moiety, polyserine moiety, polyglycine moiety, poly (serine-glycine) moiety, aliphatic amino acid moieties, 6-amino hexanoic acid moiety, 5-amino pentanoic acid moiety, 4-amino butanoic acid moiety, and beta-alanine moiety. The linker can also be a cleavable linker. In certain embodiments, combinations of linkers can be used. For example, the linker can be an enzyme cleavable peptide moiety, disulfide bond moiety or an acid labile moiety. One of skill in the art will appreciate that other types of bonds can be used in the present disclosure. In certain embodiments, the linker L, $L^1$, $L^2$, $L^3$, and/or $L^4$ can be

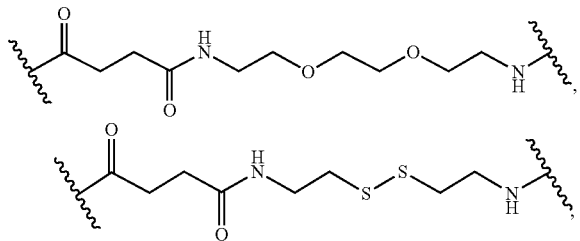

or a combination thereof, or other peptide sequence or spacer molecules.

As used herein, PEG group refers to polyethylene glycol. For example, the structure of PEG is

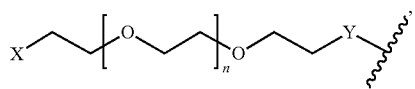

where X is selected from the group consisting of —NH$_2$, —OH, —SH, —COOH, —OMe, —N$_3$, —C≡CH$_2$, or —≡CH, Y is selected from the group consisting of a direct covalent bond, —C(=O)O—, —OC(=O)—, —OC(=O)NH—, —NHC(=O)—, —NHC(=O)O—, —NH—, —O—, —S—,

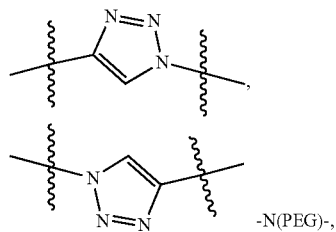

-N(PEG)-,

—NHCOLys(PEG)-, —NHCO[branched Lys(PEG)]$_n$NH—, -Lys-, -Lys(PEG)-, -Lys(PEG)-Lys, -Lys(PEG)-Lys(PEG)-, Lys(PEG-Lys-Lys(PEG), and -Lys(PEG)-Lys(Lys(PEG)$_2$)-Lys- and n is the number of repeating unit in a range of 1 to 72736.

As used herein, the term "reversible photocrosslinking group" refers to a chemical moiety that can be reversible reacted with another chemical moiety that will crosslink and decrosslink when exposed to certain conditions (e.g., UV light of varying wavelength). For example, a coumarin derivative moiety, can be photocrosslinked at >300 nm and decrosslinked at ~265 nm. The degree of crosslinking can be controlled by the amount of time the reversible photocrosslinkable groups are exposed to UV light.

As used herein, the term "oligomer" refers to fifteen or fewer monomers, as described above, covalently linked together. The monomers may be linked together in a linear or branched fashion. The oligomer may function as a focal point for a branched segment of a telodendrimer.

As used herein, the term "hydrophobic group" refers to a chemical moiety that is water-insoluble or repelled by water. Examples of hydrophobic groups include, but are not limited to, long-chain alkanes and fatty acids, fluorocarbons, silicones, certain steroids such as, for example, cholesterol, and certain polymers such as, for example, polystyrene and polyisoprene.

As used herein, the term "hydrophilic group" refers to a chemical moiety that is water-soluble or attracted to water. Examples of hydrophilic groups include, but are not limited to, alcohols, short-chain carboxylic acids, quaternary amines, sulfonates, phosphates, sugars, and certain polymers such as, for example, PEG.

As used herein, the term "amphiphilic compound" refers to a compound having both hydrophobic portions and hydrophilic portions. For example, the amphiphilic compounds of the present disclosure can have one hydrophilic face of the compound and one hydrophobic face of the compound.

As used herein, the term "polar compound" refers to a compound having a non-zero vector sum of its bond dipoles.

As used herein, the terms "drug" or "therapeutic agent" refers to an agent capable of treating and/or ameliorating a condition or disease. A drug may be a hydrophobic drug, which is any drug that repels water. Hydrophobic drugs useful in the present disclosure include, but are not limited to, paclitaxel, doxorubicin, etoposide, irinotecan, SN-38, cyclosporin A, podophyllotoxin, Carmustine, Amphotericin (Amphotericin B), Ixabepilone, Patupilone (epothelone class), rapamycin, bortezomib, gambogic acid, oridonin, norcantharidin, triptolide, camptothecin, docetaxel, daunorubicin, VP 16, prednisone, methotrexate, dexamethasone, vincristine, vinblastine, temsirolimus, and platinum drugs (e.g., cisplatin, carboplatin, oxaplatin). The drugs of the present disclosure also include prodrug forms and drug-like compounds. One of skill in the art will appreciate that other drugs can be used in the present disclosure.

As used herein, the term "imaging agent" refers to chemicals that allow body organs, tissue or systems to be imaged. Exemplary imaging agents include, but are not limited to, paramagnetic agents, optical probes, and radionuclides.

As used herein, the terms "treat", "treating" and "treatment" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "subject" refers to animals such as mammals. Suitable examples of mammals include, but are not limited to, primates (e.g., humans), cows, sheep, goats, horses, dogs, cats, rabbits, rats, mice, and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). In sensitized cells, the therapeutically effective dose can often be lower than the conventional therapeutically effective dose for non-sensitized cells.

Telodendrimers. In an aspect, the present disclosure provides telodendrimers. The telodendrimers are functional segregated telodendrimers having, for example, two or three functional segments. In an embodiment, the functional segments are a hydrophilic segment, an intermediate segment, and a hydrophobic segment. The intermediate segment can contain functional reactive moieties and reactive groups. The telodendrimers may have one or more crosslinking groups (e.g., reversible photocrosslinking groups). In an embodiment, a plurality of crosslinking groups (e.g., reversible photocrosslinking groups) are crosslinked. In an embodiment, the telodendrimer is made by a method of the present disclosure.

The telodendrimers may have a PEG groups. Without intending to be bound by any particular theory, it is considered that the PEG layer serves as a stealth hydrophilic shell to stabilize the nanoparticle and to avoid systemic clearance by the reticuloendothelial system (RES); the intermediate layer contains for example, optional crosslinkable functional group(s), amphiphilic oligo-cholic acid, riboflavin, or chlorogenic acid and can further stabilize nanoparticle and cage drug molecules in the core of nanoparticle; the interior layer contains drug-binding building blocks, such as vitamins (α-tocopherol, riboflavin, folic acid, retinoic acid, etc.) functional lipids (ceramide), chemical extracts (rhein, coumarin, curcumin, etc.) from herbal medicine to increase the affinity to drug molecules.

In an aspect, the present disclosure provides telodendrimers that are functional and spatially segregated telodendrimers having, for example, two or three functional segments. The telodendrimers can have one or more crosslinking groups (e.g., reversible photocrosslinking groups) and one or more functional reactive moieties (FRM).

In an aspect, the telodendrimers are functional segregated telodendrimers having three functional segments. In an embodiment the disclosure provides a compound of formula (I):

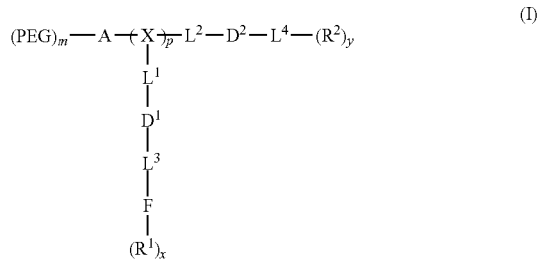

(I)

where PEG is optionally present and is a polyethylene glycol moiety, wherein PEG has a molecular weight of 44 Da to 100 kDa; A is a monomer or oligomer; X is a branched monomer unit; each $L^1$ is independently optional and is a linker group; each $L^2$ is independently optional and is a linker group; each $L^3$ is independently optional and is a linker group; each $L^4$ is independently optional and is a linker group; $D^1$ is optional and is a dendritic polymer moiety having one or more branched monomer units (X), a plurality of end groups, and optionally, one or more linker groups $L^1$, $L^3$; each linker group is independently optional or a linker group linked to the focal point group of the dendritic polymer and monomer unit (X); F is a functional reactive moiety selected for specific drug conjugation/complexation via labile bonds, reversible complexes or charge interactions; each $R^1$ is an end group of the dendritic polymer and is independently at each occurrence in the compound selected from the group consisting of catechols, a boronic acids, carboxylic acids, acylhydrazines, hydroxyl, amines, thiols and ketones for labile bond formation; a positively charged moiety (e.g., primary, secondary or tertiary amines for gene delivery); chelating groups (e.g., amines, aromatic imines, and carboxylic acids); and thiol groups for metallic drug chelation); $D^2$ is a dendritic polymer having one or more branched monomer units (X), a plurality of end groups, and optionally, one or more linker groups ($L^2$, $L^4$); each linker group is independently optional or a linker group linked to the focal point group of the dendritic polymer and monomer unit (X); each $R^2$ is an end group of the dendritic polymer and is independently at each occurrence in the compound selected from the group consisting of a hydrophobic group, a hydrophilic group, an amphiphilic group, a reversible photocrosslinking group, and a drug ($R^2$ can comprise two different end groups, where one half of the $R^2$ end groups are one of said group and one half of the $R^2$ end groups are a second of said group); subscript x is an integer from 1 to 64; subscript y is an integer from 2 to 64, subscript p is an integer from 1 to 32; and subscript m is an integer from 0 to 32. In formula (I), the branch of the telodendrimer comprising the (PEG)$_m$ moiety is the hydrophilic segment, the branch of the telodendrimer comprising the $L^1$ moiety is the intermediate segment, and the branch of the telodendrimer comprising the $L^2$ moiety is the hydrophobic segment. In an embodiment, A is optional.

In an embodiment the disclosure provides a compound of formula (II):

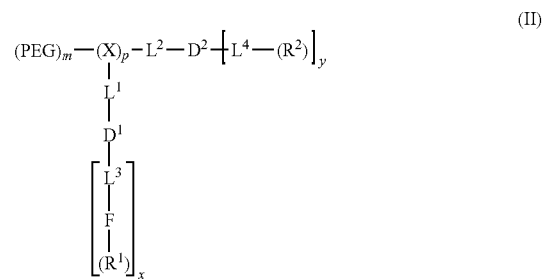

Figure 2:
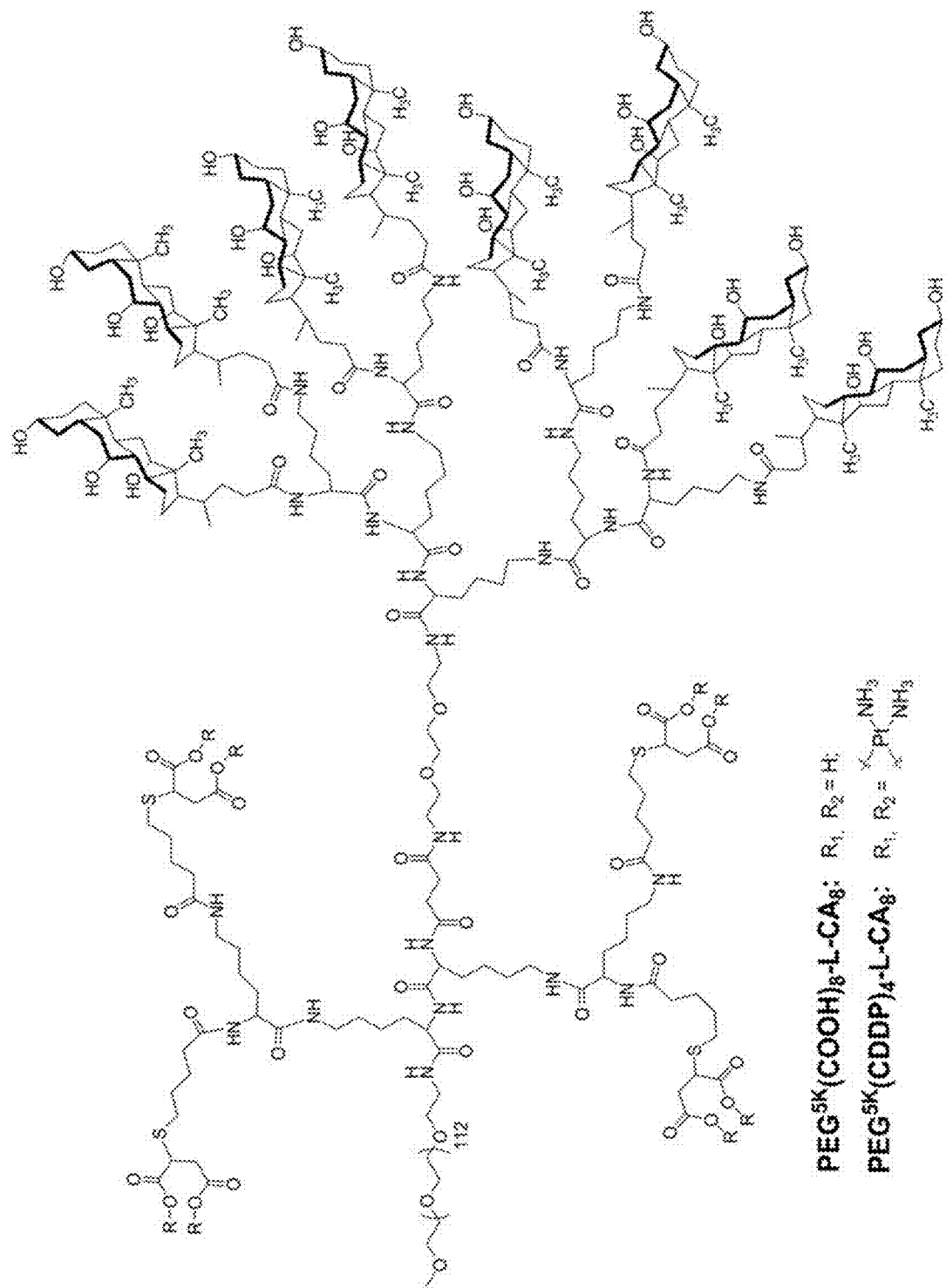
FIG. 2. The structure of telodendrimers $PEG^{5K}$$(COOH)_8$-L-$CA_8$ and $PEG^{5K}(CDDP)_4$-L-$CA_8$.

(II)

where PEG is optionally present and is a polyethylene glycol moiety, where PEG has a molecular weight of 44 Da to 100 kDa; X is optionally present and is a branched monomer unit; each $L^1$ is independently optional and is a linker group; each $L^2$ is independently optional and is a linker group; each $L^3$ is independently optional and is a linker group; each $L^4$ is independently optional and is a linker group; $D^1$ is optional and is a dendritic polymer moiety having one or more branched monomer units (X), and a plurality of end groups; $D^2$ is a dendritic polymer having one or more branched monomer units (X), and a plurality of end groups; F is a functional reactive moiety selected for specific drug conjugation/complexation via labile bonds, reversible complexes or charge interactions; $R^1$ is an end group of the dendritic polymer and is independently at each occurrence in the compound selected from the group consisting of catechols, a boronic acids, carboxylic acids, acylhydrazines, hydroxyl, amines, thiols and ketones for labile bond formation; a positively charged moiety (e.g., primary, secondary or tertiary amines for gene delivery); chelating groups (e.g., amines, aromatic imines, and carboxylic acids); and thiol groups for metallic drug chelation); each $R^2$ is an end group of the dendritic polymer and is independently at each occurrence in the compound selected from the group consisting of a hydrophobic group, a hydrophilic group, an amphiphilic group, a reversible photocrosslinking group, and a drug ($R^2$ can comprise two different end groups, where one half of the $R^2$ end groups are one of said group and one half of the $R^2$ end groups are a second of said group (e.g., $R^3$ groups); subscript x is an integer from 1 to 64, subscript y is an integer from 1 to 64, subscript p is an integer from 1 to 32; and subscript m is an integer from 0 to 32. Examples of functional telodendrimers having formula (II) are shown, for example, in FIG. 2.

In an embodiment, at each occurrence in the compound the branched monomer unit (X) in the compound of formula (I) is independently selected from the group consisting of a diamino carboxylic acid moiety, a dihydroxy carboxylic acid moiety, and a hydroxyl amino carboxylic acid moiety.

$R^2$ groups are end groups of the dendritic polymer and are independently at each occurrence in the compound selected from the group consisting of coumarin moiety or derivative or analog thereof, curcumin moiety or derivative or analog thereof, flavin moiety or derivative or analog thereof, isoflavin moiety or derivative or analog thereof, riboflavin moiety or derivative or analog thereof, retinol moiety or derivative or analog thereof, retinoic acid moiety or derivative or analog thereof, chlorogenic acid moiety or derivative or analog thereof; anthraquinone moiety or derivative or analog thereof, xanthenone moiety or derivative or analog thereof, Vitamin E moiety or derivative or analog thereof, and D-α-tocopherol succinate moiety or derivative or analog thereof, vitamins or derivative or analog thereof, lipids or derivative or analog thereof, fatty acids or derivative or analog thereof, bile acids or derivative or analog thereof, naturally-isolated compound moieties or derivative or analog thereof, and drugs or derivative or analog thereof. In an embodiment, subscript y is an integer from 2 to 64, including all integer values and ranges therebetween. In an embodiment, subscript y is equal to the number of end groups on the dendritic polymer. In an embodiment, at least half the number y of $R^2$ groups are each independently selected from the group consisting of coumarin moiety or derivative or analog thereof, curcumin moiety or derivative or analog thereof, flavin moiety or derivative or analog thereof, isoflavin moiety or derivative or analog thereof, riboflavin moiety or derivative or analog thereof, retinol moiety or derivative or analog thereof, retinoic acid moiety or derivative or analog thereof, chlorogenic acid moiety or derivative or analog thereof, anthraquinone moiety or derivative or analog thereof, xanthenone moiety or derivative or analog thereof, Vitamin E moiety or derivative or analog thereof, and D-α-tocopherol succinate moiety or derivative or analog thereof, vitamins or derivative or analog thereof, lipids or derivative or analog thereof, fatty acids or derivative or analog thereof, bile acids or derivative or analog thereof, naturally-isolated compound moieties or derivative or analog thereof, and drugs or derivative or analog thereof.

$R^1$ are end groups of the dendritic polymer and can include, for example: catechol, boronic acids, carboxylic acids, acylhydrazines, hydroxyl, amine, thiol and ketone for labile bond formation; or positively charged moieties, e.g., primary, secondary or tertiary amines for gene delivery; or chelating groups, e.g., amines, aromatic imines and carboxylic acid, and thiol group, for, e.g., metallic drug chelation. Any appropriate therapeutic compound, e.g., drugs and prodrugs, can be conjugated to the intermediate layer, including DNA, RNA, SiRNA, peptide, cisplatin, oxaliplatin, Botezomib, doxorubicin, hydrophilic targeted inhibitors, etc.

In various embodiments, the telodendrimer compound of the present disclosure has the following structure:

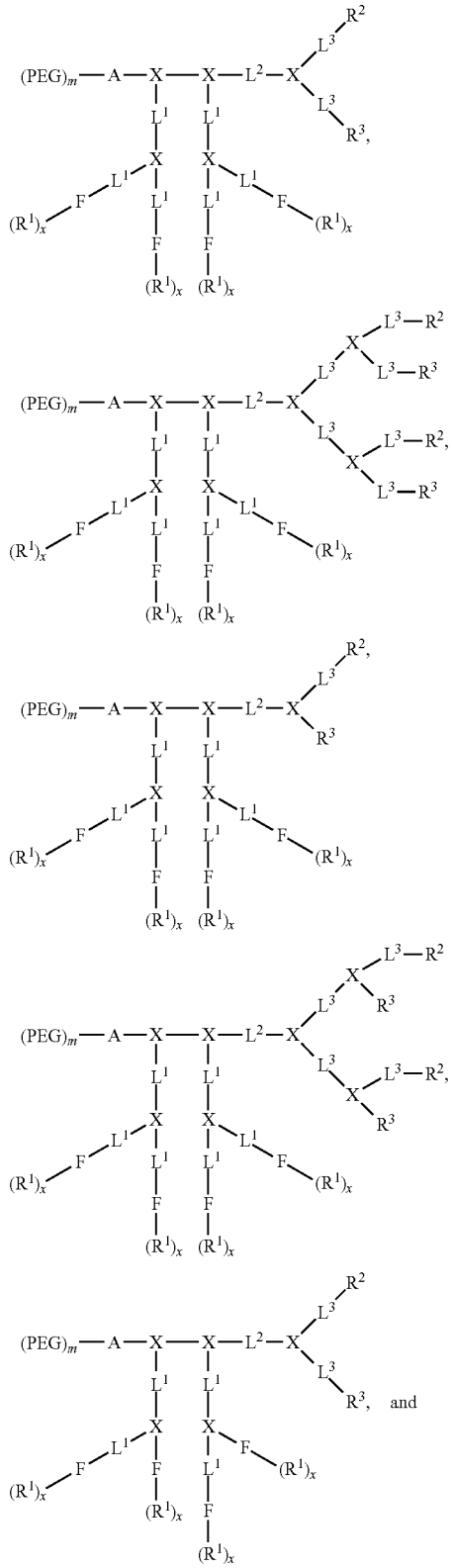

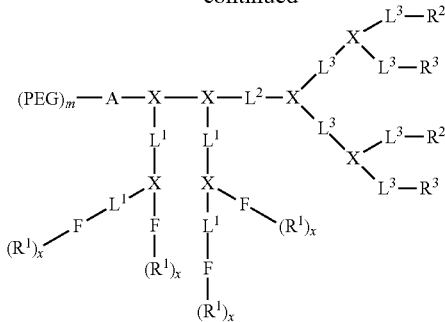

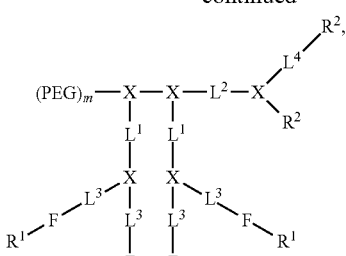

where each branched monomer unit may be a lysine moiety. In these structures, the arm of the telodendrimer comprising the $(PEG)_m$ moiety is the hydrophilic segment, the branch(es) of the telodendrimer comprising the $L^1$ moiety/moieties is/are the intermediate segment(s), and the branch(es) of the telodendrimer comprising the $L^2$ moiety/moieties is/are the hydrophobic segment. $R^2$ is as defined herein and $R^3$ is an end group of the dendritic polymer and is selected from the group consisting of coumarin moiety or derivative or analog thereof, curcumin moiety or derivative or analog thereof, flavin moiety or derivative or analog thereof, isoflavin moiety or derivative or analog thereof, riboflavin moiety or derivative or analog thereof, retinol moiety or derivative or analog thereof, retinoic acid moiety or derivative or analog thereof, chlorogenic acid moiety or derivative or analog thereof; anthraquinone moiety or derivative or analog thereof, xanthenone moiety or derivative or analog thereof, Vitamin E moiety or derivative or analog thereof, and D-α-tocopherol succinate moiety or derivative or analog thereof, vitamins or derivative or analog thereof, lipids or derivative or analog thereof, fatty acids or derivative or analog thereof, bile acids or derivative or analog thereof, naturally-isolated compound moieties or derivative or analog thereof, and drugs or derivative or analog thereof.

In various embodiments, the telodendrimer compound of the present disclosure has the following structure:

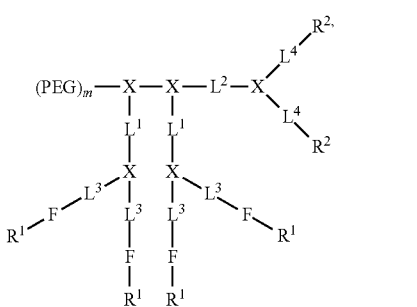

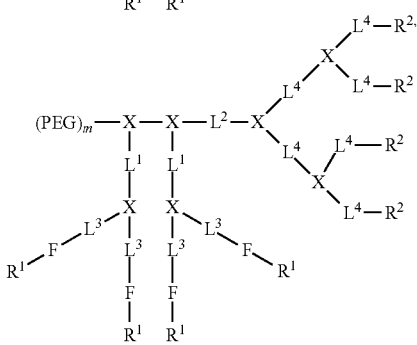

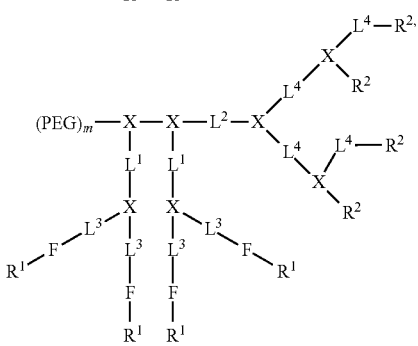

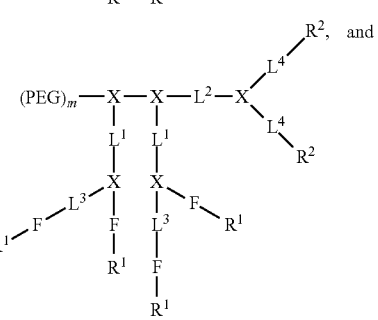

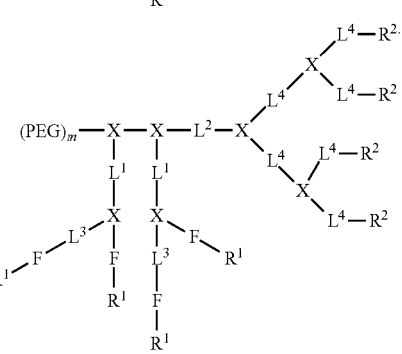

For example, each branched monomer unit is a lysine moiety.

In an embodiment, at each occurrence in the compound the linker $L^1$, $L^2$, and $L^3$ in the compound of formula (I) are independently at each occurrence selected from the group consisting of a polyethylene glycol moiety, polyserine moiety, enzyme cleavable peptide moiety, disulfide bond moiety, acid labile moiety, polyglycine moiety, poly(serine-glycine) moiety, aliphatic amino acid moieties, 6-amino hexanoic acid moiety, 5-amino pentanoic acid moiety, 4-amino butanoic acid moiety, and beta-alanine moiety. In an embodiment, at each occurrence in the compound the linker $L^1$, $L^2$, and $L^3$ are independently at each occurrence selected from the group consisting of:

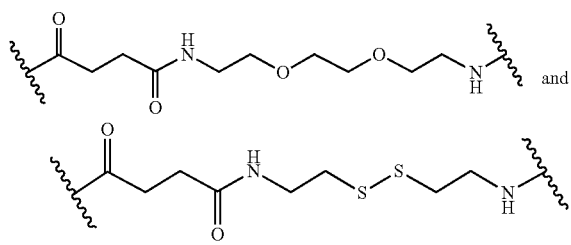

in the compound of formula (I). In an embodiment, the linker $L^1$, $L^2$, $L^3$, or a combination thereof comprises a cleavable group in the compound of formula (I). In an embodiment, the cleavable group is a disulfide cleavable moiety in the compound of formula (I).

In an embodiment, the $(PEG)_m$-A- portion of the compound is selected from the group consisting of:

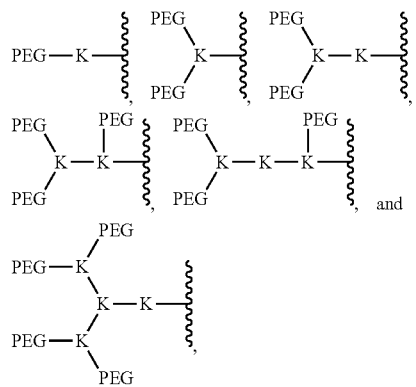

where each K is lysine in the compound of formula (I).

In an embodiment, each $R^2$ and $R^3$, if present, is independently selected from a rhein moiety or derivative or analog thereof, cholic acid moiety or derivative or analog thereof, moiety or derivative or analog thereof, coumarin moiety or derivative or analog thereof, curcumin moiety or derivative or analog thereof, flavin moiety or derivative or analog thereof, isoflavin moiety or derivative or analog thereof, riboflavin moiety or derivative or analog thereof, retinol moiety or derivative or analog thereof, retinoic acid moiety or derivative or analog thereof, chlorogenic acid moiety or derivative or analog thereof; anthraquinone moiety or derivative or analog thereof, xanthenone moiety or derivative or analog thereof, Vitamin E moiety or derivative or analog thereof, D-α-tocopherol succinate moiety or derivative or analog thereof, vitamins, lipids, fatty acids, bile acids, naturally-isolated compound moieties, and drugs, and combinations thereof in the compound of formula (I). In another embodiment, each $R^2$ and $R^3$, if present, is a reversible photocrosslinking group. For example, the reversible photocrosslinking group is coumarin moiety, 4-methylcoumarin moiety, cinnamic acid moiety, chlorogenic acid moiety or derivative or analog thereof, or a combination thereof. $R^2$ and $R^3$ can be the same.

In an embodiment, each F is a functional reactive moiety of a telodendrimer of the present invention with one or more (x) $R^1$ functional groups selected for specific drug conjugation/complexation via labile bonds, reversible complexes or charge interactions. In an embodiment, F may be a moiety of $R^1$. The reactive groups $R^1$ can include: catechol, boronic acids, carboxylic acids, acylhydrazines, hydroxyl, amine, thiol and ketone for labile bond formation; or positively charged moieties, e.g., primary, secondary or tertiary amines for gene delivery; or chelating groups, e.g., amines, aromatic imines and carboxylic acid, and thiol group for metallic drug chelation. $R^1$ can comprise more than one of such functional groups. Any appropriate therapeutic compound, drug and prodrug can be conjugated to the intermediate layer. Therapeutic agents such as, for example, hydrophilic therapeutic agents, hydrophobic therapeutic agents, amphiphilic therapeutic agents, polar therapeutic agents, non-polar therapeutic agents or combinations thereof can be conjugated to the intermediate layer. Examples of suitable therapeutic agents include DNA, RNA, SiRNA, peptide, cisplatin, oxaliplatin, Botezomib, doxorubicin, hydrophilic targeted inhibitors, etc. Examples of suitable therapeutic agents are disclosed herein.

In an embodiment, the telodendrimer comprises one or more therapeutic agents (e.g., drugs). In an embodiment, the telodendrimer comprises hydrophilic drug and hydrophobic drug molecules. In an embodiment, the telodendrimer has one drug (e.g., cisplatin) and the drug is in the segment that forms the intermediate layer of the telodendrimer micelle. The therapeutic agents (e.g., drugs) and/or non-therapeutic agent chemical compounds (e.g., imaging agents) are complexed and/or conjugated to the telodendrimer.

The drug conjugation/complexation described herein has the advantage of allowing the delivery by a single micelle nanoparticle of hydrophobic therapeutic compounds with non-hydrophobic therapeutic compounds, including hydrophilic and amphiphilic drug compounds, heavy metal-containing therapeutic compounds, and polynucleotide reagents. It also allows for nanoparticles to be designed to achieve differential dosing and release timing of the hydrophobic compound and the non-hydrophobic compound to achieve synergistic effects on tumors. Conjugation of the therapeutic compound to the telodendrimers comprising the nanoparticle reduces dissipation of the therapeutic compound from the nanoparticle into the blood stream, thereby reducing toxicities associated to the compound. Three-layer telodendrimer micelle nanoparticles were shown to be highly stable and preferentially targeting tumor sites, a high proportion of the drug conjugated/complexed to the intermediate layer is delivered to the tumor. One or more of the individual therapeutic agents in each combination therapy can be conjugated or complexed to the telodendrimers of the present invention. Examples of combination therapies (combinations of drugs) are provided in FIG. 20.

Examples of combination therapies (combinations of drugs) include: bleomycin and etoposide; carboplatin and methotrexate; carboplatin and etoposide; cisplatin and fluorouracil; cisplatin and topotecan; cisplatin and dexamethasone; cisplatin and cytarabine; dexamethasone and cytarabine; cisplatin, dexamethasone and cytarabine; docetaxel and carboplatin; epirubicin and cisplatin; epirubicin and fluorouracil; cisplatin and fluorouracil; epirubicin, cisplatin and fluorouracil; epirubicin and capecitabine; cisplatin and capecitabine; epirubicin, cisplatin and capecitabine; epirubicin and oxaliplatin; epirubicin and capecitabine; oxaliplatin and capecitabine; epirubicin, oxaliplatin and capecitabine; etoposide and cisplatin; methotrexate and mitoxantrone; oxaliplatin and capecitabine; paclitaxel and carboplatin; pemetrexed and cisplatin; vinorelbine and carboplatin; vinorelbine and cisplatin. Other combination therapies using two or more individual drugs in FIG. 20 or using individual or multiple drugs in FIG. 20 and drugs or other therapeutically useful compounds not in FIG. 20 are possible.

Nanocarriers. In an aspect, the present disclosure provides nanocarriers comprising the telodendrimers. In an embodiment, a composition comprises an aggregate of a plurality of the telodendrimers that form a nanocarrier having a hydrophobic core and a hydrophilic exterior. The nanocarriers may comprise teleodendrimers having a plurality of cross-linked groups (e.g., photo-cross-linked groups). In an embodiment, a composition comprises an aggregate of a plurality of the telodendrimers having a plurality of cross-linked groups (e.g., photo-cross-linked groups) that form a nanocarrier having a hydrophobic core and a hydrophilic exterior.

The nanocarrier may be a telodendrimer micelle. A telodendrimer micelle is a nanoconstruct formed by the self-assembly of the telodendrimer in aqueous solution. The telodendrimer micelle can serve as a nanocarrier to load various types of therapeutics.

Figure 21:
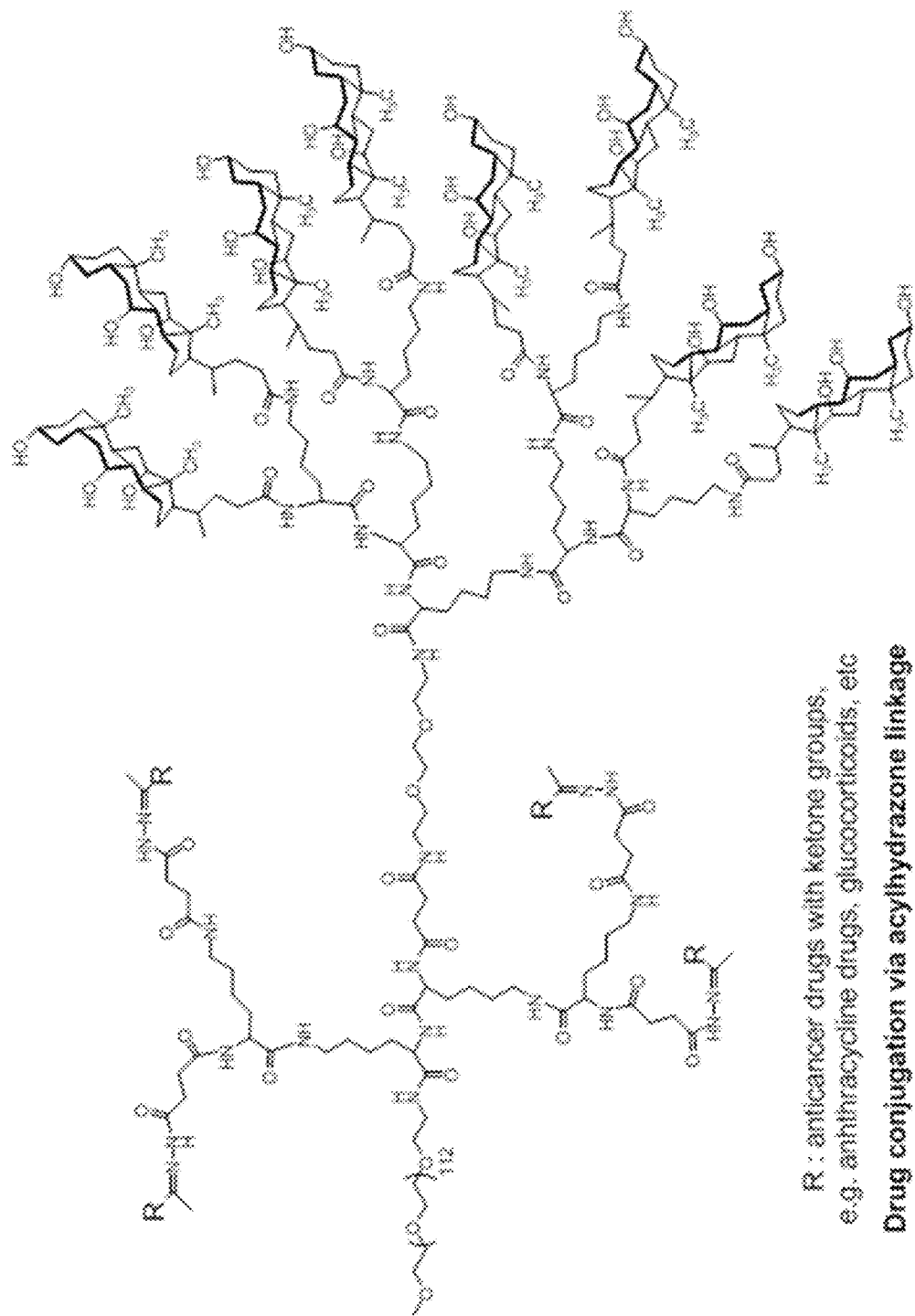
FIG. 21. Example of drug conjugation in the intermediate layer.

The nanocarriers (e.g., telodendrimer micelles) have a multiple layer (e.g., three-layer) structure comprising an intermediate layer. In an embodiment, the intermediate layer comprises one or more therapeutic agents or non-therapeutic agent chemical compounds (e.g., imaging agents). In an embodiment, the intermediate layer does not comprise one or more therapeutic agents or non-therapeutic agent chemical compounds (e.g., imaging agents). The therapeutic agents (e.g., drugs) and/or non-therapeutic agent chemical compounds (e.g., imaging agents) are complexed and/or conjugated (see, e.g., FIG. 21) to the intermediate layer. The intermediate layer can comprise therapeutic agents such as, for example, hydrophilic therapeutic agents, hydrophobic therapeutic agents, amphiphilic therapeutic agents, polar therapeutic agents, non-polar therapeutic agents, or combinations thereof. Examples of suitable therapeutic agents are disclosed herein.

The empty nanocarriers were examined to be nontoxic in cell culture and the drug-loaded nanoformulations exhibited the similar potency in killing cancer cells in vitro, and better anticancer effects in vivo, due to the tumor targeted drug delivery. The resulting nanocarriers exhibit superior drug loading capacity and stability. The side toxicities of the chemodrugs were significantly reduced via nanoformulation. The optimized nanoparticle is able to target delivery of the payload chemo drugs to the cancer site. As a result, custom designed telodendrimer nanotherapeutics significantly improve the anticancer effects in vivo.

The telodendrimers of the present disclosure can aggregate to form nanocarriers with a hydrophobic core, an intermediate layer (e.g., a functional reactive layer), and a hydrophilic exterior. In an embodiment, a plurality of telodendrimers aggregate to form nanocarriers with a hydrophobic core and a drug-conjugated intermediate layer and a hydrophilic exterior. In an embodiment, the disclosure provides a nanocarrier having an interior and an exterior, the nanocarrier comprising a plurality of the telodendrimer conjugates of the disclosure, wherein each compound self-assembles in an aqueous solvent to form the nanocarrier such that a hydrophobic pocket is formed in the interior of the nanocarrier, and wherein the hydrophilic segment (e.g., PEG) of each compound self-assembles on the exterior of the nanocarrier.

In an embodiment, the nanocarrier comprises a hydrophobic therapeutic agent (e.g., a hydrophobic drug) in the core and a therapeutic agent in the intermediate layer (e.g., a non-hydrophobic therapeutic agent). In an embodiment, the nanocarrier further comprises an imaging agent.

In some embodiments, the nanocarrier includes at least one monomer unit that is optionally linked to an optical probe, a radionuclide, a paramagnetic agent, a metal chelate or a drug. The drug can be a variety of hydrophilic or hydrophobic drugs, and is not limited to the hydrophobic therapeutic agents (e.g., a hydrophobic drugs) and non-hydrophobic therapeutic agents (e.g., a non-hydrophobic drugs) that are sequestered in the interior of the nanocarriers of the present disclosure.

The TMs can be designed such that each of the therapeutic agents carried will have a different release profile. Examples of conditions that can affect the release profile of carried therapeutic agents include time and biological environment.

The nanocarrier may comprise two or more different telodendrimer/drug constructs. Each of the two or more different telodendrimer polymers can each be designed for a different drug combinations (i.e., the affinity layer of each telodendrimer can be tuned to different drugs or different therapeutic agents can be conjugated to the intermediate layer of each telodendrimer.).

For example, each of the telodendrimers can be associated (e.g., sequestered) with drugs (e.g., a different drug combinations) in separate reactions. Subsequently, the two or more telodendrimer polymer/drug combinations can be combined under such conditions that they form micelles containing a mix of telodendrimer polymer/drug constructs. If, for example, the micelles contain 100 or so individual telodendrimers, it is expected that the "mixed" micelles will contain stochastic mix of the two or more drugs. The average composition will depend upon the ratio of the 2 or more telodendrimer polymer/drug constructs in the mixture. The "mixed" micelles can be used to deliver three or more drugs at the same time in a predetermined ratio (e.g., where the ratio is based on the relative starting amounts of the 3 or more drugs).

In the "mixed" micelle embodiment, it may be desirable that each telodendrimer have two different end groups ($R^1$ and $R^2$), where $R^1$ is tuned for drug complexation and $R^2$ is tuned to provide drug affinity to make the various polymer/drug combinations compatible (for example, rhein for DOX; cholic acid for PTX, coumarin for SN-38 loading).

Drugs that can be sequestered in the nanocarriers or linked to the conjugates of the present disclosure include, but are not limited to, cytostatic agents, cytotoxic agents (such as for example, but not limited to, DNA interactive agents (such as cisplatin or doxorubicin)); taxanes (e.g., taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methotrexate); alkylating agents (such as temozolomide (TEMODAR™ from Schering-Plough Corporation, Kenilworth, N.J.), cyclophosphamide); aromatase combinations; ara-C, adriamycin, cytoxan, and gemcitabine. Other drugs useful in the nanocarrier of the present disclosure include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine. Prodrug forms are also useful in the disclosure. Additional drugs are provided in FIG. 20.

Other drugs useful in the present disclosure also include radionuclides, such as $^{67}Cu$, $^{90}Y$, $^{123}I$, $^{125}I$, $^{131}I$, $^{177}Lu$, $^{188}Re$, $^{186}Re$ and $^{211}At$. In some embodiments, a radionuclide can act therapeutically as a drug and as an imaging agent.

Imaging agents include paramagnetic agents, optical probes and radionuclides. Paramagnetic agents include iron particles, such as iron nanoparticles that are sequestered in the hydrophobic pocket of the nanocarrier.

Some embodiments of the present disclosure provide nanocarriers wherein each amphiphilic compound $R^1$, $R^2$, is independently cholic acid, allocholic acid, pythocholic acid, avicholic acid, deoxycholic acid, or chenodeoxycholic acid.

In an aspect, the present disclosure provides methods of using the telodendrimers. The telodendrimers can be used, for example, in methods of treatment.

Method of treating. The nanocarriers of the present disclosure can be used to treat any disease requiring the administration of a drug, such as by sequestering a hydrophobic drug in the interior of the nanocarrier, or by covalent attachment of a drug to a conjugate of the nanocarrier. The nanocarriers can also be used for imaging, by sequestering an imaging agent in the interior of the nanocarrier, or by attaching the imaging agent to a conjugate of the nanocarrier. In an embodiment, compositions comprising the telodendrimers are used in a method for treating a disease.

In some embodiments, the present disclosure provides a method of treating a disease, including administering to a subject in need of such treatment a therapeutically effective amount of a nanocarrier of the present disclosure, where the nanocarrier includes at least two drugs. The drugs can be a covalently attached to a conjugate of the nanocarrier. In some embodiments, the drugs are a hydrophobic drug, sequestered in the interior of the nanocarrier. In some embodiments, the nanocarrier also includes an imaging agent. The imaging agent can be a covalently attached to a conjugate of the nanocarrier, or the imaging agent can be sequestered in the interior of the nanocarrier. In some other embodiments, both a hydrophobic drug and an imaging agent are sequestered in the interior of the nanocarrier. In still other embodiments, both a drug and an imaging agent are covalently linked to a conjugate or conjugates of the nanocarrier. In yet other embodiments, the nanocarrier can also include a radionuclide.

The nanocarriers of the present disclosure can be administered to a subject for treatment, e.g., of hyperproliferative disorders including cancer such as, but not limited to: carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, multiple myelomas, Hodgkin's lymphoma, and non-Hodgkin's lymphoma (see, CANCER: PRINCIPLES AND PRACTICE (DeVita, V. T. et al. eds 2008) for additional cancers).

Other diseases that can be treated by the nanocarriers of the present disclosure include: (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome).

In addition, the nanocarriers of the present disclosure are useful for the treatment of infection by pathogens such as viruses, bacteria, fungi, and parasites. Other diseases can be treated using the nanocarriers of the present disclosure.

Formulations. The nanocarriers of the present disclosure can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present disclosure (see, e.g., *Remington's Pharmaceutical Sciences*, $20^{th}$ ed., 2003, supra). Effective formulations include oral and nasal formulations, formulations for parenteral administration, and compositions formulated for with extended release.

Formulations suitable for oral administration can consist of (a) liquid solutions, such as an effective amount of a compound of the present disclosure suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The liquid solutions described above can be sterile solutions. The pharmaceutical forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the disclosure in a sustained release formulation.

Pharmaceutical preparations useful in the present disclosure also include extended-release formulations. In some embodiments, extended-release formulations useful in the present disclosure are described in U.S. Pat. No. 6,699,508, which can be prepared according to U.S. Pat. No. 7,125,567, both patents incorporated herein by reference.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

In practicing the methods of the present disclosure, the pharmaceutical compositions can be used alone, or in combination with other therapeutic or diagnostic agents.

Administration. The nanocarriers of the present disclosure can be administered as frequently as necessary, including hourly, daily, weekly or monthly. The compounds utilized in the pharmaceutical method of the disclosure are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present disclosure should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch or pump.

The pharmaceutical compositions can be administered to the patient in a variety of ways, including topically, parenterally, intravenously, intradermally, subcutaneously, intramuscularly, colonically, rectally or intraperitoneally. Preferably, the pharmaceutical compositions are administered parenterally, topically, intravenously, intramuscularly, subcutaneously, orally, or nasally, such as via inhalation.

In practicing the methods of the present disclosure, the pharmaceutical compositions can be used alone, or in combination with other therapeutic or diagnostic agents. The additional drugs used in the combination protocols of the present disclosure can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present disclosure, separately or at different times.

Method of imaging. In another embodiment, compositions comprising the telodendrimers are used in imaging methods. In some embodiments, the present disclosure provides a method of imaging, including administering to a subject to be imaged, an effective amount of a nanocarrier of the present disclosure, wherein the nanocarrier includes an imaging agent. In other embodiments, the method of treating and the method of imaging are accomplished simultaneously using a nanocarrier having a hydrophobic therapeutic agent, a non-hydrophobic therapeutic agent and an imaging agent.

Exemplary imaging agents include paramagnetic agents, optical probes, and radionuclides. Paramagnetic agents imaging agents that are magnetic under an externally applied field. Examples of paramagnetic agents include, but are not limited to, iron particles including nanoparticles. Optical probes are fluorescent compounds that can be detected by excitation at one wavelength of radiation and detection at a second, different, wavelength of radiation. Optical probes useful in the present disclosure include, but are not limited to, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo radioactive decay. Radionuclides useful in the present disclosure include, but are not limited to, $^{3}$H, $^{11}$C, $^{13}$N, $^{18}$F, $^{60}$Co, $^{64}$Cu, $^{67}$Cu, $^{68}$Ga, $^{82}$Rb, $^{90}$Sr, $^{90}$Y, $^{99}$Tc, $^{99m}$Tc, $^{111}$In, $^{123}$I, $^{124}$I, $^{125}$I, $^{29}$I, $^{131}$I, $^{137}$Cs, $^{177}$Lu, $^{186}$Re, $^{188}$Re, $^{211}$At, Rn, Ra, Th, U, Pu and $^{241}$Am.

The following examples are presented to illustrate the present disclosure. They are not intended to limiting in any manner.

EXAMPLE 1

This example describes the co-delivery of paclitaxel and cisplatin using telodendrimers of the present disclosure.

Summary of PTX/CDDP co-delivery via nanoparticle. The co-delivery of low dosage PTX with the co-loaded CDDP acts synergistically to reduce their toxic side effects and increase the treatment dosage for effective ovarian cancer treatment. Various ratios of co-delivered PTX and CDDP were tested for treating ovarian cancer cells. The in vitro cellular assays revealed the strongest synergism in anti-tumor effects when delivered at a 1:2 PTX/CDDP loading ratio. Using the SKOV-3 ovarian cancer xenograft mouse model, the co-encapsulation approach results in efficient tumor-targeted drug delivery, decreased cytotoxic effects, and stronger anti-tumor effect when compared with free drug combination or the single loading TM formulations.

Material and methods. Materials and Instruments. Paclitaxel was purchased from AK Scientific Inc. (Mountain View, Calif.). CDDP was purchased from Sigma-Aldrich. DiI was purchased from (AAT, Bioquest). Mono methoxyl terminated poly(ethylene glycol) monoamine (MeO-PEG-$NH_2$, M.W.: 5000 Da) was purchased from JenKem Technology, USA Inc. (Fmoc)Lys(Boc)-OH, (Boc)Lys(Boc)-OH and (Fmoc)Lys(Fmoc)-OH were purchased from AnaSpec Inc. (San Jose, Calif. USA). The MALDI matrix α-Cyano-4-hydroxycinnamic acid was purchased from Sigma Aldrich Chemical Co, used as supplied. Cholic acid and all other chemical reagents were purchased from Sigma-Aldrich. Dialysis membrane with 3500 MW cut off was purchased from Spectrum Laboratories, Inc. The preparations of cholic acid derivatives (Cholic acid NHS ester) were described in a previous publication. $^1$H NMR spectra were recorded on a Bruker AVANCE 600 MHz spectrometer. Mass spectra were acquired using a Bruker REFLEX-III MALDI-TOF mass spectrometer, equipped with a nitrogen laser delivering 3 ns laser pulses at 337 nm. Particle sizes of micelles were measured via a dynamic light scattering (DLS) particle sizer (Zetatrac, Microtrac Inc.) and also observed under a transmission electron microscope (TEM) JEOL JEM-2100 HR instrument at a voltage of 200 kv after stained with uranyl acetate solution. Zeta potential of TM before and after CDDP loading was measured via zetasizer (Malvern Inc.) in pure water.

Figure 19:
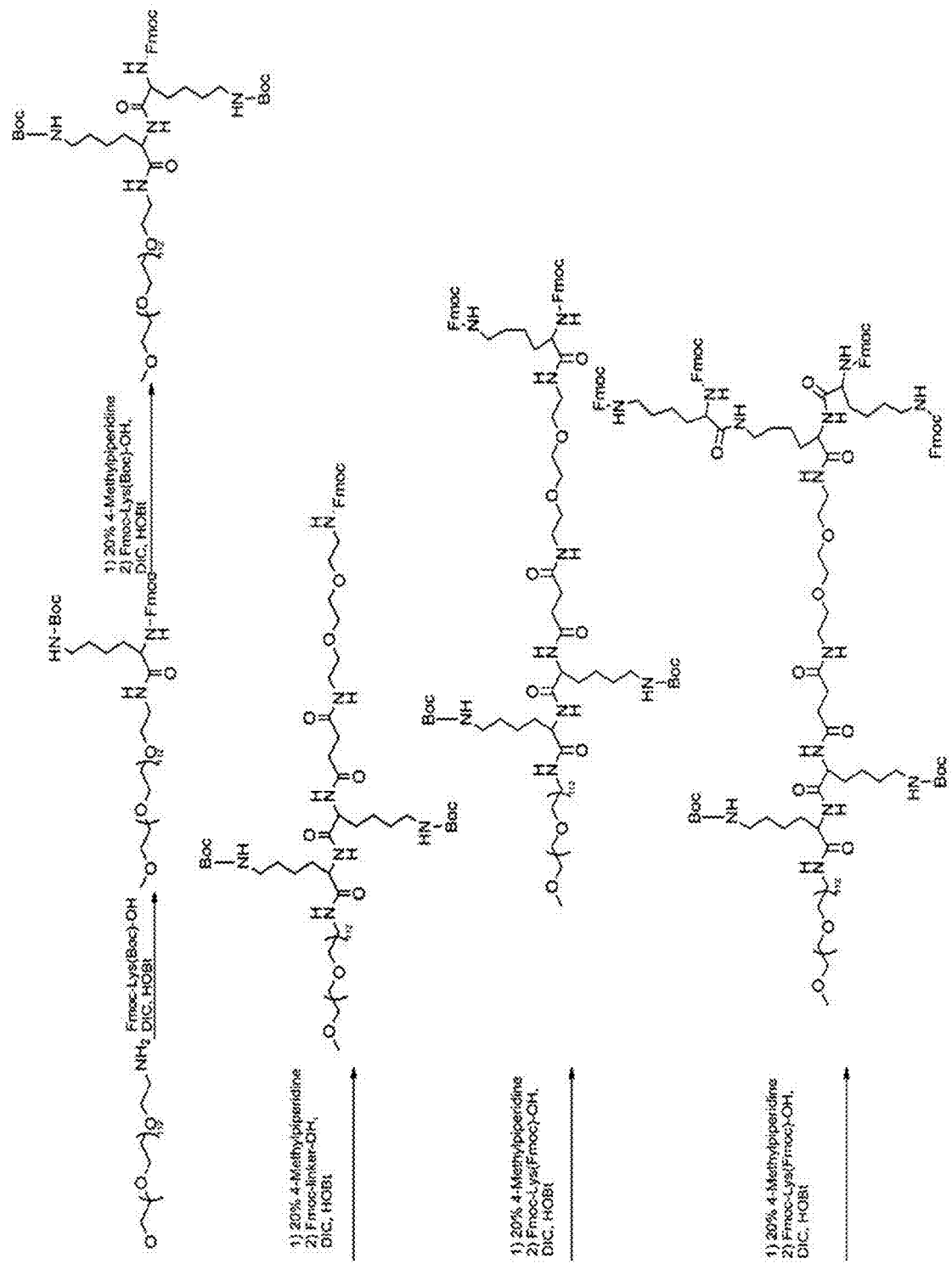
FIG. 19. Synthetic scheme of telodendrimer PEG$^{5k}$(COOH)$_8$-L-CA$_8$ via peptide chemistry and thio-ene click chemistry.
Figure 19:
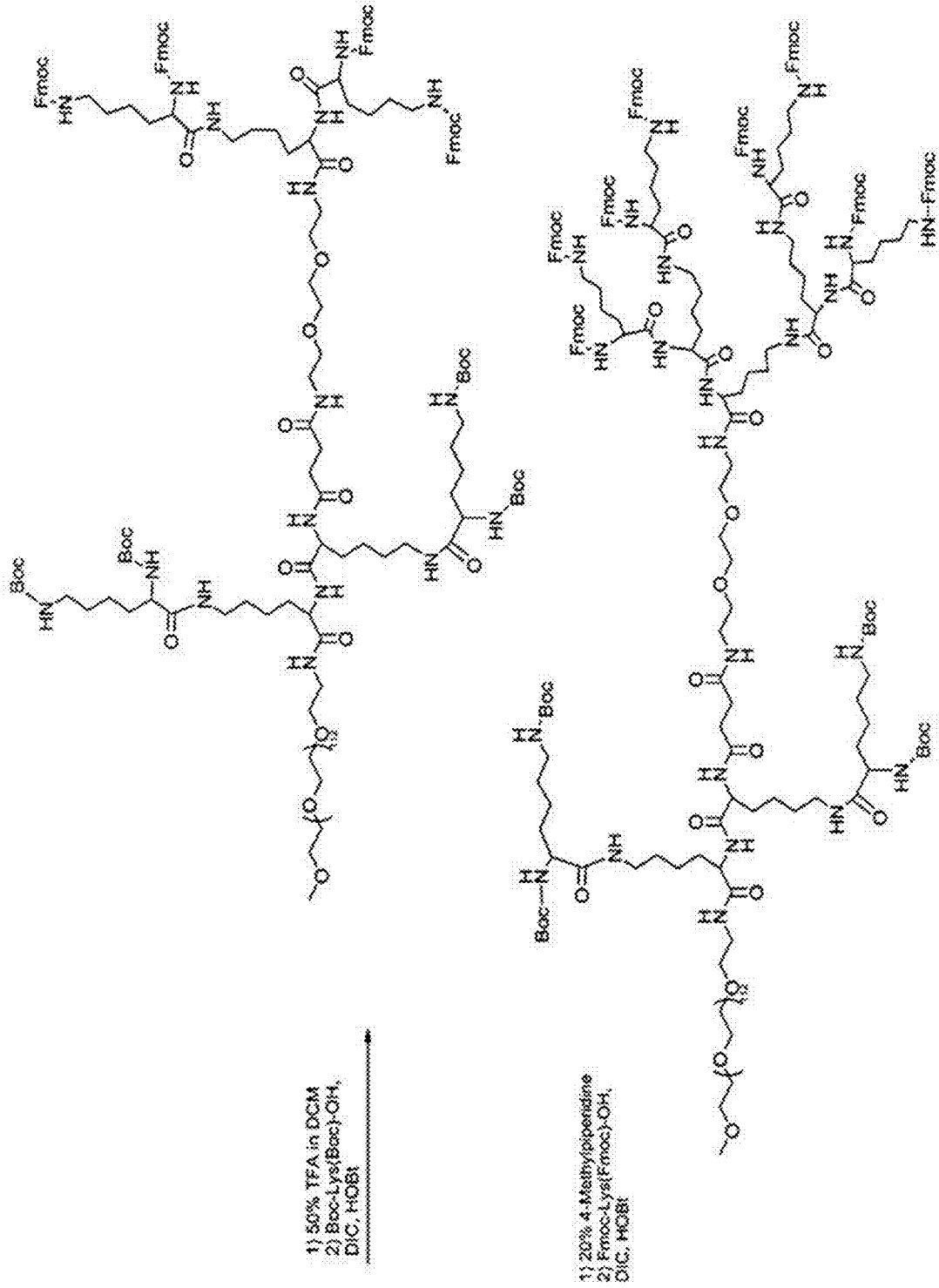
Figure 19:
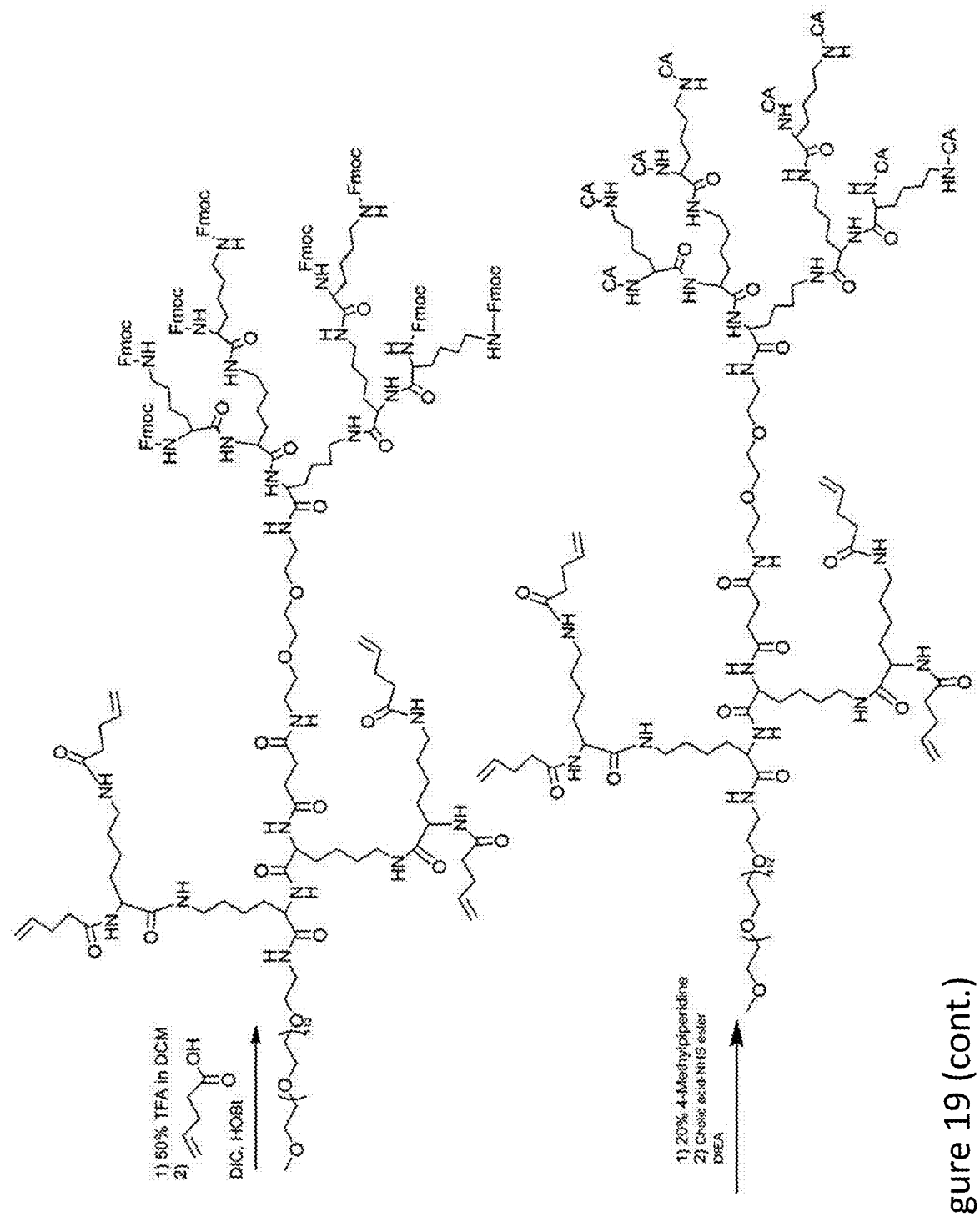
Figure 19:
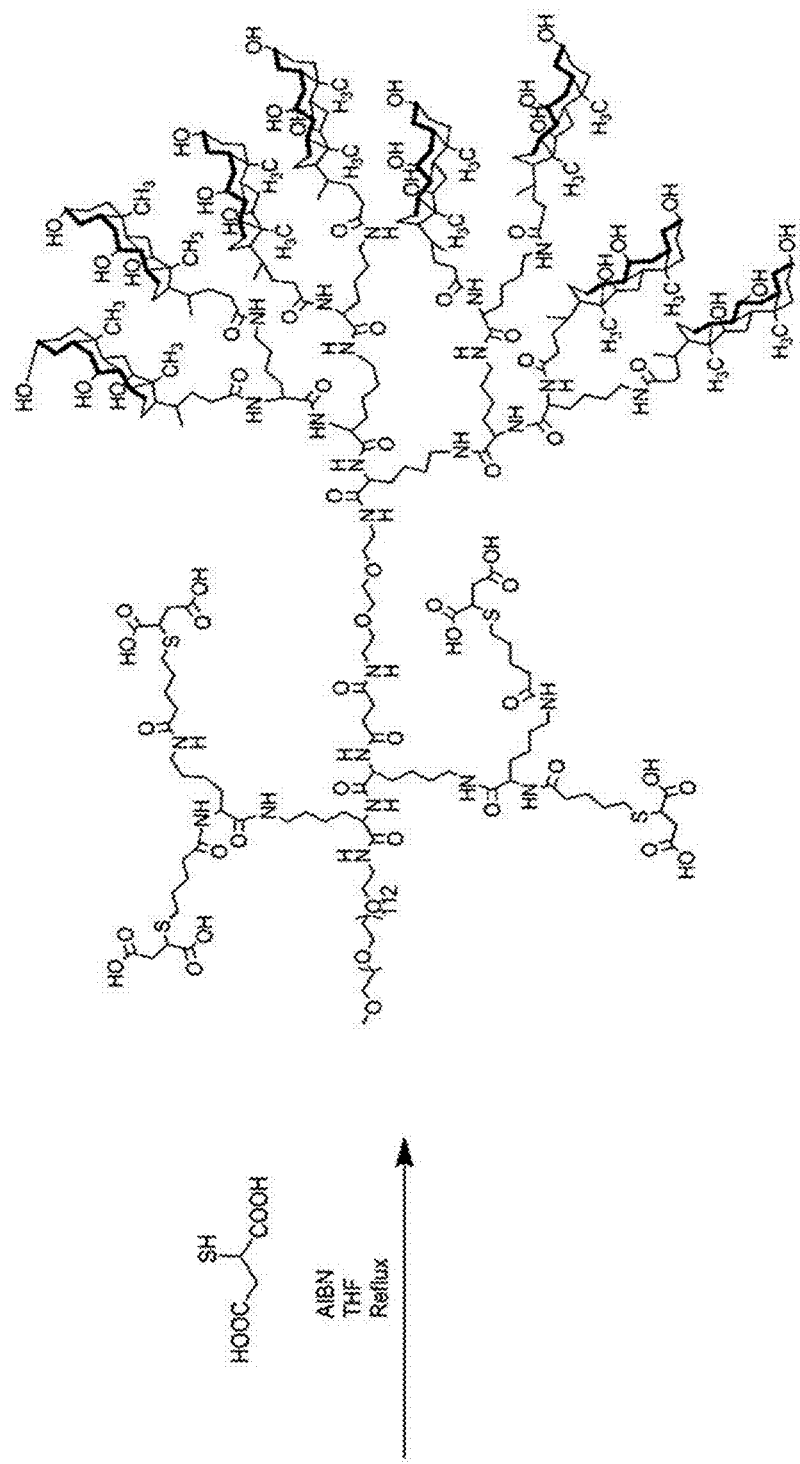

Telodendrimer synthesis. The nomenclature of the telodendrimers follows the following example, telodendrimer $PEG^{5K}(COOH)_8$-L-$CA_8$ indicates that the molecular weight of PEG is 5 kDa and there are 8 carboxyl group (CA) conjugated on the adjacent layer; eight cholic acid molecules were conjugated at the distal peripheral of telodendrimer and were segregated with a triethylene glycol linker molecule (L). The telodendrimers were synthesized using a solution-phase condensation reaction starting from MeO-$PEG^{5k}$-$NH_2$ (5000 Dalton) via stepwise peptide chemistry following the previous procedure and briefly described as following: (Fmoc)Lys(Boc)-OH was coupled onto the terminal amino group on PEG by using DIC and HOBt as coupling reagents until a negative Kaiser test result was obtained, which indicated the completion of the coupling reaction. PEGylated molecules were precipitated by pouring reaction solution into excess amounts of cold ether, followed by centrifugation and then washed with cold ether one or two times. The white powder precipitate was then dried under reduced pressure and the Fmoc protection group was removed by using 20% methylpiperidine solution in DMF and then polymer was precipitated. Second coupling of (Fmoc)Lys(Boc)-OH was coupled repeatedly. After removal of Fmoc groups on polymer, Fmoc protected triethylene glycol linker molecule was coupled to the terminal amino groups. Then three consecutive coupling of (Fmoc)Lys(Fmoc)-OH were carried out to generate a dendritic polylysine terminated with eight Fmoc groups and two Boc-protected amino groups at the adjacent sites of polymer. Further, $PEG^{5K}$-(NH-Boc)$_4$-L-(NH-Fmoc)$_8$ was obtained via coupling of (Boc)lys(Boc)OH onto the adjacent amino groups of the telodendrimers after removal of two Boc groups with 50% (v/v) trifluoroacetic acid (TFA) in dichloromethane (DCM). Four allylacetic acid were coupled on the amino groups after removal of Boc groups by using HOBt/DIC as coupling reagents to form $PEG^{5K}$-(Allyl)$_4$-L-(NH-Fmoc)$_8$(I). Cholic acid NHS esters were then coupled to the Fmoc-functionalized amino groups of dendritic polylysine after removal of Fmoc group to yield $PEG^{5K}$-(Allyl)$_4$-L-$CA_8$(II). 2-mercaptosuccinic acid molecules were finally coupled to the double bond via thio-ene click chemistry with the AIBN as initiator in THF under refluxing to generate carboxyl groups containing telodendrimer (III) $PEG^{5K}$(COOH)$_8$-L-$CA_8$ (FIG. 19).

The structures of intermediate telodendrimers I, II and III were characterized via $^1$H NMR to monitor the yield of each step. The final product was purified via dialysis against pure water for three days. Dialysis media was refreshed every 4 hrs.

Drug loading process. CDDP and PTX dual-drug-loaded micelles were prepared via a two-step method. TM aqueous solution was mixed with an aqueous solution of CDDP (1 mg/mL) at a molar ratio of ([cisplatin]/[COOH]=1:2) and incubated at 37° C. for 48 h. Unbound CDDP was removed by ultrafiltration device (molecular weight cut-off size (MWCO) 5,000 Da, Corning). The re-suspended solution was freeze-dried to obtain the CDDP-loaded powder $TM_{(CDDP)}$. Next, $TM_{(CDDP)}$ was dissolved in chloroform and different amount of PTX (CDDP/PTX=1:1, or 2:1, 4:1, w/w) was added and dissolved into the solution. Organic solvent was evaporated on a rotovap apparatus to obtain a homogeneous dry polymer film coated on the flask wall. Then it was further dried under high vacuum for 30 min. The thin film was dissolved into 1 mL distilled water, followed by sonication for 5 min, allowing the sample film to disperse into micelle solution. After 5000 rpm centrifuged for 5 min, the supernatant solution was filtered through a 0.45 μm filter to remove the unbound PTX precipitates. Pt content in the micelles was determined on an Inductively Coupled Plasma Optical Emission Spectrometer (ICP-OES, PerkinElmer) calibrated with Pt (2-100 ng/mL) and iridium as the internal standard. PTX levels were determined by high-performance liquid chromatography (HPLC, Shimadzu corporation) analysis. The mobile phase was composed of 55% of acetonitrile in water. The elute time was 10 min, the reverse phase column was a C18 (5 μm, 4.6×150 mm). The column temperature was maintained at 30° C. The flow rate was set at 1.0 mL/min and the detection wavelength was 227 nm. Docetaxel was used as an internal reference in HPLC analysis. The drug loading content (DLC %) and drug loading efficiency (DLE %) were calculated following the formula below: DLC %=(mass of drug in micelles/mass of drug loaded micelles)×100% DLE %=(mass of drug in micelles/total mass of drug for loading)×100%.

Drug release and micellar stability. Drug release from dual-drug-loaded micelles was examined in saline by dialysis method using a dialysis cartridge (Pierce Chemical Inc) with a 3.5 KDa MWCO. The dialysis was kept at 37° C. and swirled at 100 rpm. The concentrations of PTX and Pt(II) remained in the dialysis cartridge at various time points was measured by HPLC and inductively coupled plasma mass spectrometry (ICP-MS, PerkinElmer), respectively.

Critical micellization concentration (CMC): A series concentrations of empty TM, $TM_{(CDDP)}$, $TM_{(PTX)}$ and $TM_{(CDDP/PTX)}$ solutions in 0.01 M PBS were prepared in the range from 0.4 to 200 μg/mL Nile Red solution (20 μM) in MeOH was added to a series of wells of a 96-well plate. After MeOH was evaporated under vacuum, 100 μL of TM solutions at different concentrations were added to each well to obtain a final concentration of 1 μM Nile Red and mildly shaken overnight in dark at room temperature. Then, the fluorescent emission was measured at the wavelength of 620 nm (excited at 543 nm) using a micro-plate reader (BioTek, USA), and plotted vs the concentration of the telodendrimers. The CMC was determined by the threshold concentration, where the fluorescent intensity increases markedly.

Hemolytic assays: 1 mL of fresh blood from healthy human volunteers was collected into 10 mL of PBS solution in the presence of 1.5 mg/mL 20 mM EDTA. Red blood cells (RBCs) were then separated by centrifugation at 1000×g for 10 min. The RBCs were then washed three times with 10 mL of PBS, and re-suspended in 20 mL PBS. 200 µL of diluted RBC suspension was mixed with polymers at serial concentrations (10, 100, 500 and 1000 µg/mL) by gentle vortexing and incubated at 37° C. After 0.5 hrs, 4 hrs and overnight, the mixtures were centrifuged at 1000×g for 3 min. The supernatant free of hemoglobin was determined by measuring the UV absorbance at 540 nm using a UV-vis spectrometer (Thermo scientific). Incubations of RBCs with Triton-100 (2%) and PBS were used as the positive and negative controls, respectively. Triton X-100 (10 g/L) is a surfactant known to lyse RBCs. The hemolysis ratio of RBCs was calculated using the following formula: Hemolysis %= $(OD_{sample}-OD_{PBS})/(OD_{triton}-OD_{PBS})\times 100\%$. All hemolysis experiments were carried out in triplicates.

Confocal fluorescence cell imaging: The cellular uptake and intracellular trafficking of TM nanoparticles were determined via confocal laser scanning microscopy. DiI (a hydrophobic cyanine dye) was encapsulated together with CDDP into the TM to probe the nanoparticles in cell. SKOV-3 cells were seeded in chamber slide with a density of $5\times 10^4$ cells per well in 350 µL of McCoy's 5A and cultured for 24 h. And then original medium was replaced with free DiI and DiI-loaded $TM_{(DiI-CDDP)}$ at the final DiI concentration of 1 µg/mL at 37° C. or 4° C., respectively. After 30 min or 2 h incubation, the cells were washed three times with cold PBS and fixed with 4% formaldehyde for 10 min at room temperature, and the cell nuclei were stained with DAPI. The slides were mounted with coverslips and cells were imaged with a NiKON FV1000 laser scanning confocal fluorescence microscopy.

In vitro synergistic cytotoxicity: The cytotoxicity of blank micelles and drug-loaded micelle were assessed by measuring the cell viability using the standard MTS assay. SKOV-3 ovarian cancer cells and ES-2 ovarian cancer cells were seeded in 96-well plates at $4\times 10^3$ cells per well in 100 µL of McCoy's 5A with L-glutamine containing 10% fetal bovine serum, supplemented with 50 U/mL penicillin and 50 U/mL streptomycin, and incubated at 37° C. in 5% $CO_2$ atmosphere for 24 h. Different concentrations of the empty micelle solutions and drug-loaded micelles were added into the cell medium. After 72 h incubation, Cell Titer 96® Aqueous Cell Proliferation Reagent, which is composed of MTS and an electron coupling reagent PMS, was added to each well according to the manufacturer's instructions. The cell viability was determined by measuring the absorbance at 490 nm using a micro-plate reader. The wells contained untreated cells served as blank controls. Results were shown as the average cell viability $[(OD_{treat}-OD_{blank})/(OD_{control}-OD_{blank})\times 100\%]$ of triplicate wells.

The effective method to evaluate synergistic drug combinations in vitro is median-effect analysis, as originally proposed by Chou and Talalay (Chou T C. Theoretical basis, experimental design, and computerized simulation of synergism and antagonism in drug combination studies. Pharmacol Rev. 2006; 58:621-81. Chou T C, Talalay P. Quantitative analysis of dose-effect relationships: the combined effects of multiple drugs or enzyme inhibitors. Adv Enzyme Regul. 1984; 22:27-55.). The median-effect method assesses the drug-drug interaction by a term called the "combination index" (CI), which is based on the concentration-response relationship. CI was used to evaluate synergy between CDDP and PTX combination against SKOV-3, ES-2, and Hela cells in vitro. Values of CI<1, CI=1, and CI>1 indicate synergy, addivitity, and antagonism, respectively. CI analysis was performed by CalcuSyn software 1.0.

Xenograft Mouse Models. Female athymic nude mice (Nu/Nu strain), 5-6 weeks age, were purchased from Harlan (Livermore, Calif.). All animals were kept under pathogen-free conditions according to AAALAC (Association for Assessment and Accreditation of Laboratory Animal Care) guidelines and were allowed to acclimatize for at least 4 days prior to any experiments. All animal experiments were performed in compliance with institutional guidelines and according to protocol approved by the Animal Use and Care Administrative Advisory Committee. SKOV-3 ovarian cancer cells ($7\times 10^6$) in a 100 µL of mixture of PBS and Matrigel (1:1 v/v) without fetal bovine serum (FBS) were injected subcutaneously into the flanks of nude mice to form nodules.

Optical animal imaging: Nude mice bearing human SKOV3 ovarian cancer tumor (approximately 500 $mm^3$) were randomized into 2 groups (3 mice per group). DiD (a hydrophobic near-infrared (NIR) cyanine dye) was encapsulated in each nanocarrier (together with PTX and CDDP) at a ratio of 2:1:0.1 (CDDP/PTX/DiD by weight) using the same method as described above. The particle size was measured by DLS analysis. 100 µL of TM(DiD-PTX-CDDP) solution was filtered with a 0.22 µm filter to sterilize solution before injection. At the same time, same amount of DiD in DMSO solution was diluted with PBS right before I.V. injection. The fluorescent DiD co-loaded TM with equivalent dose of 6 mg/kg CDDP were injected into nude mice bearing SKOV-3 tumor xenograft via tail vein. Mice were anesthetized via isoflurane and optically imaged at different time points (1 h, 2 h, 4 h, 8 h, 24 h, 48 h and 72 h) using an IVIS 200 (PerkinElmer) with the (excitation/emission 625/700 nm). At the end of the experiments, the animals were sacrificed and all the major organs as well as tumors were excised for ex vivo imaging to determine the in vivo biodistribution of nanoparticles. The associated fluorescence intensities were determined by Living Image software (Caliper Life Sciences) using operator-defined regions of interest (ROI) measurements.

Pharmacokinetics and biodistribution. The blood pharmacokinetics study were performed using female SPF BALB/c mice, which were purchased from Charles River Laboratories Inc. Nanocarriers were administered into mice via tail vein injection with free drug mixture of CDDP/PTX or co-loading TM (CDDP/PTX=2:1) solution at a single equivalent dose of CDDP/PTX 6/3 mg/kg via tail vein. At defined time points (5 min, 0.5 h, 1 h, 2 h, 4 h, 8 h, 24 h and 48 h), blood samples were collected into heparinized tubes and immediately centrifuged at 1,000 rpm for 15 min to obtain plasma. Plasma samples were dissolved on heat in nitric acid and the platinum contents were measured by ICP-MS. The percentage of injected dose in plasma was calculated considering plasma volume in mice to be 45.6 mL/kg. (King F G, Dedrick R L. Physiological pharmacokinetic parameters for cis-dichlorodiammineplatinum(II) (DDP) in the mouse. J Pharmacokinet Biopharm. 1992; 20:95-9.)

In another set of the experiments, nude mice bearing human SKOV3 ovarian cancer tumor (approximately 500 $mm^3$) were randomized into 2 groups (3 mice per group). Free CDDP and TM (CDDP/PTX=2:1) were injected into nude mice via tail vein at a single equivalent dose of CDDP 6 mg/kg. At 48 h post-injection, major organs (heart, liver, spleen, lung and kidney) and tumor tissues were harvested from the mice. The organs were weighed and dissolved in the concentrated nitric acid by heating up (70° C.) and evaporated to dryness, and then re-dissolved in 0.1N HCl for tissue biodistribution of Pt analysis by ICP-MS.

Evaluation of the acute toxicity. Six-week-old female SPF BALB/c mice were randomized based on body weight into 3 groups (n=3). Mice were administered PBS, free drug mixture of CDDP/PTX=2:1 or TM (CDDP/PTX=2:1) at a single equivalent CDDP dose of 10 mg/kg through tail vein injection. The physical states and body weight change of the mice were monitored every day. On day 7 after injection, the blood was collected into heparinized tubes through cardiac puncture under anesthesia and animals were euthanized via $CO_2$ overdose and kidneys and livers were harvested and imbedded in OCT (Optimal Cutting Temperature Compound, Sakura Finetek USA, Inc) and stored at $-80°$ C. for further analysis. Serum were isolated and the clinical chemical parameters, including alanine aminotransferase (ALT), aspartate aminotransferase (AST) and blood urea nitrogen (BUN) were analyzed at the Cornell University Animal health Diagnostic Center. In addition, WBC, RBC and platelet were counted. Livers and kidneys were cut into serial 5 μm sections and fixed with 4% paraformaldehyde and stained with hematoxylin and eosin (H&E) for pathology analysis.

Evaluation of toxicity during the repeated treatment. Six-week-old female SPF BALB/c mice were administered intravenously 3 times at 4-day intervals with free drug mixture (CDDP/PTX=2:1) or $TM_{(CDDP/PTX=2:1)}$ at the doses of CDDP 4 or 6 mg/kg body weight, respectively. The physical conditions and body weight change of mice were monitored daily for four weeks. On day 7 after last injection, the blood was collected from each mouse for blood cell counting analysis. The MTD was defined as the allowance of a median body weight loss of 15% and causing neither death due to toxic effects nor remarkable changes in the general signs within two weeks after administration.

In vivo anticancer efficacy. Nude mice bearing human SKOV3 ovarian cancer tumor (approximately 150 $mm^3$) were randomly divided into 6 groups (n=5), including control (PBS only), free CDDP (4 mg/kg CDDP), $TM_{(PTX)}$ (3 mg/kg PTX), $PEG_{(CDDP)}$ (4 mg/kg CDDP), $TM_{(CDDP)}$ (6 mg/kg CDDP), and $TM_{(CDDP/PTX=2:1)}$ (6 mg/kg CDDP, 3 mg/kg PTX). Treatments were administered 3 times totally via tail vein on day 0, 4 and 8. Animal body weight and tumor volume were monitored every second day. Seven days after the last treatment, about 100 μL of blood was collected via tail bleeding for blood counts. The tumor sizes were measured with electronic calipers, and calculated using the following formula: V=(shortest $diameter^2$×longest diameter)/2. Animal were sacrificed when tumor volume exceeded 1500 $mm^3$, or the greatest tumor dimension exceeded 20 mm, or tumor became necrotic, or animal exhibited a body weight loss of more than 20%.

Statistical analysis. The level of significance in all statistical analyses was set at a probability of $P<0.05$. Data are presented as means±standard error (SEM). Statistical analysis was performed by Student's t-test for comparison of two groups, and one-way analysis of variance (ANOVA) for multiple groups, followed by Newman-Keul's test if overall $P<0.05$.

In this example, we introduced multiple carboxyl groups onto an adjacent site of telodendrimer using peptide chemistry and the thio-ene click chemistry. The resulting telodendrimer enables the loading of platinum drugs via carboxyl chelating, at the same time, encapsulating hydrophobic molecules like paclitaxel in the interior core of the micelles.

Following the procedure in a previous publication telodendrimers were synthesized from the amino group of MeO-$PEG^{5k}$-$NH_2$ via solution phase peptide chemistry. Kasier tests were performed based on known methods during each step of peptide coupling reactions to ensure the completion of the reaction. In addition, $^1H$ NMR was used to characterize the chemical structures of the intermediate and the final telodendrimer. The chemical structure of the important intermediates, i.e. $PEG^{5k}(Boc)_2$-L-$(Fmoc)_8$ and $PEG^{5k}(Boc)_4$-L-$(Fmoc)_8$ was confirmed via MALDI ToF MS and $^1H$ NMR analysis with the doubling signal of Boc groups observed. Further, four allylacetic acid molecules were coupled on the amino groups by using HOBt/DIC as coupling reagents after the removal of Boc groups to form $PEG^{5K}$-$(Allyl)_4$-L-$(NH-Fmoc)_8$ (I). Cholic acid NHS esters were then coupled on the peripheral of dendritic polylysine after removal of Fmoc groups to yield $PEG^{5K}$-$(Allyl)_4$-L-$CA_8$ (II). Subsequently, 2-mercaptosuccinic acid molecules were added to the vinyl double bond via "thio-ene" click chemistry to introduce carboxyl groups onto telodendrimer (III) $PEG^{5K}(COOH)_8$-L-$CA_8$.

Figure 3:
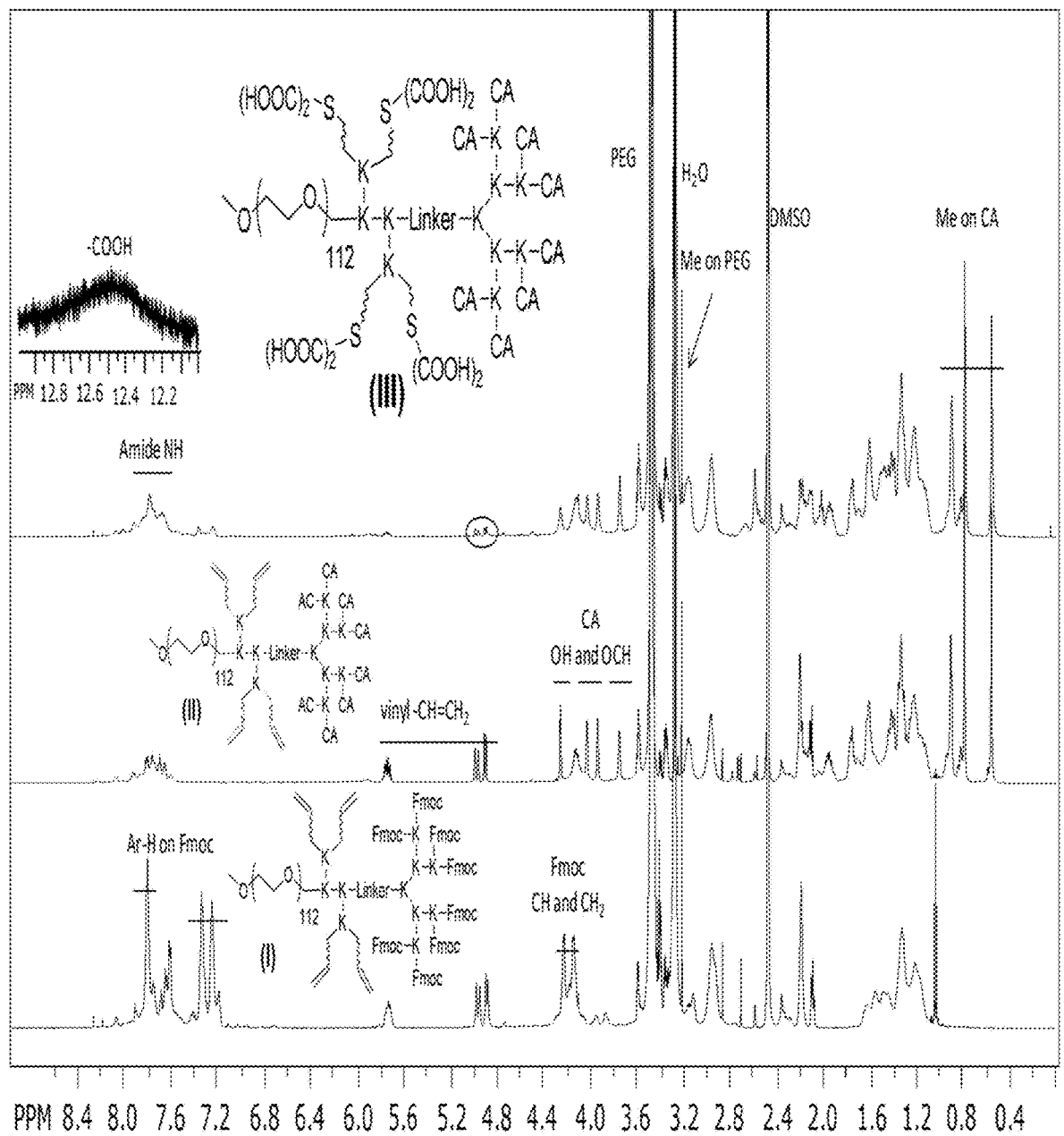
FIG. 3. $^1H$ NMR spectra of telodendrimers I, II and III in DMSO-d6 at a concentration of 5 mg/mL, detected by 600M Bruker NMR. The protons on Fmoc were marked in telodendrimer I; OH and OCH of CA and vinyl protons appeared in telodendrimer II; the Me of CA and emerging COOH and disappearing vinyl groups were shown in telodendrimer III.

As shown in FIG. 3, signature peaks for vinyl protons (5.7 ppm and 4.8~5.0 ppm) were evident within the telodendrimer with detected number close to the theoretical number of 4 based on the area integration relative to the methyl signal on MeO-PEG (3.2 ppm). In addition, protons of the Fmoc protecting groups were shown at 7.2-7.8 ppm and 4.0-4.4 ppm. After removal of Fmoc and CA conjugation, three unique methyl groups of CA appeared from 0.5 to 1 ppm and some other signature protons of CA, e.g., —OH and —OCH—, were shown between 3.6 to 4.3 ppm in NMR spectrum of telodendrimer II. After the last step of thio-ene click chemistry, carboxylic acids were detected in telodendrimer III at 12.5 ppm. MALDI-ToF MS spectrophotometer and NMR analysis revealed the composition of the final telodendrimer III to be $PEG^{5k}COOH_{6.3}$-L-$CA_{6.2}$ and an approximate molecular weight of 9470 Daltons. The telodendrimer III self-assembles into micelles. The critical micellization concentration (CMC) of the micelles were measured to be 29.6 μg/mL using Nile Red as a fluorescent probe. The zeta potential of the empty telodendrimer micelles (TM) was measured to be $-11.3$ mV in pure water, which was shifted to 3.1 mV after CDDP complexation.

TABLE 1

Characterization and drug loading properties of telodendrimers.

| Formula (via NMR) | MW (Dalton) MS | MW (Dalton) Theo | CMC (μg/mL) | TM Size (nm) | Size after drug loading (nm) $TM_{(PTX)}$ | Size after drug loading (nm) $TM_{(CDDP)}$ | Size after drug loading (nm) $TM_{(PTX-CDDP)}$ |
|---|---|---|---|---|---|---|---|
| $PEG^{5k}COOH_{6.3}$-L-$CA_{6.2}$ | 9471 | 10650 | 29.6 | 9.0 ± 2.6 | 16.0 ± 3.7 | 16.9 ± 3.7 | 16.9 ± 4.8 |

The empty telodendrimer micelle has a hydrodynamic diameter of 9.0±2.6 nm, as determined by dynamic light scattering (DLS) particle sizing. This size is smaller than the typical telodendrimer PEG$^{5k}$CA$_8$ (~20 nm), due to the decoration of the hydrophilic carboxyl groups. It is feasible to first encapsulate PTX physically into the hydrophobic core of micelle, then incubate with CDDP in aqueous solution for CDDP loading. However, it was found that the single loading of PTX had poor reproducibility and was sensitive to pH. The loading of PTX in acidic solution (pH 4-5) yields stable micelles with monodispersed particle sizes (16.0±3.7 nm) at a 10:1 polymer/drug mass ratio. However, the particle sizes of the PTX-loaded micelles TM$_{(PTX)}$ increase and become heterogeneous with the increase of pH at neutral or basic condition, which is preferred for CDDP complexation. This is due to the charge repulsion of the deprotonated carboxyl groups of the telodendrimer, which destabilize the micelles and the payload drug molecules. Therefore, an alternative approach was adopted to load CDDP first in pure water and then encapsulate PTX. The rational is that the CDDP complexation would neutralize the carboxyl groups and restore the balanced amphiphilicity of the telodendrimer for efficient PTX loading. The particle sizes of TMs with single CDDP loaded were detected via DLS to be 16.9±3.7 nm. The drug loading content (DLC) and drug loading efficiency (DLE) were measured via ICP-OES to be 10% and 97%, respectively. After lyophilization, TM (CDDP) powder was used for PTX loading via a thin-film dispersion method. The CMCs of drug-loaded micelles were decreased slightly to 26.8 and 23.8 µg/mL after single loading of CDDP and the coloading of CDDP/PTX (2:1 by weight), respectively.

After co-loading of CDDP and PTX at a ratio of polymer/PTX/CDDP at 5:0.5:0.2 mg/mL, the particle had a similar sizes of 16.9±4.8 nm, where the PTX loading efficiency was detected to be 92% by HPLC. When the particles contained CDDP/PTX at different ratios, e.g., TM$_{(CDDP/PTX=1:1)}$, TM$_{(CDDP/PTX=2:1)}$, TM$_{(CDDP/PTX=3:1)}$ and TM$_{(CDDP/PTX=4:1)}$, the apparent diameters were similar at around 20 nm by DLS. TEM images revealed that majority of empty and drug loaded micelles had similar spherical shape that increased slightly in size between 10 to 20 nm with the addition of the chemotherapeutic drug.

Drug release and stability of TM$_{(CDDP/PTX)}$ in vitro: The assembled nanoparticles were assessed to be stable after prolonged incubation, e.g., storage at 4° C. for a month. In addition, the cryoTEM imaging revealed homogenous particle sizes of TM$_{(CDDP/PTX)}$ over the storage period. The drug release profiles for both PTX and CDDP from TM$_{(CDDP/PTX)}$ were studied via a dialysis experiment against saline. PTX released much faster (50% release within 24 h) than CDDP (50% release within 92 h). To determine the blood compatibility of the nanotherapeutics, we incubated the empty and drug assembled nanoparticles with human red blood cells in vitro. No hemolytic activity was observed from either the empty TM and drug loaded TMs after overnight incubation, even at a high polymer concentration of 1 mg/mL.

Cellular uptake: In order to visualize and determine the overall intracellular trafficking of TMs, we incorporated a fluorescent dye (DiI) into micelles loaded with DDP and PTX, which were incubated with SKOV-3 ovarian cancer cells for confocal cell imaging. The amphiphilic dye DiI has been demonstrated to be a stable probe molecule to capture the intracellular trafficking of polymer micelles. Free DiI quickly diffused into the mammalian cells; diffusion was strongly hindered when the dye was embedded into the nanoparticles. It was observed that temperature has less impact on free DiI diffusion. In contrast, the cell uptake of TM$_{(DiI/CDDP/PTX)}$ was almost depleted at 4° C., which indicates an energy dependent process for nanoparticle uptake. In addition, the cells were also stained with lysotracker green to label lysosome within cytoplasm. Here, we found that cells treated with the TM nanoparticle formulations had stronger colocalization of DiI dye within the lysosome compartments, indicating the endocytosis pathway for TMs to deliver their contents into cells.

Figure 4:
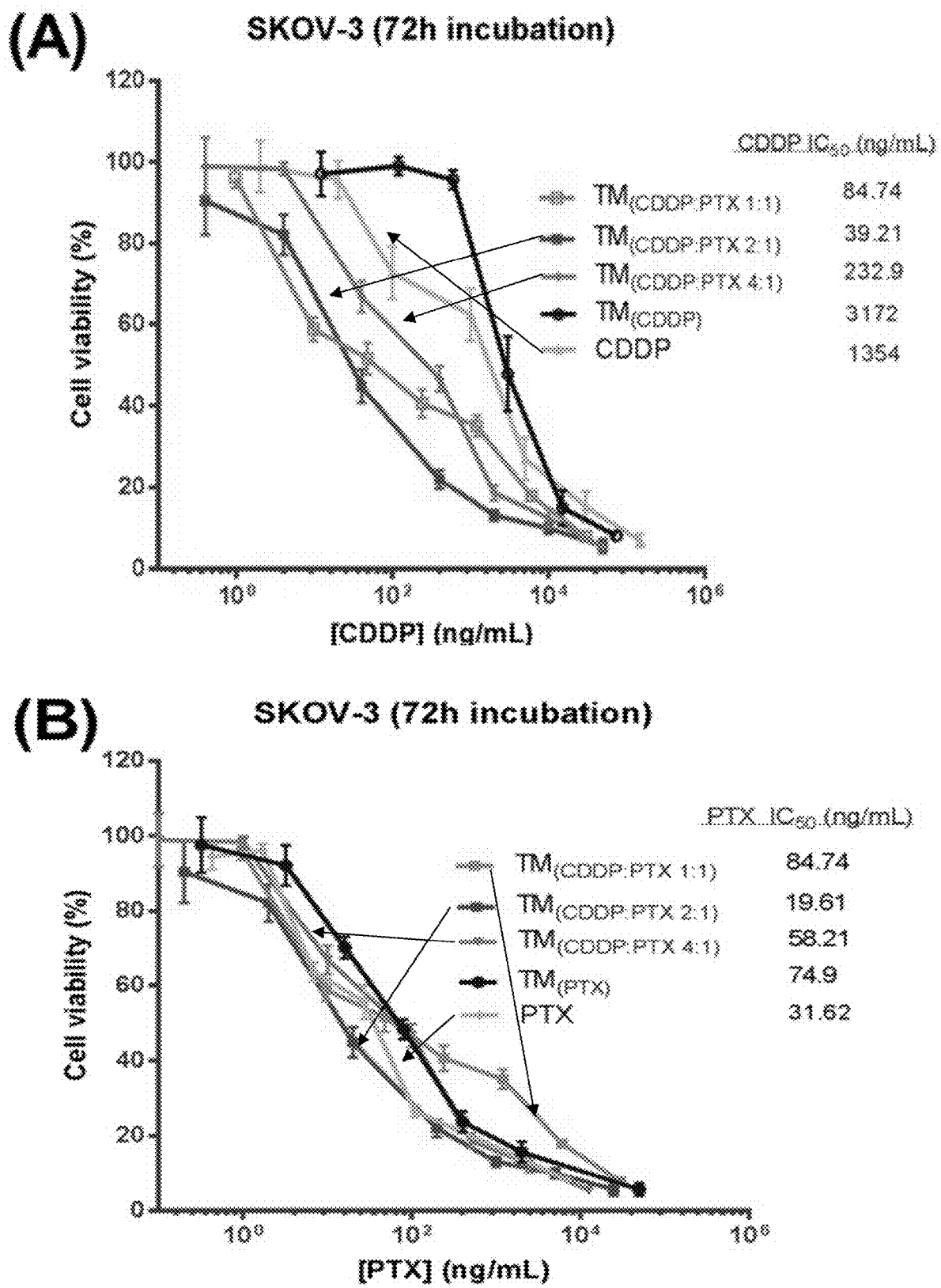
FIG. 4. Cell viability of SKOV-3 ovarian cancer cells after incubated for 72 h with free CDDP, free PTX, single loading of $TM_{(PTX)}$ and $TM_{(CDDP)}$ and the coloading TM (CDDP: PTX0 at different ratios. The cell viabilities were displayed against PTX concentration (A) and CDDP concentration (B), respectively. The combination index of the co-loading TM formulations with different ratio of CDDP/PTX in SKOV-3(C), ES-2 cells (D) and in Hela cells (E).
Figure 4:
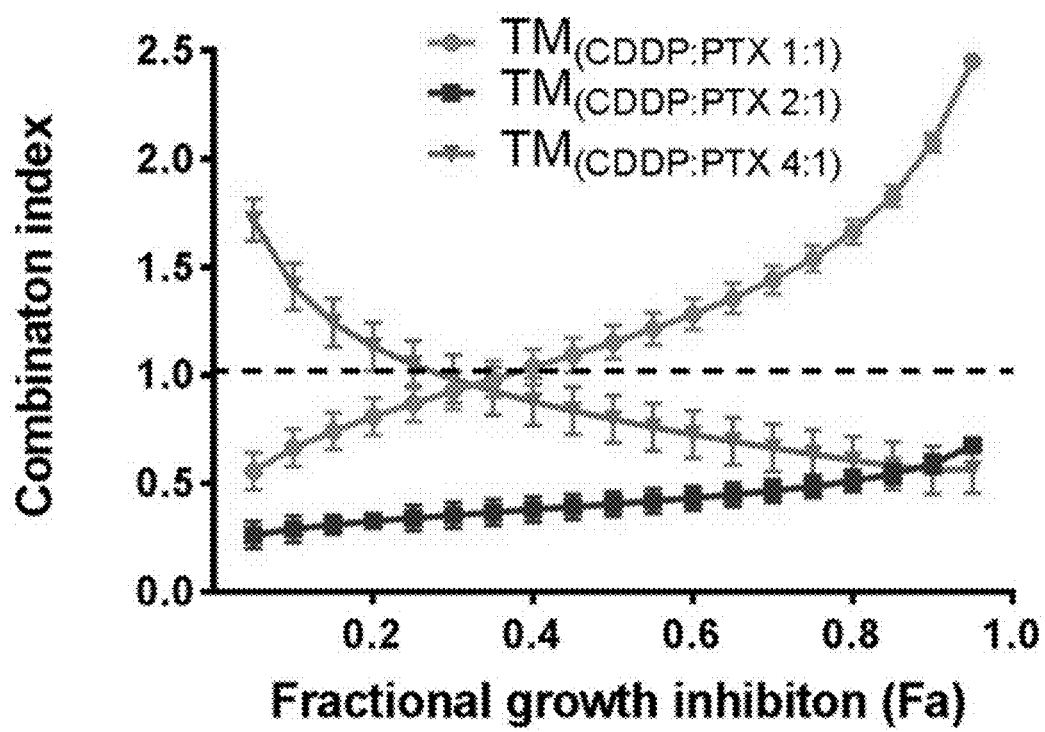

In vitro synergistic cytotoxicity: It has been reported that the synergistic combinations of CDDP and PTX depends largely on the dosing sequence, time interval and dose concentrations of these two drugs: Given the nature of our nanoparticle, it is likely that the faster PTX release kinetics favor a pattern that is consistent with current anticancer combinatorial regiments. The empty TM showed non-cytotoxic up to 1 mg/mL concentration after 72 h incubation with several cell lines, including SKOV3 ovarian cancer cells. The single loading of either CDDP or PTX exhibited slightly reduced potency compared with the free drugs against SKOV3 cells because of slow drug release profiles (FIG. 4). After being co-loaded with different ratio of CDDP and PTX, the cytotoxicity of the TM$_{(CDDP/PTX)}$ were significantly increased in killing ovarian cancer cells, compared with free CDDP, due to the high potency of PTX (FIG. 4A). Importantly, the IC$_{50S}$ of PTX were also further decreased upon of the addition of CDDP, which show nontoxic at this concentration (IC50s: CDDP: 1354 ng/mL; PTX: 32 ng/mL, shown in Table 2). It was interesting to observe the best cell killing at the combination of 2:1 ratio of CDDP/PTX in the co-loading formulations with the lowest combination index of 0.21 at 50% of cell killing (CI50), indicating a strong synergism. According to the definition of CI, values of CI<1, CI=1, and CI>1 indicate synergy, additivity, and antagonism, respectively. As shown in Table 2, the similar trends in cell growth inhibition via the combination therapy were observed in ES2 and Hela.

TABLE 2

IC50 and CI values of TM(PTX/Pt)s with various PTX/Pt ratios

| Formulations | CDDP/PTX ratio(w/w) | SKOV-3 IC$_{50}$ (ng/mL) | CI$_{50}$ | ES2 IC$_{50}$ (ng/mL) | CI$_{50}$ | Hela IC$_{50}$ (ng/mL) | CI$_{50}$ |
|---|---|---|---|---|---|---|---|
| CDDP | | 1354 | — | 920 | — | 2427 | — |
| TM$_{(CDDP)}$ | | 3172 | — | 1429 | — | 6765 | — |
| PTX | | 32 | — | 55 | — | 20 | — |
| TM$_{(PTX)}$ | | 75 | — | 82 | — | 35 | — |
| TM$_{(CDDP/PTX=1:1)}$ | 1:1 | 85/85 | 1.16 | 126/126 | 1.62 | 40/40 | 1.15 |

TABLE 2-continued

IC50 and CI values of TM(PTX/Pt)s with various PTX/Pt ratios

| Formulations | CDDP/PTX ratio(w/w) | SKOV-3 | | ES2 | | Hela | |
|---|---|---|---|---|---|---|---|
| | | IC$_{50}$ (ng/mL) | CI$_{50}$ | IC$_{50}$ (ng/mL) | CI$_{50}$ | IC$_{50}$ (ng/mL) | CI$_{50}$ |
| TM$_{(CDDP/PTX=2:1)}$ | 2:1 | 39/19.5 | 0.21 | 95/47.5 | 0.65 | 38/19 | 0.54 |
| TM$_{(CDDP/PTX=4:1)}$ | 4:1 | 233/58.3 | 0.87 | 242/60.5 | 0.91 | 109/27.3 | 0.79 |

Furthermore, the CI of the whole cell killing panel were analyzed via CalcuSyn software. It clearly demonstrated the synergism for TM$_{(CDDP/PTX=2:1)}$ in almost the whole range of Fa with CI<1 in all three cell lines. (FIGS. 4C, D&E). However, for TM$_{(CDDP/PTX=4:1)}$, CI value declined gradually along with the rise of Fa, but it was more than 1 when Fa was at the range of 0.05-0.4. With regards to TM$_{(CDDP/PTX=1:1)}$, CI increases gradually along with the rise of Fa, and exceeds CI=1 in the Fa range of 0.4-0.95. The similar trend of synergism of TM$_{(CDDP/PTX)}$ were observed in ES2 cells and Hela cells. TM$_{(CDDP/PTX=2:1)}$ exhibited the best cancer cell killing effects (lowest IC50) via synergistic drug combination in all three cell lines.

Figure 5:
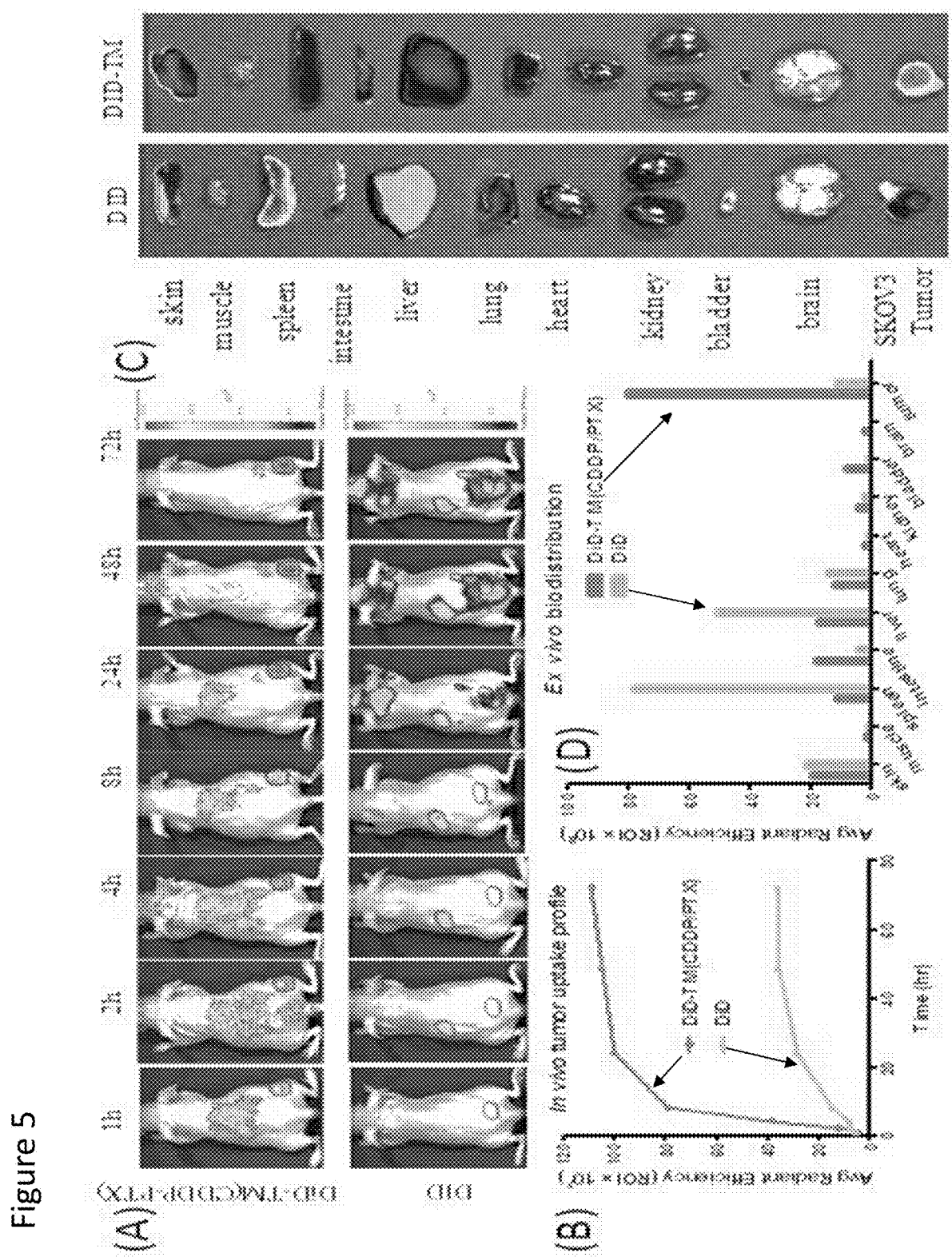
FIG. 5. In vivo (A) and ex vivo (C) NIRF optical images of Raji lymphoma bearing mice injected intravenously with free DiD and DiD-PTX-CDDP coloaded TM formulations, respectively. The in vivo tumor targeting (B) and ex vivo tumor and organ uptake (D) were quantitatively analyzed.

Fluorescence animal imaging: Non-invasive and real time near-infrared fluorescence (NIRF) imaging was utilized to image the tissue distribution and tumor accumulation of nanocarriers in vivo. To track the in vivo fate of the TM nanocarriers and probe the biodistribution of the hydrophobic PTX in the nanocarriers, a NIRF hydrophobic dye DiD was encapsulated together with CDDP and PTX at 2:1 ratio (w/w) into TM nanocarriers as determined previously. The particle sizes were measured to be 20.4±3.8 nm via DLS. The in vivo fluorescent optical imaging of whole body (FIG. 5A) showed that DiD-labeled TM$_{(CDDP/PTX)}$ micelles were able to gradually accumulate at the SKOV-3 tumor xenograft starting at 2 h and reached a plateau at 24 h and throughout the 72 h period after tail vein injection (FIG. 5B). In contrast, very weak tumor fluorescence was observed in the mice injected with free DiD. At 72 h of post-injection, tumor and other major organs were harvested for ex vivo NIRF imaging to compare the tissue distribution of TMs (FIG. 5C). As shown in FIG. 4D, DiD-loaded TM$_{(CDDP/PTX)}$ micelles were mainly accumulated in tumor with more than 4-fold higher intensity than that in the vital organs, e.g., liver, lung, spleen and kidney. While DiD was mainly taken up by the spleen and liver in the mice treated with the free DiD, it had low intensity in tumor. This may have resulted from the aggregation of highly hydrophobic DiD in free DiD administration.

Figure 6:
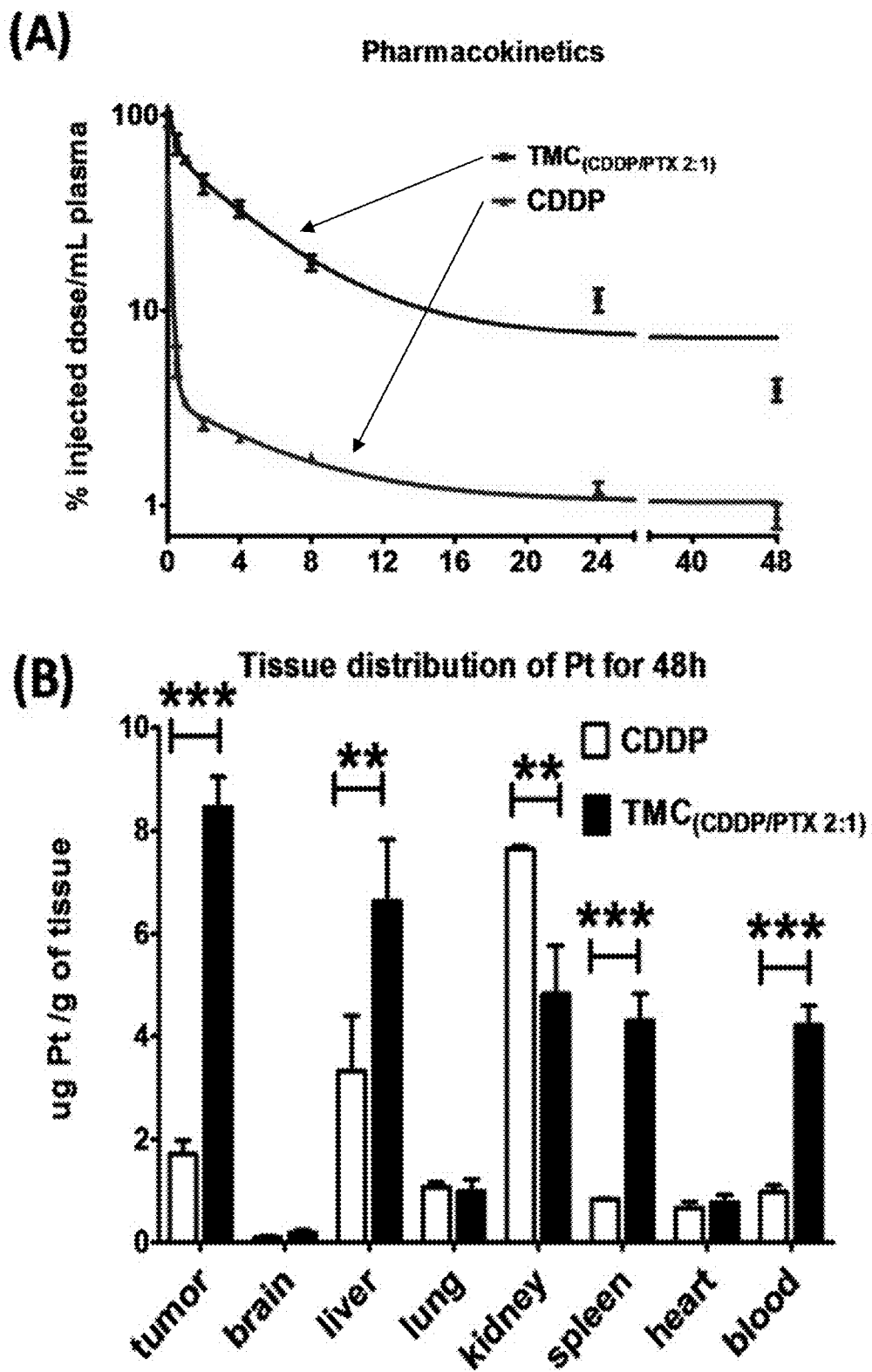
FIG. 6. (A) In vivo pharmacokinetics profiles of platinum concentration in the plasma after i.v. administration of free CDDP and $TM_{(CDDP/PTX)}$. (B) Tissue distribution of platinum concentration in the plasma on day 2 after i.v. administration of free CDDP and PB-CDDP-PTX. Each drug was administered to Nude mice bearing human SKOV3 ovarian cancer tumor (female, n=3) at a dose of 6 mg/kg on CDDP basis. Data were expressed as mean±SE (: p<0.01; *: p<0.005).

Pharmacokinetics and biodistribution of TM$_{(CDDP/PTX)}$ in vivo: CDDP concentrations were analyzed in the following pharmacokinetic (PK)-biodistribution study. The PK profile of Pt in plasma were analyzed via the HCP-MS at defined time points after intravenous administration of free drug mixtures CDDP/PTX or TM$_{(CDDP/PTX)}$ nanoformulation in nude mice (FIG. 6A). The maximum detected Pt concentrations in plasma at 5 min was approximately 3 times greater for the nanoformulation over free drug injection (88 ug/mL and 27.6 µg/mL respectively). Free CDDP was rapidly cleared from plasma, and only 5% Pt of the injected dose was detected in plasma at 30 min after injection and less than 1% at 24 h post injection. Markedly, the TM$_{(CDDP/PTX)}$ nanocarrier displayed slower clearance rates; approximately 75% and 13% of total Pt remained at 30 mins and 24 hrs, respectively.

The pharmacokinetic parameters were calculated using a two compartment model with PKsolver. As shown in Table 3, the half life time of TM$_{(CDDP/PTX)}$ were increased by 16-fold and 3-fold for α-phase and βphase elimination, respectively, compared with free CDDP administration. The clearance rate (Cl) of free CDDP were analyzed to be much higher (20 to 25 fold) than for the nanotherapeutics for both phases. In addition, the area under the curve (AUC) for the mice treated with TM$_{(CDDP/PTX)}$ was calculated to be 627.44 vs 30.8 µg/ml*h for the free CDDP injection. Furthermore, the steady state volume of distribution (V$_{ss}$) of Pt was effectively decreased by more than 20-fold in the nanoformulation over free CDDP drug, indicating that the nanoparticle was more effective at retaining CDDP in the systemic circulation. These results strongly suggest that our nanoparticle has a long-circulating half-life and is stable within the systemic circulation.

TABLE 3

Pharmacokinetic parameter estimations of platinum in plasma of nude mice beard SKOV-3 xenograft after being treated with CDDP and TM(CDDP/PTX) through tail vein.[a]

| Parameters | TM$_{(CDDP/PTX)}$ | CDDP |
|---|---|---|
| t$_{1/2}$α (h) | 0.72 | 0.044 |
| t$_{1/2}$β (h) | 12.36 | 4.30 |
| C$_{max}$[b] (µg/mL) | 88.02 | 27.58 |
| CL (mL/kg/h) | 6.38 | 129.87 |
| CL2 (mL/kg/h) | 22.35 | 559.30 |
| AUC (µg/ml*h) | 627.44 | 30.80 |
| Vss (mL/kg) | 103.55 | 668.10 |

C$_{max}$ represents the maximum observed concentration at the earliest evaluated time point of 5 min post iv injection; Plasma concentration at 0 h time point were calculated based on the dose of 4 mg/Kg.
Abbreviations: t$_{1/2}$, half lifetime; C$_{max}$, maximum platinum concentration; AUC, area under the curve; Cl, clearance; V$_{ss}$, steady-state volume of distribution.

NIRF optical imaging (FIG. 5) has indicated the preferred tumor uptake of the TM and the hydrophobic payload. In addition, the tissue biodistribution of Pt was measured via HCP-MS at the end of PK studies at 48 h post-injection. As shown in FIG. 6B, TM formulations significantly altered the biodistribution and tumor uptake of Pt in animals. In mice treated with TM$_{(CDDP/PTX)}$, the Pt uptakes in the tumor and blood were 4-fold and 5-fold higher than those treated with the free CDDP, respectively (P<0.01). In addition, it was also noted that the accumulation of Pt in kidneys was significantly reduced in the TM$_{(CDDP/PTX)}$ group compared with the group treated with free drug mixture, which may mitigate the Pt-associated nephrotoxicity. (Alexis F, Pridgen E, Molnar L K, Farokhzad O C. Factors affecting the clearance and biodistribution of polymeric nanoparticles. Mol Pharm. 2008; 5:505-15.) Both NIRF imaging and Pt biodistribution studies indicated the highest tumor uptake of both hydrophobic DiD (as a surrogate of PTX) and CDDP in the animals treated with nanoformulation.

Overall, kidney/tumor and liver/tumor ratio of Pt concentrations were observed to be 4 and 2 respectively in the animals treated with free CDDP. In contrast, in TM$_{(CDDP/PTX)}$ group, Pt concentration in tumor was the highest among all other organs. The comparison of increased tumor uptake and decreased kidney uptake would suggest the increased efficacy and the reduced renal toxicity of TM$_{(CDDP/PTX)}$ nanoformulation. At the same time, Pt concentrations in liver and spleen in mice treated with TM$_{(CDDP/PTX)}$ formulation were 2-5 fold as higher as that in the free CDDP group, which was due to the sustained blood circulation of nanoformulation. Therefore, the toxicity studies need to be done carefully in evaluating liver and kidney functions before and during the combination therapy.

In vivo toxicity of combination therapeutics. According to the literature, the maximum tolerated dose (MTD) of free CDDP and some other nanoformulations of CDDP were set at 4 mg/kg or lower for cancer treatment in mouse models. Therefore, we started testing TM$_{(CDDP/PTX=2:1)}$ in BALB/c mice at 4 mg/kg of CDDP dosage and escalated the dose with a 50% increment, i.e. 6 mg/kg via tail vein injection for 3 times every four days. There was no obvious body weight loss in 4 mg/kg cohort. And only a mild body weight loss about 7.6% was observed at the dose level of 6 mg/kg on day 10, which were recovered at the end of week 3 (FIG. 7A). No other toxicity signs and animal death was observed in the both groups. Blood cell counting analysis on day 7 after the last injection was conducted and normal cells counting were observed for red blood cells, white blood cells and platelets for both groups (FIG. 7D-E). In this example, the MTD of a three-dosage regimen was determined to be higher as CDDP 6 mg/kg/PTX 3 mg/kg for TM$_{(CDDP/PTX=2:1)}$ in the non-tumor bearing female BALB/c mice.

Acute toxicity of CDDP was studied in BALB/c mice after a single intravenous tail vein injection of the free drug combination (CDDP/PTX 2:1 w/w) and the combination nanotherapeutics TM$_{(CDDP/PTX=2:1)}$ at a much higher dosage level of 10 mg CDDP and 5 mg PTX/kg. As shown in FIG. 7B, the mice treated with a free drug mixtures led to about 24±2.14% body weight loss on day 6. In contrast, the TM$_{(CDDP/PTX=2:1)}$ administration group showed only a small reduction (~2%) in body weight (p<0.01). The overall behaviors of mice had no different in TM$_{(CDDP/PTX=2:1)}$ group compared with the mice in the control group; but the mice treated with high dose of free drug mixture were significantly weaker and less active.

Figure 7:
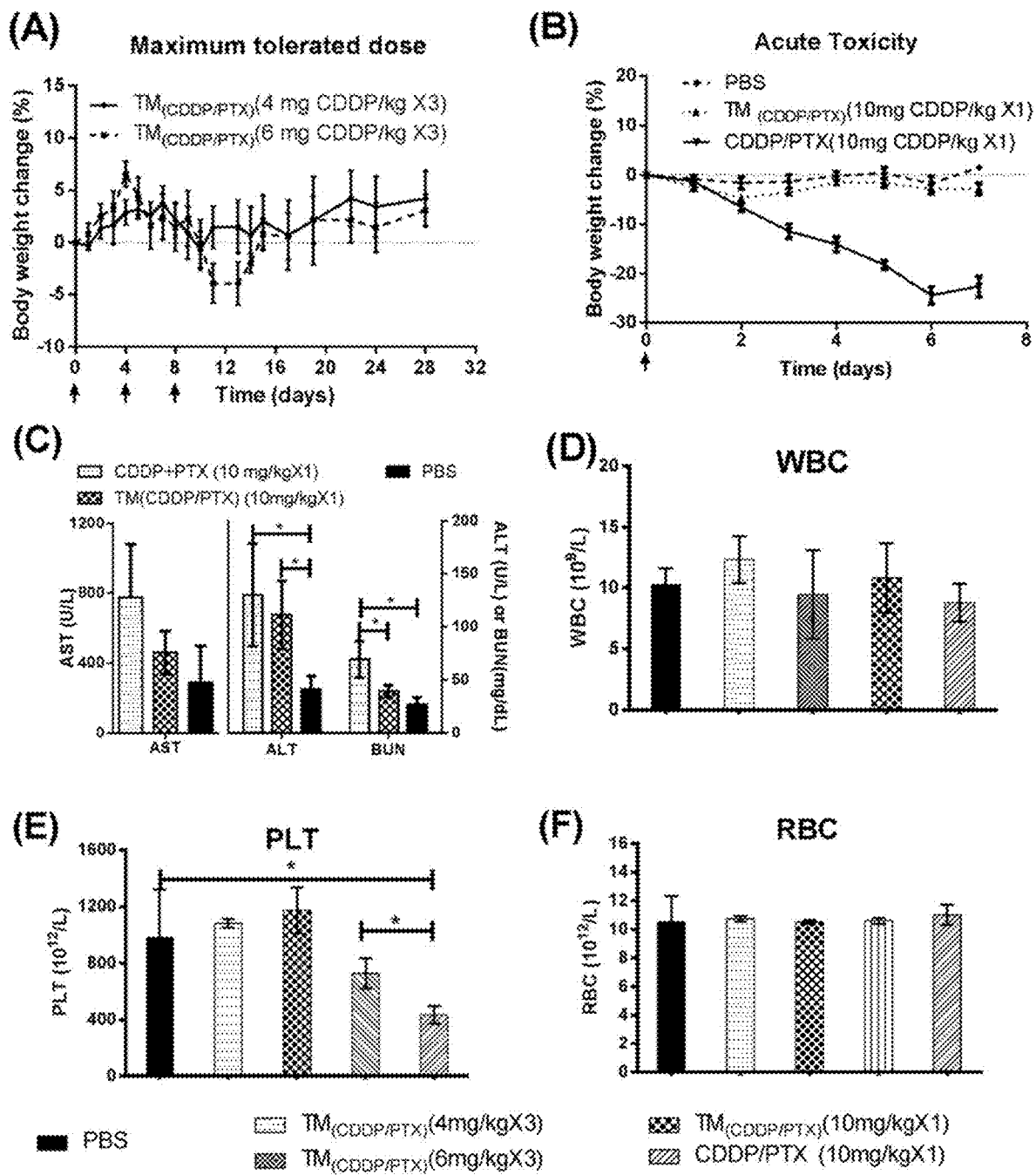
FIG. 7. (A) The body weight changes for animals treated with $TM_{(CDDP/PTX=2:1)}$ at two dosage levels, e.g., 4 and 6 mg CDDP/kg for three dosage in MTD study; (B) the body weight changes of animals treated with a single dose of free drug mixture of CDDP/PTX 2:1 w/w and $TM_{(CDDP/PTX=2:1)}$ at 10 mg CDDP/kg level in comparison with PBS control group; (C) the serum AST and ALT enzyme levels and BUN level of animals in the acute toxicity studies treated with free CDDP/PTX and $TM_{(CDDP/PTX=2:1)}$, respectively, at 10 mg CDDP/kg level; The blood cell counting analysis for WBC (D), PLT (E) and RBC (F) for the mice in MTD and acute toxicity studies. (*: p<0.05).

In addition, complete blood counting analysis on day 7 revealed decreased amounts of platelets among mice treated with free drug mixtures (CDDP/PTX) compared with the control group or TM$_{(CDDP/PTX=2:1)}$ group (P<0.05) (FIG. 6D-F). Furthermore, administration of free drug mixture resulted in a significant increase of plasma blood urine nitrogen (BUN), aspartate aminotransferase (AST), and alanine aminotransferase (ALT). These values were, however, much lower in mice treated with TM$_{(CDDP/PTX=2:1)}$ (FIG. 6C), indicating the lower hepatotoxic and renal effects for micellar formulation. The free drug combination of CDDP/PTX at such high dosage of 10 mg/kg significantly increased the BUN level compared with control group and TM$_{(CCP/PTX=2:1)}$ group (p<0.05), whereas no significant difference was observed between the latter two groups. This indicates relatively low renal dysfunction in animals treated with TM$_{(CDDP/PTX=2:1)}$. Furthermore, microscopic analysis of the liver and renal parenchyma showed that both organs did not have any morphological changes after the treatment with TM$_{(CDDP/PTX=2:1)}$, compared with control group (FIG. 7). After being treated with PBS (control), free CDDP/PTX and TM$_{(CDDP/PTX=2:1)}$ at 10 mg CDDP/kg tissues were stained with fixed with 4% paraformaldehyde and stained with hematoxylin and eosin (H&E). Significant tubular dilation with flattening of the epithelium cells were observed only in the kidneys in mice treated with free CDDP/PTX mixture. No abnormal structures were observed in livers.

Together, these results indicate that the nanoparticle enhances the circulation of the drug and reduces the cytotoxic effects on vital organs.

Figure 8:
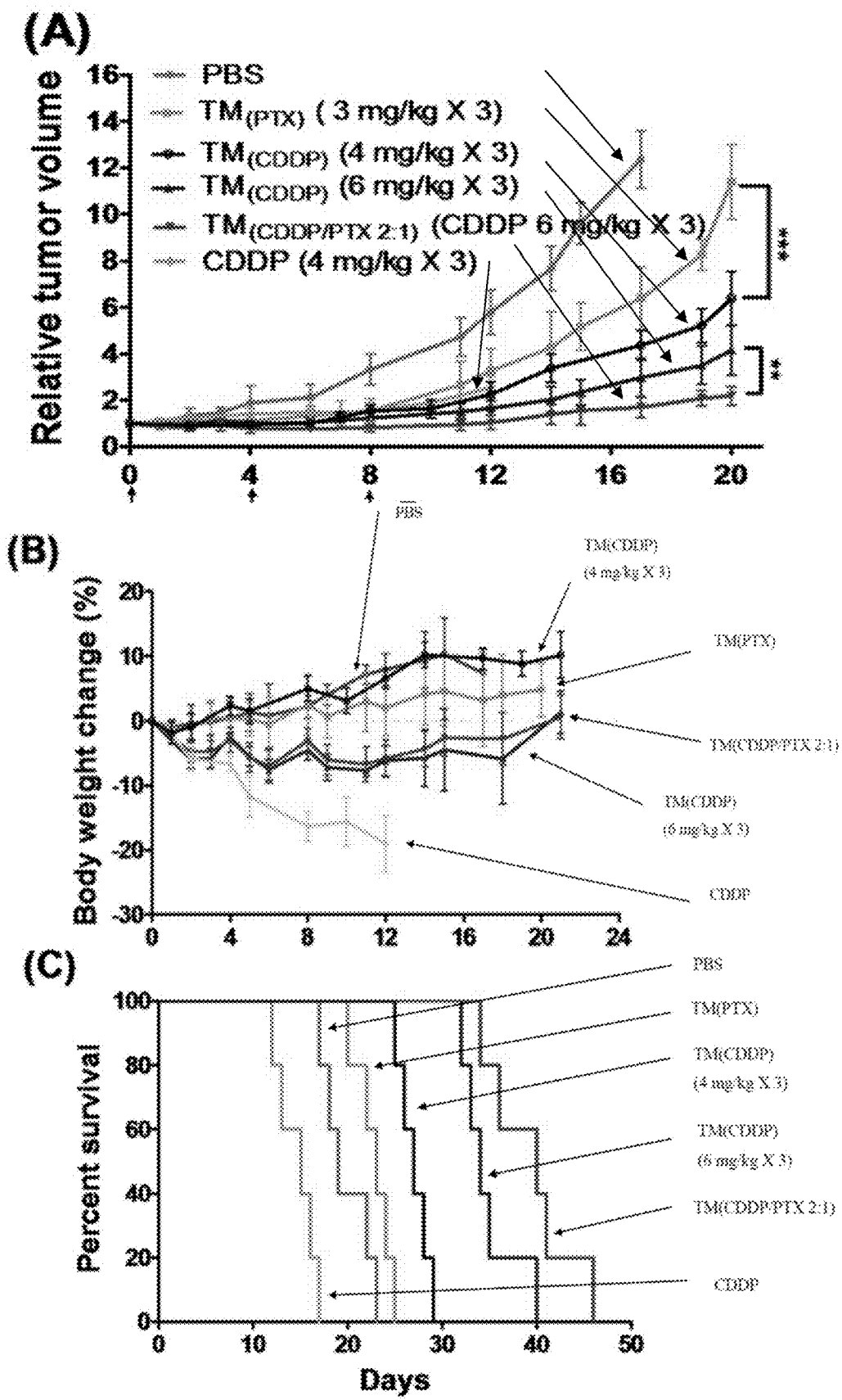
FIG. 8. In vivo tumor growth inhibition (A), body weight changes (B) and Kaplan-Meier survival curve (C) of mice beard SKOV-3 ovarian cancer xenografts (n=5) after intravenous treatment with different CDDP and PTX formulations (on day 0, 4, 8).

In vivo anticancer efficacy: To test the efficacy of our design, we delivered various nanoparticle formulations to xenografted nude mice with ovarian cancer SKOV-3. Animals were randomly separated into six groups (n=5) and treated with single or combination therapeutics, e.g., free CDDP (4 mg/kg CDDP), TM$_{(PTX)}$ (3 mg/kg), PEG$_{(CDDP)}$ (4 mg/kg), TM$_{(CDDP)}$ (6 mg/kg), and TM$_{(CDDP/PTX\ 2:1)}$ (6 mg/kg CDDP & 3 mg/kg PTX), as well as PBS control. Three dosages of drugs and PBS were administered intravenously on days 0, 4, and 8. Tumor growth inhibitions, body weight changes, and survival rates of the SKOV-3 tumor bearing mice in the different groups were monitored for more than 45 days (FIG. 8). Excepting the free CDDP group, all the mice in the treatment groups tolerated the treatment well with an initial body weight loss of less than 10%, followed by recovery of body weight after day 16 (FIG. 8B). However, the body weight loss of mice in the free CDDP treatment group (4 mg/kg) exceeded 20% on day 12 and the mice died due to the toxicity of free CDDP treatment. On day 7 after the last injection, blood samples were collected for blood cell counting analysis. Compared to the PBS control group, the WBC count in the free CDDP group was significantly decreased (p<0.01), indicating myelosupression. The RBC and PLT in all treatment groups were observed within the normal range.

Unfortunately, all animals in the free CDDP group at 4 mg/kg died, with the deaths occurring on day 12, 13, 15, 16 and 17, due to side effects as observed in FIG. 8. Low dose TM$_{(PTX)}$ (3 mg PTX/kg) showed mild tumor inhibitory effects compared with the control group. At the same time, CDDP loaded in TMs exhibited a dose dependent tumor inhibition, which was significantly better than TM$_{(PTX)}$ treatment even at a low dose of 4 mg of CDDP/kg. More importantly, TM$_{(CCP/PTX=2:1)}$ (6 mg/kg CDDP/3 mg/kg PTX) exhibited better tumor growth inhibition (P<0.05) than TM$_{(CDDP)}$ (6 mg/kg CDDP). On day 28, the median relative tumor volume (RTV) was 2.5 for mice treated with TM$_{(CDDP/PTX=2:1)}$, while the RTVs for mice treated with TM$_{(CDDP)}$ (4 mg/kg CDDP) and TM$_{(CDDP)}$ (6 mg/kg CDDP) were 11.4 and 5.2, respectively. Superior tumor inhibition of TM$_{(CDDP/PTX=2:1)}$ could be due to the synergism effect between CDDP and PTX as studied in vitro. For humane reasons, animals were euthanized when the implanted tumor volume reached 2000 mm$^3$, which was considered as the end point of survival data. The mice survival rates in each group are presented by the Kaplan-Meier survival curve, respectively (FIG. 8C). In general, compared to PBS control, all the CDDP loaded TM formulations significantly prolonged the survival times of tumor bearing mice. The medium survival time for animals treated with PBS, CDDP (4 mg/kg), TM$_{(PTX)}$ (3 mg/kg), TM$_{(CDDP)}$ (4 mg/kg), TM$_{(CDDP)}$ (6 mg/kg) and TM$_{(CDDP/PTX)}$ (6 mg CDDP+3 mg PTX/kg) were 19, 15, 23, 27, 34 and 40 days, respectively. The nano-combination cohort TM$_{(CDDP/PTX=2:1)}$ exhibited longest survival time than all other groups.

We engineered a three-layered telodendrimer (linear-dendritic polymer) nanocarrier for the effective co-delivery of CDDP and PTX as an ovarian cancer combination therapy. The programmed faster release of PTX than CDDP from the nanoformulation with the optimized drug loading ratio enables the synergism in killing ovarian cancer cells in vitro. The stable nanocarrier significantly prolonged the drug delivery in the systemic circulation and reduced the renal toxicity of CDDP. The optical imaging and Pt-biodistribution analysis indicated that telodendrimer micelles were concentrated within tumor sites favorably than in the normal organs. The targeted drug delivery, the increased tolerated dosage and the synergistic combination of CDDP/PTX within telodendrimer nanocarrier enhanced survival of mice harboring ovarian cancers.

EXAMPLE 2

This example describes the co-delivery of Doxorubicin and Bortezomib co-delivery using telodendrimers of the present disclosure.

Figure 9:
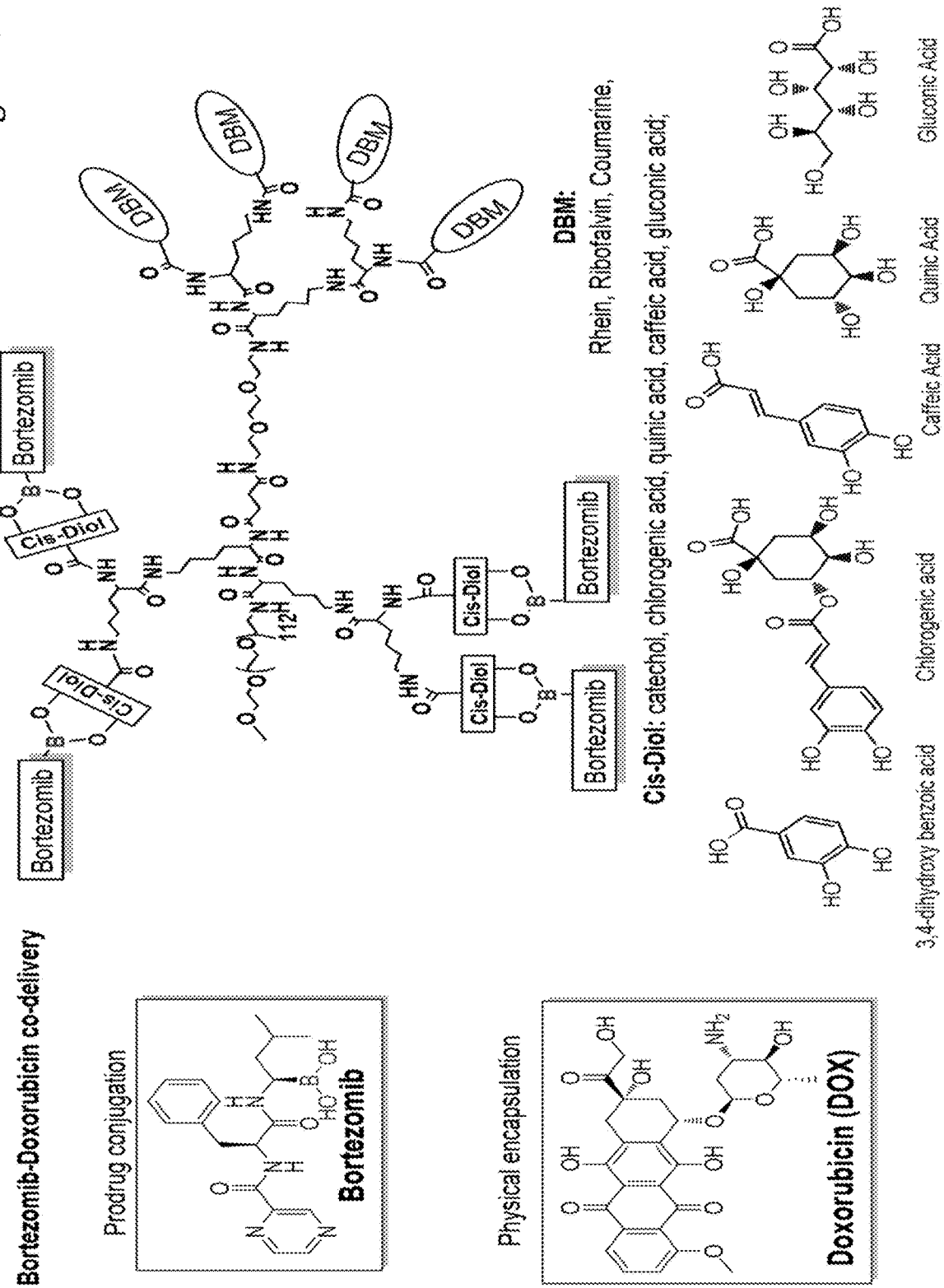
FIG. 9. Schematic illustration of a telodendrimer design for Doxrubicin and bortezomib co-delivery.

Doxorubicin and Bortezomib co-delivery. Functional telodendrimers for co-delivery of hydrophilic drug and hydrophobic drug molecules. We rationally designed and developed novel telodendrimer micelle system to co-deliver Bortezomib and Doxorubicin (FIG. 9). Three layered telodendrimer has been designed as shown in FIG. 19. The various length of polyethylene glycol (at left end of molecule) serves as hydrophilic segments of the telodendrimer; the adjacent layer was composed of branched architecture capped with functional groups (in the present case, Cis-Diol) for the conjugation of specific drugs or gene molecules (in the present case, BTZ) via labile linkages, reversible complexes or multivalent charge interactions; the peripheral of the proximal dendrimer (right end of molecule) were specifically decorated with drug binding moieties (DBMs) for hydrophobic drug loading (in the present case, DOX) via physical encapsulation. Among the cis-diols that could be used for conjugating BTZ to the telodendrimer are catechol, chlorogenic acid, quinic acid, caffeic acid and gluconic acid. Among the DBMs that could be used for binding DOX to the telodendrimer are rhein, riboflavin and coumarin.

Figure 10:
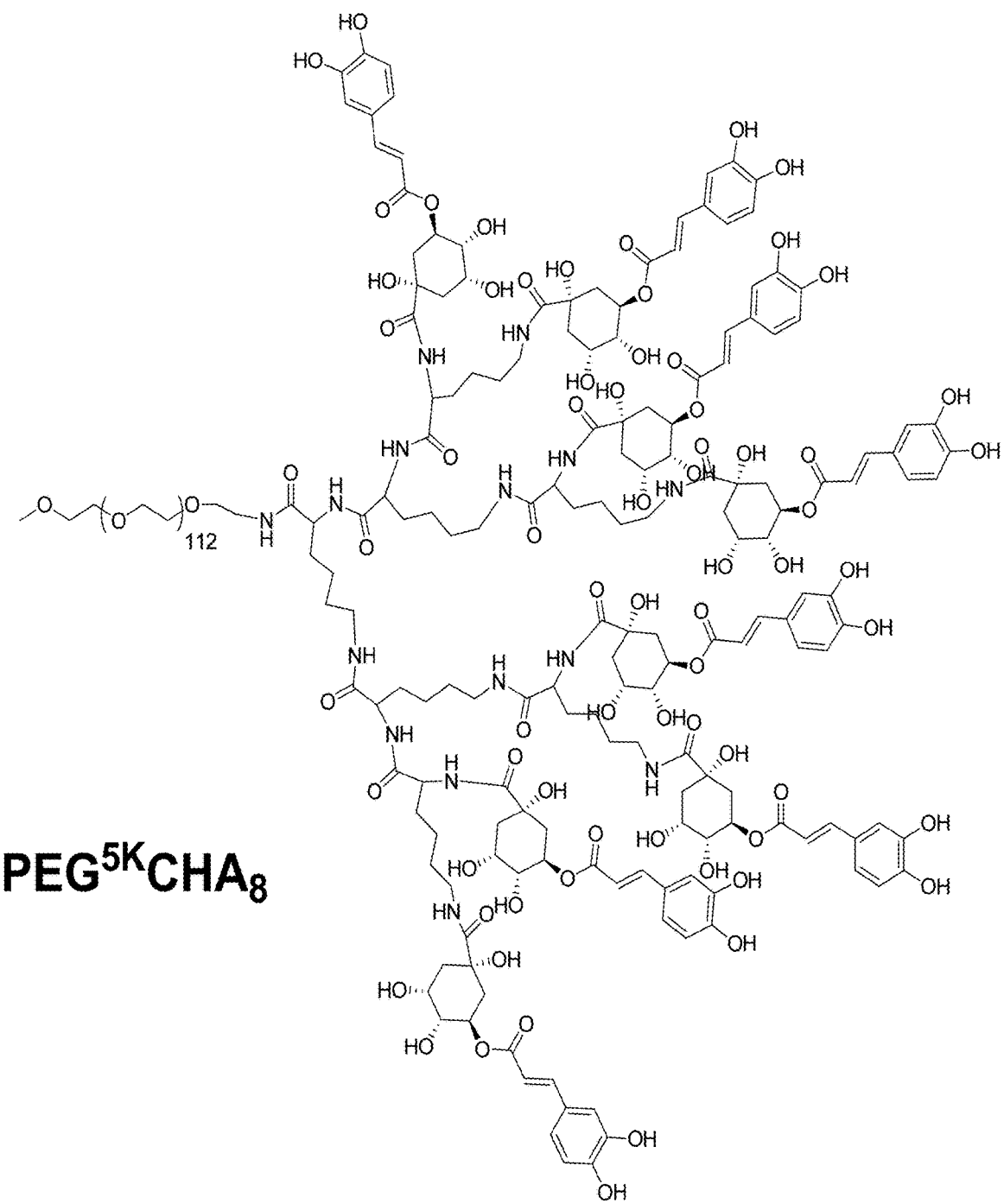
FIG. 10. The structure of telodendrimer $PEG^{5k}CHA_8$ with eight CHA as peripheral groups for, e.g., botezomib delivery.
Figure 11:
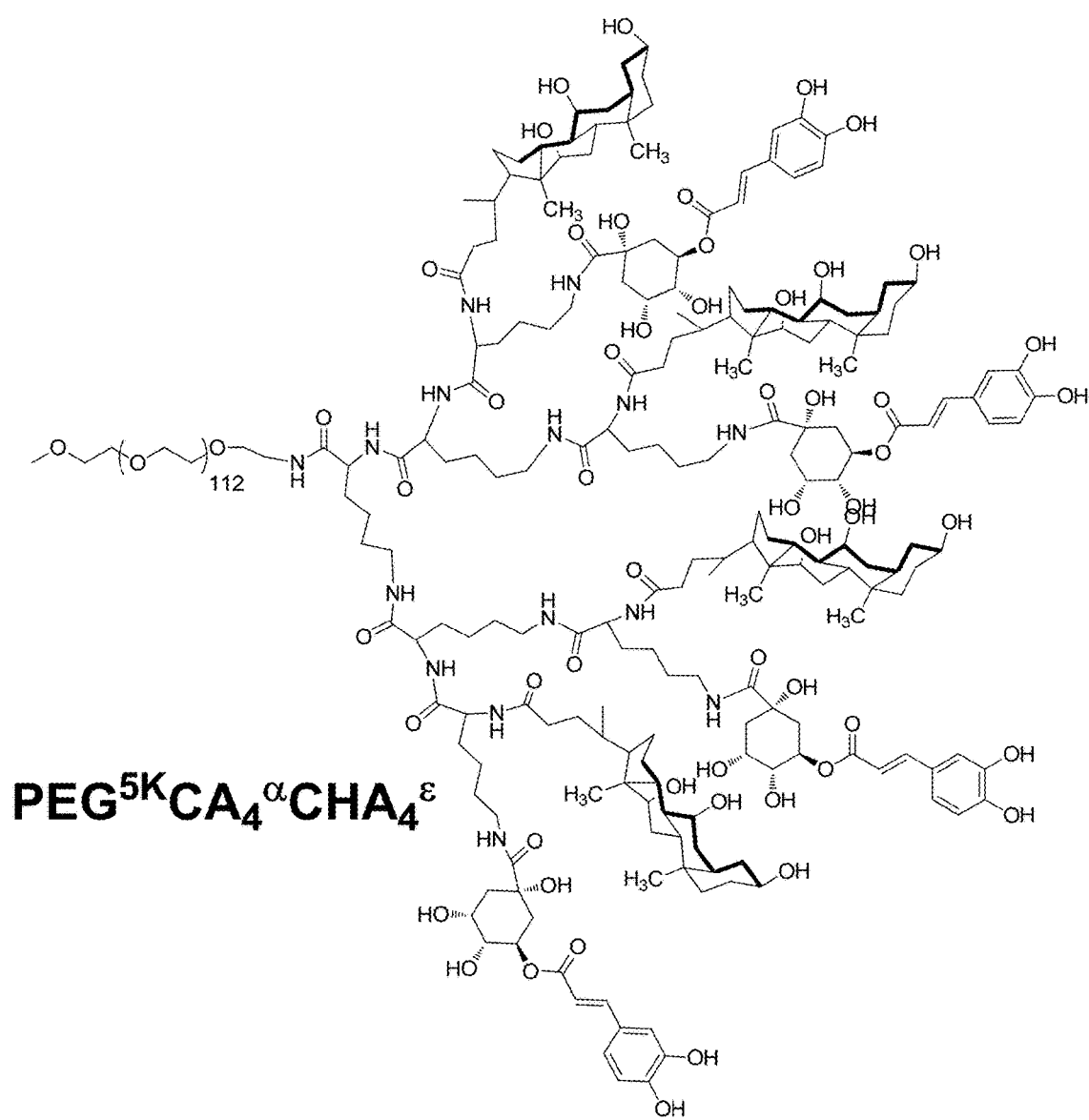
FIG. 11. The structure of telodendrimer $PEG^{5k}CA_4CHA_4$ with alternating CHA and CA as peripheral groups for, e.g., botezomib delivery.

Synthesis. The nomenclature of the telodendrimers follows the following example, telodendrimer PEG$^{5K}$CHA$_4$-L-Rh$_4$ indicates that the molecular weight of PEG is 5 kDa and there are four chlorogenic acid molecules (CHA) conjugated on the adjacent layer; four rhein (Rh) molecules are conjugated at the distal peripheral of the telodendrimer and are segregated with a triethylene glycol linker molecule (L). PEG$^{5K}$CHA$_8$ (FIG. 10) and PEG$^{5K}$CA$_4$CHA$_4$ (FIG. 11) were synthesized via a solution-phase condensation reactions starting from MeO-PEG$^{5k}$-NH$_2$ (5000 Dalton) via stepwise peptide chemistry following a previous procedure, and proton NMR was used to characterize the structures of telodendrimer.

The synthesis of PEG$^{5K}$CHA$_4$-L-Rh$_4$ (FIG. 12) is briefly described as following: (Fmoc)Lys(Boc)-OH was coupled onto the terminal amino group on PEG by using DIC and HOBt as coupling reagents until a negative Kaiser test result was obtained, which indicated the completion of the coupling reaction. PEGylated molecules were precipitated by pouring reaction solution into excess amounts of cold ether, followed by centrifugation and then wash with cold ether one or two times. The white powder precipitate was dried under reduced pressure and the Fmoc protection group was removed by using 20% methylpiperidine solution in DMF and then the polymer was precipitated. Second coupling of (Fmoc)Lys(Boc)-OH was coupled repeatedly. After removal of Fmoc groups, Fmoc protected triethylene glycol linker molecule was coupled to the terminal amino groups. Then two respective couplings of (Fmoc)Lys(Fmoc)-OH were carried out subsequently to generate a dendritic polylysine terminated with four Fmoc groups and two Boc-protected amino groups at the adjacent sites of polymer.

Figure 12:
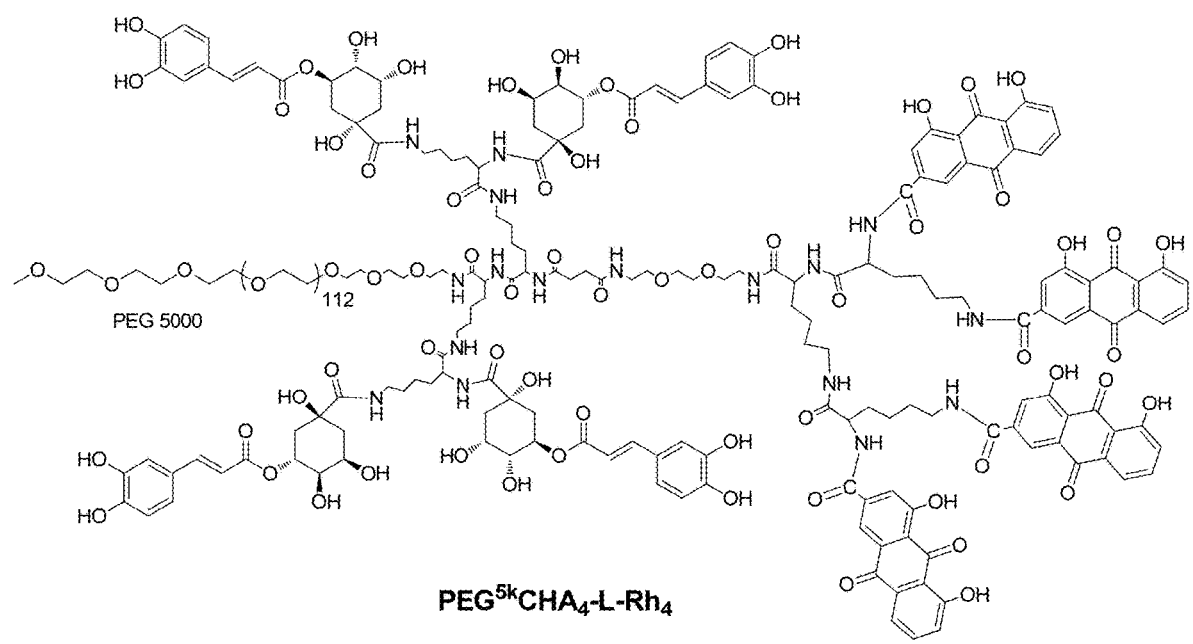
FIG. 12. The structure of telodendrimer $PEG^{5k}CHA_4$-L-$Rh_4$ with adjacent chlorogenic acid-containing domain and a proximal Rhein-containing Dendron, e.g., for bortezomib and doxorubicin/daunorubicin delivery.

In addition, PEG$^{5K}$-(NH-Boc)$_4$-L-(NH-Fmoc)$_4$ was obtained via coupling of (Boc)lys(Boc)OH onto the adjacent amino groups of the telodendrimers after removal of two Boc groups with 50% (v/v) trifluoroacetic acid (TFA) in dichloromethane (DCM). Four chlorogenic acid-NHS esters were coupled on the amino groups after removal of the Boc groups by using HOBt/DIC as coupling reagents to form PEG$^{5K}$(CHA)$_4$-L-(NH-Fmoc)$_4$. Rhein-NHS esters were then coupled to the Fmoc-functionalized amino groups of dendritic polylysine after removal of the Fmoc group to yield telodendrimer PEG$^{5K}$CHA$_4$-L-Rh$_4$ (FIG. 12). Proton NMR was recorded to characterize the structure of the telodendrimer.

DOX loading in PEG$^{5K}$CHA$_4$Rh$_4$. DOX could be loaded in these newly developed telodendrimer micelles via thin-film dispersion method. The particle sizes of the newly formed micelles were determined by DLS particle sizer at 2 mg/mL concentrations in PBS. DOX-PEG$^{5K}$CHA$_4$Rh$_4$ exhibit mono-dispersed particle sizes of 31.2±9.13 nm at 0.5/5 mg/mL DOX/polymer concentration. The DOX loaded micelles was stable upon storage at 4° C. for month without significant particle size changes. The critical micellization concentration CMC of PEG$^{5K}$CHA$_4$Rh$_4$ micelle was decreased from 45 µg/mL to 2 µg/mL after DOX loading.

BTZ loading in CHA containing micelles. BTZ was incubated with CHA containing telodendrimers in chloroform and then solvent was dried via roto-evaporation. Then PBS was added to disperse the complex into micelles. Bortazomib-loaded PEG$^{5K}$CHA$_8$ at 0.5/5.0 mass ratio was observed to form large and heterogeneous micelles, 131.2 nm (70.3%) and 392.0 nm (29.7%) indicating the poor loading property. Further, BTZ was loaded into PEG$^{5K}$CA$_4$CHA$_4$ telodendrimer. The particle sizes were observed to be homogenous of 28.01+/−9.11 nm at a 0.5:5.0 mass ratio. Further, the particle sizes were increased to 112.5+/−39.60 nm with the increased drug loading content at 1.0:5.0. Furthermore, BTZ was loaded in PEG$^{5K}$CHA$_4$-L-Rh$_4$ at a 0.5:5.0 mass ratio and the particle sizes was observed to be 13.49+/−3.13 nm, which was almost the same as empty micelles.

BTZ-DOX co-loading. 0.5 mg of BTZ and 5 mg of telodendrimer PEG$^{5K}$CHA$_4$-L-Rh$_4$ were dissolved in chloroform and incubated overnight. Then 0.5 mg of DOX was added into the mixture solution together with 3 equivalents of TEA. Then, solvent was dried and the mixture film is dispersed into 1 mL of PBS. The particle size was analyzed via DLS to be 60.0+/−33 nm.

Photocrosslinking. PEG$^{5K}$CHA$_4$-L-Rh$_4$ was tested for photocrosslinking abilities via the dimerization of caffeic acid in CHA. Cross-linked telodendrimers were shown to be more effective at drug-carrying because they are more stable than non-crosslinked telodendrimers after forming into micelles, which can prematurely release the loaded drug in the event of an environmental stimulus. A 2 mg/ml sample of PEG$^{5K}$CHA$_4$LRh$_4$ dissolved in pure water was UV (300 nm) irradiated for over 6 hours total in small time increments and crosslinking was measured via the UV-Vis Nanodrop at 320 nm. The crosslinking degree appeared to reach a plateau about 50-60% after 200 min UV exposure. The particle sizes remained almost the same about 10-11 nm before and after crosslinking.

Figure 13:
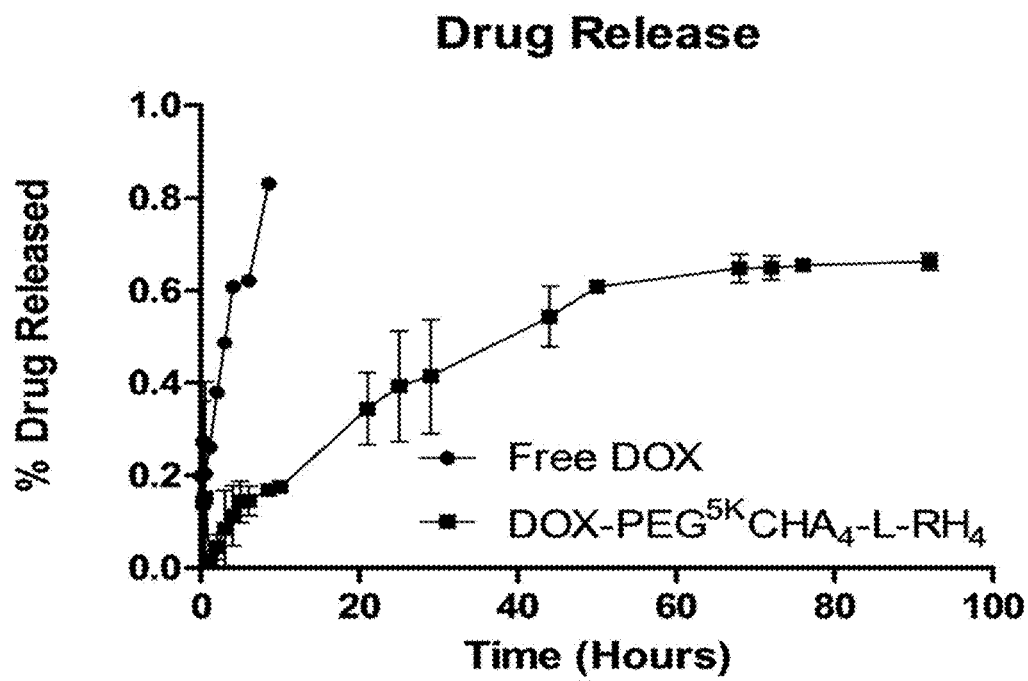
FIG. 13. Drug release for DOX-$PEG^{5K}CHA_4$-L-$Rh_4$ compared to free DOX in PBS measured at 550 nm.

DOX Release. 1 mL of DOX-PEG$^{5K}$CHA$_4$-L-Rh$_4$ (1.5: 15.0) solution was distributed into three dialysis tube and dialyzed against 50 ml PBS at 37° C., respectively, in comparison with free DOX. The samples were placed in conical tubes filled with PBS, which was refreshed at the time of UV-Vis measuring at 550 nm (FIG. 13). The free DOX was completely released by 10 hours but the loaded DOX remained encapsulated at around 50% by the time the study was finished at 96 hours. This indicates the high DOX binding affinity within PEG$^{5K}$CHA$_4$-L-Rh$_4$ micelles and a sustained DOX release would reduce in vivo toxicity of payload drug and increase tumor targeting effects via the prolonged circulating to take EPR effects.

Figure 14:
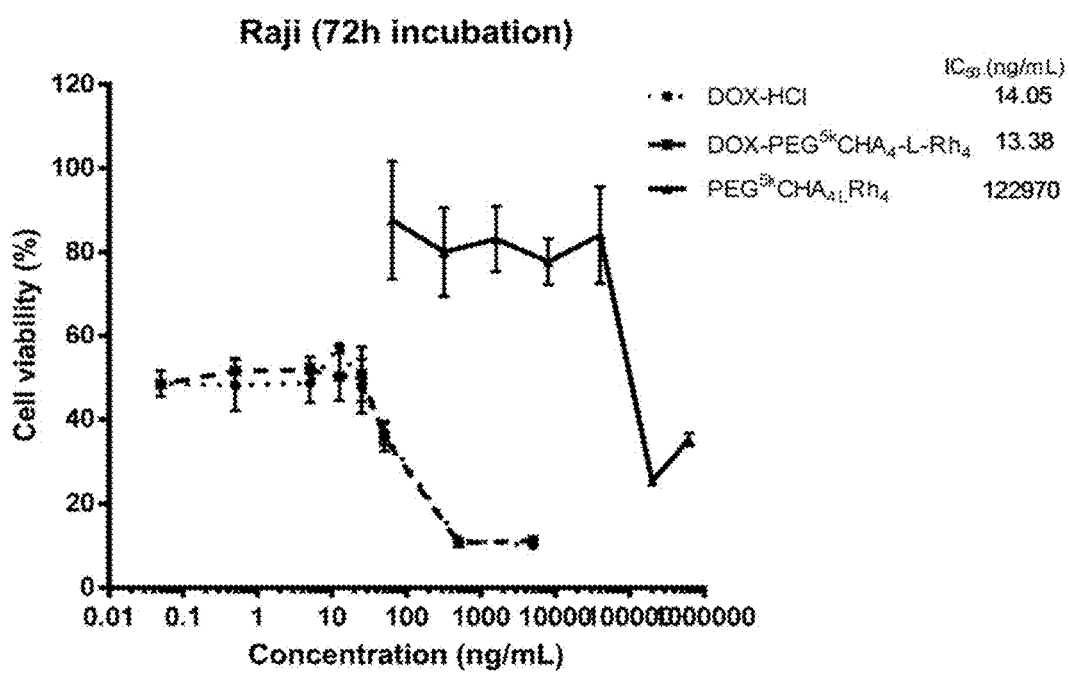
FIG. 14. MTT Assay of DOX loading in $PEG^{5K}CHA_4$-L-$Rh_4$ compared with free DOX, free polymer, and DOX-loaded polymer.
Figure 15:
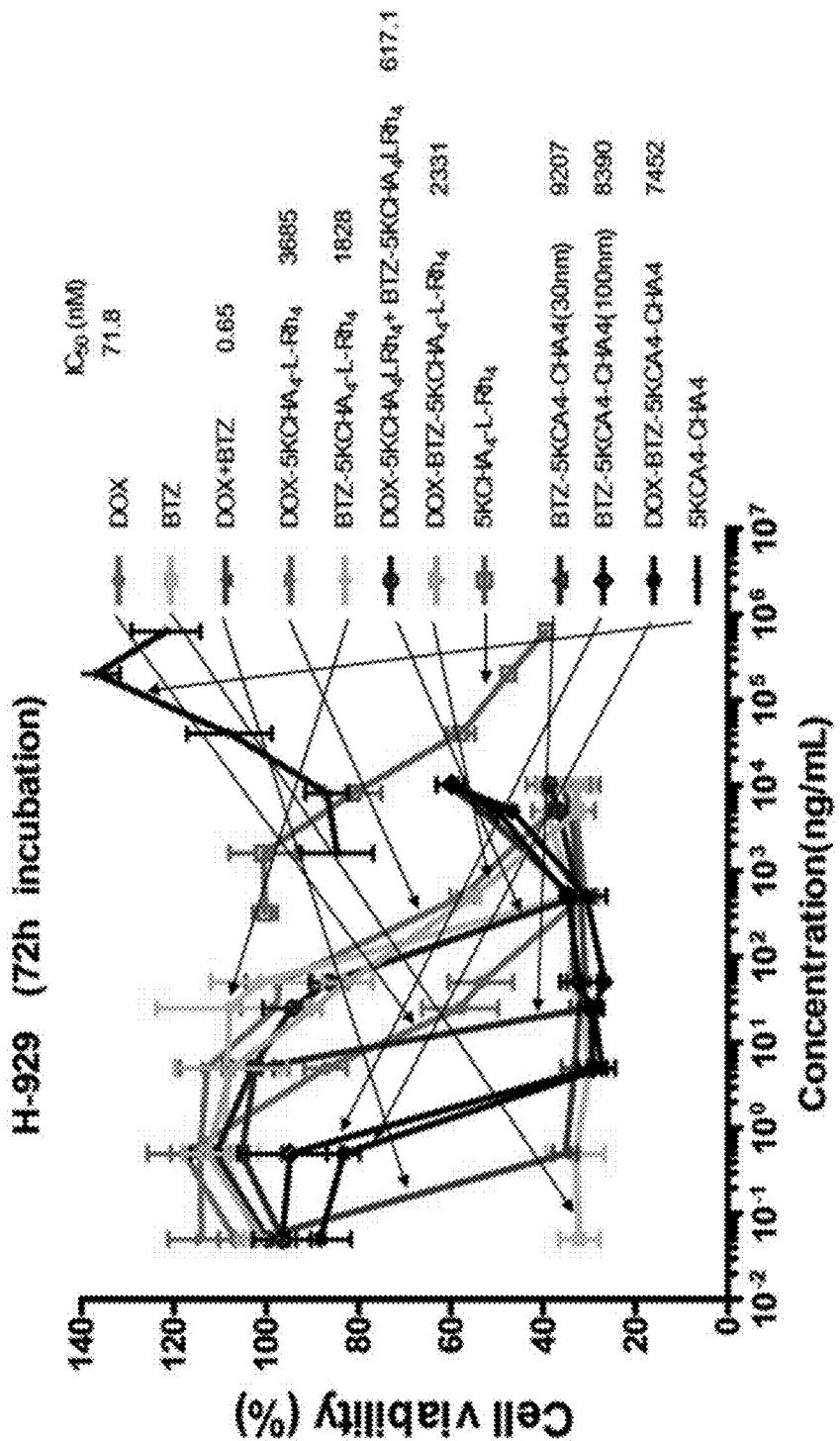
FIG. 15. MTT Assay comparing single to co-loading DOX and BTZ comparing free DOX, free BTZ, single-loaded DOX, single-loaded BTZ, mixture of free DOX and BTZ, mixture of single loaded DOX and BTZ, co-loaded DOX and BTZ, and free polymer.

MTT Assay. Raji lymphoma cell line (FIG. 14) and multiple myeloma cells H929 (FIG. 15) were used to evaluate the cytotoxicity of empty micelles and drug loaded micelles. Empty PEG$^{5K}$CHA$_4$Rh$_4$ micelle exhibit noncytoxic up to 0.5 mg/mL; however, PEG$^{5K}$CHA$_4$-L-Rh$_4$ exhibited mild cell growth inhibition at 10 ug/mL level. It was observed that DOX and BTZ loaded in the nanocarrier showed reduced cytotoxicity compared with the free drug molecule, which may due to the stable drug encapsulation. However, it may not necessary indicate the loss of activity in vivo. On the contrary, the stable drug encapsulation could minimize premature drug release and increase tumor targeted drug delivery. The in vivo biological and pathological environment may induce drug release more efficiently via the hydrophobic interactions of the micelles with hydrophobic molecules. Therefore, it is expected that reduced toxic side effects and enhanced anticancer effects can be achieved in vivo via these stable drug formulations. The further systematic optimization and in vivo characterization will be performed in future.

Novel co-delivering telodendrimers were developed using chlorogenic acid as functional reactive building block and rhein as drug binding molecule to form nanocarriers for single-loading and co-loading Bortezomib and Doxorubicin. The stable drug loaded nanoformulations were developed with small particle sizes and narrow drug distributions. The slow drug release and prolonged stability indicate the functional segregated telodendrimer could be a promising nanocarrier for the co-delivery of the chemodrugs as the combination nanotherapeutics. The novel design of nanocarriers for the co-delivery of both hydrophobic and hydrophilic drug molecules via the spatial segregated functionalities within the telodendrimers was demonstrated.

EXAMPLE 3

This example describes the co-delivery of gene molecules and anticancer drugs using cationic telodendrimers of the present disclosure.

Figure 16:
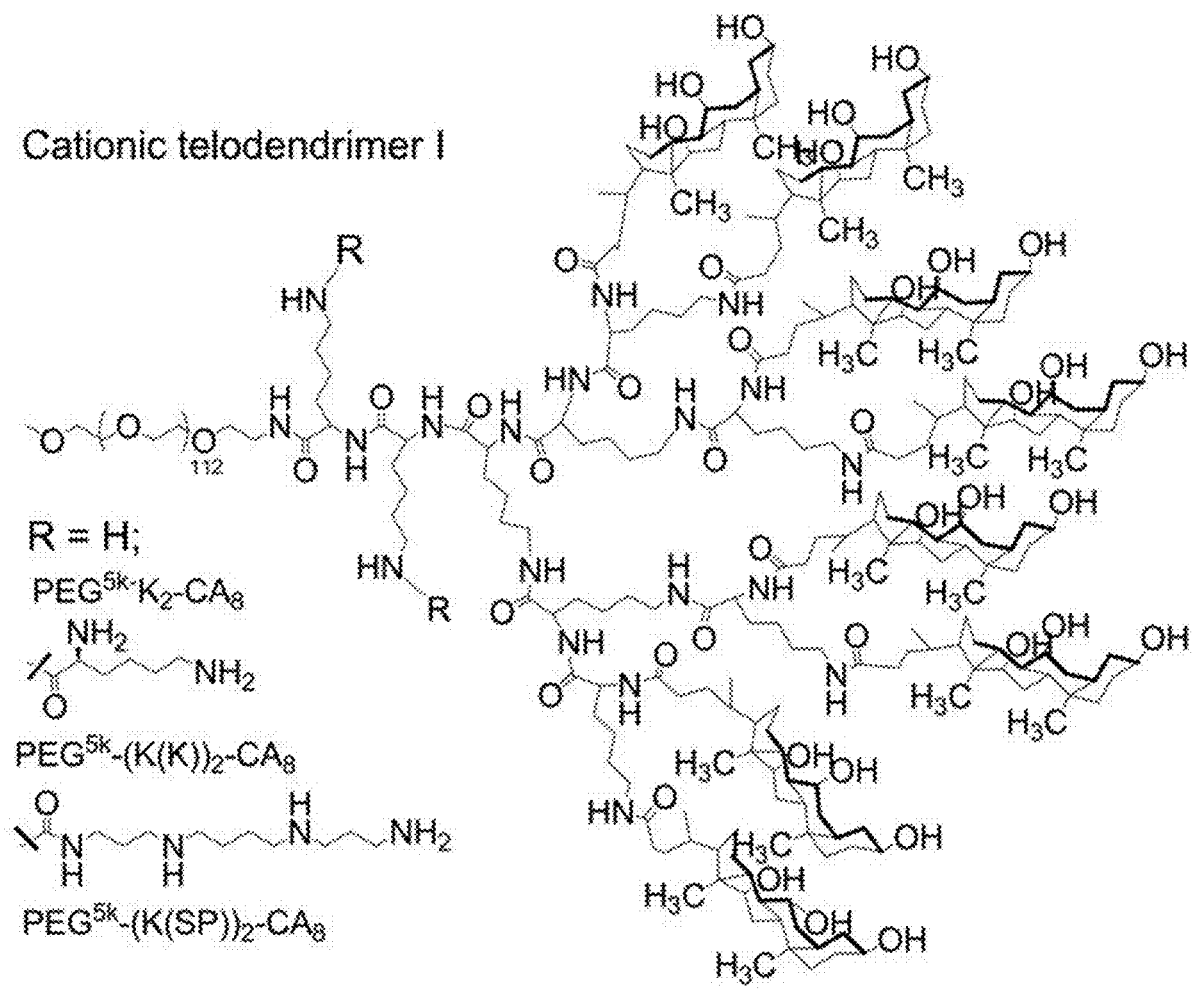
FIG. 16. The chemical structure of a series of cationic telodendrimers with the positive charged amines decorated in the adjacent layer sites of telodendrimer.

Co-delivery of gene molecules and anticancer drugs Cationic telodendrimer micelles for co-delivery of gene and anticancer drugs. The general cationic polymeric vehicles for gene delivery exhibit significantly cytotoxicity and non-specificity due to an excess of positive charges. Telodendrimers self-assemble into micellar nanoparticles via hydrophobic interactions with the outer PEG layer making these nanoparticles nontoxic up to 1 mg/mL concentration. The introduction of polyamines into the intermediate layer of the micelle enables the delivery of DNA while maintaining the micelle formation for co-loading hydrophobic anticancer drugs in the nanoparticle core. We developed two series of cationic telodendrimers: cationic telodendrimer I series has positive charged polyamines in the adjacent site of the telodendrimer, (FIG. 16) which may have distinct spatial segregation between the core and shell in the micelles.

Figure 17:
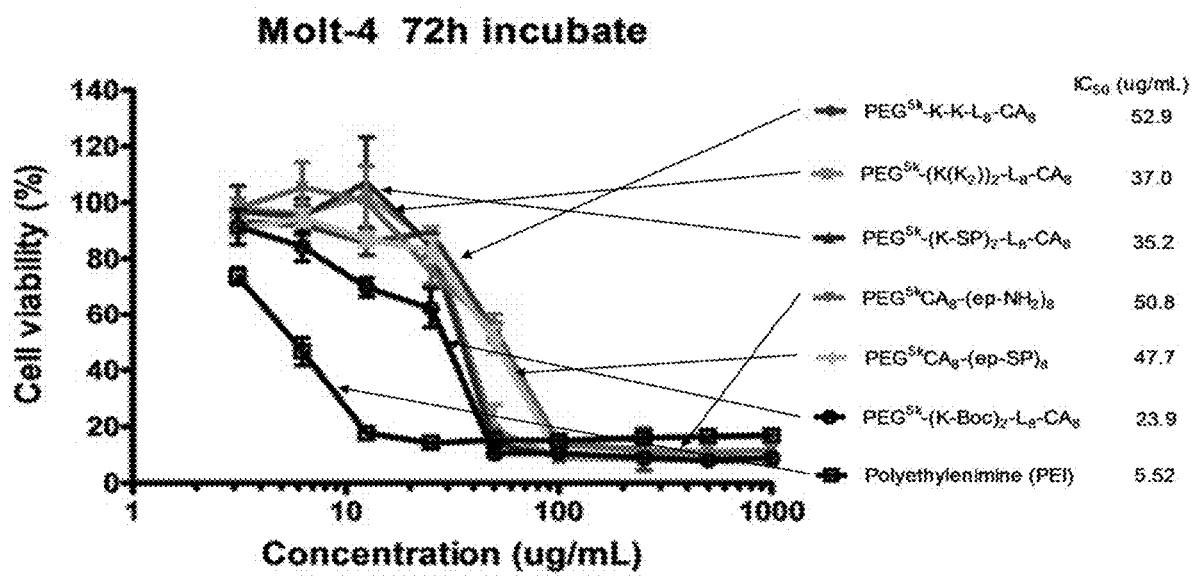
FIG. 17. The cytotoxicity of examples of cationic telodendrimers and PEI in cell culture against Molt-4 lymphoma cell line. The cell viability was analyzed via MTS assays.
Figure 18:
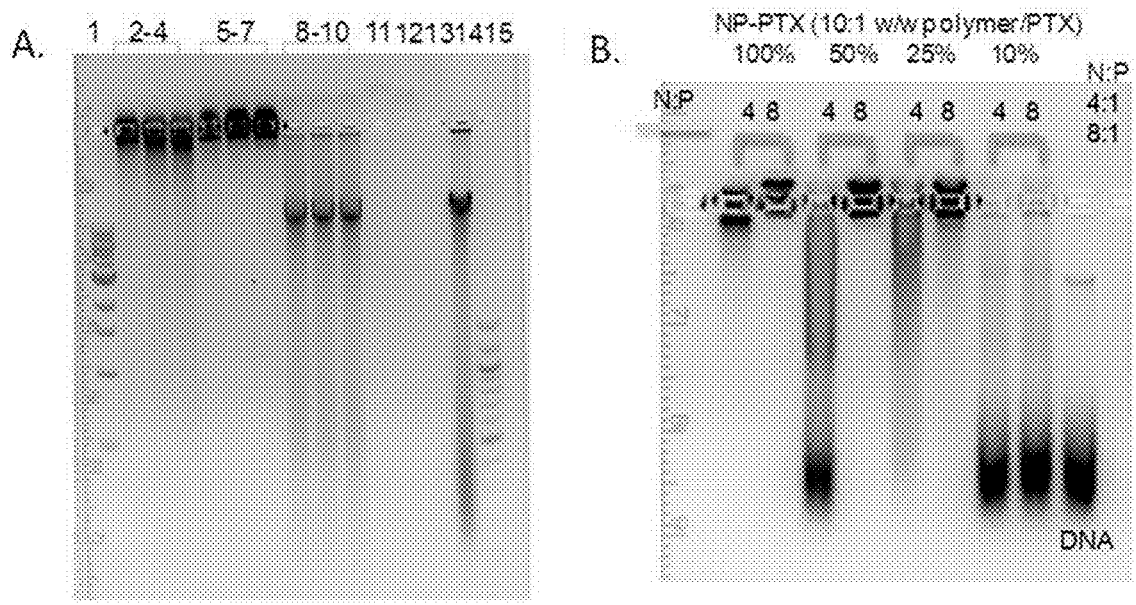
FIG. 18. (A) Agarose gel electrophoresis of the complex of fragmented salmon sperm DNA with the cationic telodendrimer PEG$^{5k}$CA$_8$-SP (lanes 2-4 N/P: 33:1; lanes 5-7 N/P: 66:1) and PEG$^{5k}$CA$_8$(lane 8-10 20:1 w/w Polymer/DNA) after incubation at different conditions: room temperature (rt) overnight (Lanes 2, 5 & 8); 4° C. overnight (Lanes 3, 6 & 9); rt 30 min (Lanes 4, 7 & 10). Lanes 11-13 were telodendrimers alone (lane 11: PEG$^{5k}$CA$_8$-SP; lane 12: PEG$^{5k}$CA$_8$; lane 13: PEG$^{5k}$CA$_8$-S—NH$_2$) and the fragmented DNA control (lane 14). (B) Agarose gel electrophoresis of the complex of fragmented salmon sperm DNA with the cationic telodendrimer PEG$^{5k}$CA$_8$-SP doped with different amount of neutral telodendrimer PEG$^{5k}$CA$_8$ and loaded with 10% of paclitaxel (PTX).

In order to minimize the cytotoxicity of the cationic telodendrimers, the endogenous amines, such as lysine and spermine were utilized for introducing positive charges. As shown in FIG. 17, the three layered cationic telodendrimer exhibited almost 10-fold less toxicity than PEI in cell culture with lymphoma Molt-4 cell lines. As shown in FIG. 18, the incubation conditions of fragmented salmon sperm DNA with cationic telodendrimers PEG$^{5k}$CA$_8$-SP were optimized. It was shown that a short incubation time of 30 min at room temperature is as efficient as overnight incubation at room temperature or 4° C. A certain amount of DNA molecule was loaded in the core-inversed PEG$^{5k}$CA$_8$ micelles in organic solvent. However, DNA was not sustained in the neutral telodendrimer micelles during electrophoresis, indicating the essential charge interactions for nucleotide delivery. Further, the 10 weight % of PTX was loaded into telodendrimer micelles formed with various amounts (e.g., 100%, 50%, 75% and 10%) of spermine containing telodendrimer and the neutral PEG$^{5k}$CA$_8$. The drug-loaded, positively charged micelles were incubated with fragmented DNA molecules at N/P ratios of 4:1 and 8:1 respectively. The electrophoresis indicated that 25% of SP telodendrimer with an 8:1 N/P ratio is efficient for DNA encapsulation. The fragmented salmon sperm DNA via sanitation was observed to have two main fractions: one has a size similar to plasmid DNA of about 10-100 Kbps; another fragment is mainly smaller than 500 bps, which is the range of siRNA, RNAi and antisense DNA. As shown in FIG. 18, both of these two bands were efficiently loaded into the cationic telodendrimer micelles, indicating the potential application of this vehicle in both plasmid DNA and siRNA delivery. The particle sizes and zeta potential of these cationic telodendrimers were characterized as shown in Table 4. The particle sizes increased to about 20 nm after being loaded with DNA molecules and the zeta potential decreased and became negative after being loaded with DNA molecules, which will minimize the cytotoxicity of the nanoparticle.

TABLE 4

The particle sizes and zeta potential of cationic telodendrimer before and after loaded with fragmented DNA molecules

| | paticle size (nm) | Zeta Potential (mV) |
|---|---|---|
| PEG$^{5K}$-K-K-L$_8$-CA$_8$ | 7.7 | 77.62 |
| PEG$^{5K}$-(K(K$_2$))$_2$-L$_8$-CA$_8$ | 4.2 | |
| PEG$^{5K}$-(K-SP)$_2$-L$_8$-CA$_8$ | 6.8 | 19.6 |
| PEG$^{5K}$-K-K-L$_8$-CA$_8$ + DNA (N:P = 1:1; w:w = 16:1) | 24.8 | 17.81 |
| PEG$^{5K}$-K-K-L$_8$-CA$_8$ + DNA(N:P = 0.5:1; w:w = 8:1) | 18.5 | −16.73 |
| PEG$^{5K}$-(K(k$_2$))$_2$-L$_8$-CA$_8$ + DNA(N:P = 1:1; w:w = 8:1) | 22.1 | |
| PEG$^{5K}$-(K(k$_2$))$_2$-L$_8$-CA$_8$ + DNA(N:P = 0.5:1; w:w = 4:1) | 7.8 | −12.81 |
| PEG$^{5K}$-(K-SP)$_2$-L$_8$-CA$_8$ + DNA(N:P = 1.45:1; w:w = 8:1) | 25.8 | |

Novel co-delivering telodendrimers were developed by introducing positively charged molecules in the middle layer of telodendrimer for polynucleotide delivery. The interior hydrophobic core of telodendrimer micelles allows for the encapsulation of hydrophobic drug, e.g., paclitaxel. The preliminary results demonstrated the feasibility for co-delivery of gene and drug molecules in one nanocarrier formed by the three-layered telodendrimer.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A compound of formula,

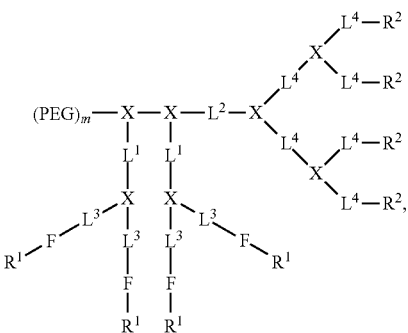

wherein PEG is optionally present, is a polyethylene glycol moiety, and has a molecular weight of 44 Da to 100 kDa;
X is a branched monomer unit;
each $L^1$ is independently optional and is a linker group;
each $L^2$ is a linker group;
each $L^3$ is independently optional and is a linker group;
each $L^4$ is independently optional and is a linker group,
wherein the linker groups is selected from the group consisting of a polyethylene glycol moiety, a polyserine moiety, an enzyme cleavable moiety, a disulfide bond moiety, an acid labile moiety, a polyglycine moiety, a poly(serine-glycine) moiety, an aliphatic amino acid moiety, a 6-amino hexanoic acid moiety, a 5-amino pentanoic acid moiety, a 4-amino butanoic acid moiety, and a beta-alanine moiety;
F is a functional reactive moiety that is a moiety of $R^1$;
$R^1$ is independently at each occurrence in the compound selected from the group consisting of a catechol, a boronic acid, a carboxylic acid, an acylhydrazine, a hydroxyl, an amine, a thiol, and a ketone for labile bond formation, wherein one or more drug(s) are optionally conjugated to one or more $R^1$ groups; or a positively charged moiety;
each $R^2$ independently at each occurrence in the compound is selected from the group consisting of a hydrophobic group, a hydrophilic group, an amphiphilic group, a reversible photocrosslinking group, and a drug;
and subscript m is an integer from 0 to 32.

2. The compound of claim 1, wherein at each occurrence in the compound the diamino carboxylic acid is independently selected from the group consisting of 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid, and 5-amino-2-(3-aminopropyl) pentanoic acid.

3. The compound of claim 1, wherein the diamino carboxylic acid moiety is an amino acid moiety.

4. The compound of claim 1, wherein each branched monomer unit X is lysine moiety.

5. The compound of claim 1, wherein each $R^2$ is independently selected from a rhein moiety, cholic acid moiety, cholesterol moiety, coumarin moiety, curcumin moiety, flavin moiety, isoflavin moiety, riboflavin moiety, retinol moiety, retinoic acid moiety, chlorogenic acid moiety, anthraquinone moiety, xanthenone moiety, Vitamin E moiety, D-α-tocopherol succinate moiety, vitamins, lipids, fatty acids, bile acids, naturally-isolated compound moieties, and drugs.

6. The compound of claim 1, wherein at each occurrence in the compound the linker groups $L^1$, $L^2$, $L^3$, and $L^4$ are independently selected from the group consisting of:

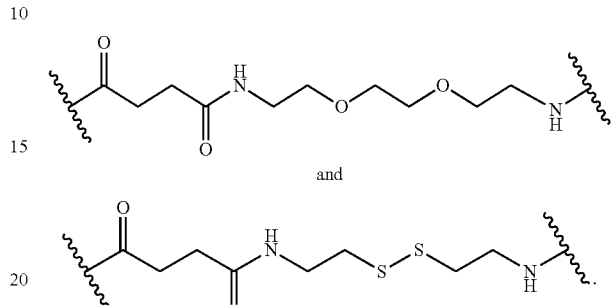

and

7. The compound of claim 1, wherein the linker $L^1$, $L^2$, $L^3$, $L^4$ or a combination thereof comprises a cleavable group.

8. The compound of claim 7, wherein the cleavable group is a disulfide cleavable moiety.

9. The compound of claim 1, wherein the $(PEG)_m$—X— portion of the compound is selected from the group consisting of:

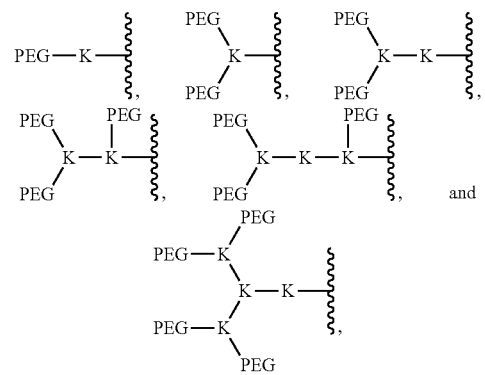

wherein each K is lysine.

10. The compound of claim 1, wherein each $R^2$ is a reversible photocrosslinking group.

11. The compound of claim 10, wherein the reversible photocrosslinking group is coumarin moiety, 4-methylcoumarin moiety, cinnamic acid moiety, chlorogenic acid moiety, or a combination thereof.

12. A nanocarrier comprising a plurality of compounds of claim 1.

13. The nanocarrier of claim 12, wherein the nanocarrier further comprises a hydrophobic drug and/or a non-hydrophobic drug, and, optionally, an imaging agent.

14. The nanocarrier of claim 12, wherein the compounds have an intermediate layer and the intermediate layer has at least one drug conjugated thereto.

15. The compound of claim 5, wherein $R^2$ is selected from the group consisting of the cholic acid moiety, the coumarin moiety, the riboflavin moiety, the rhein moiety, the cholesterol moiety, the vitamin E moiety, and $C_9$-$C_{20}$ fatty acids.

16. The compound of claim 1, wherein PEG is present.

17. The compound of claim 16, wherein the (PEG)$_m$-X— portion of the compound is selected from the group consisting of:
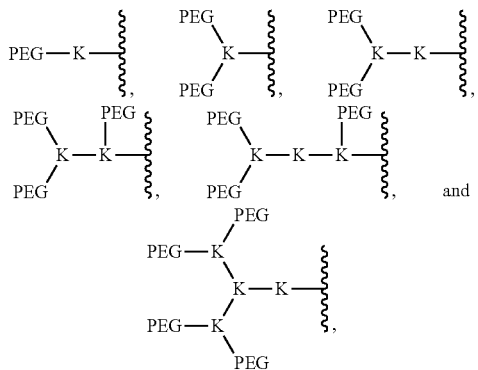
wherein each K is lysine.
18. The compound of claim 1, wherein $L^1$, $L^2$, $L^3$, and $L^4$ are present and each selected from the group consisting of:
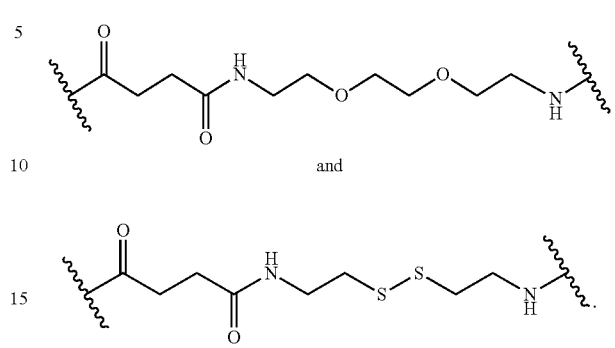
* * * * *